(12) United States Patent
Ching et al.

(10) Patent No.: US 8,900,808 B2
(45) Date of Patent: *Dec. 2, 2014

(54) GENETIC LOCI ASSOCIATED WITH MECHANICAL STALK STRENGTH IN MAIZE

(75) Inventors: Ada Ching, Wilmington, DE (US); J. Antoni Rafalski, Wilmington, DE (US); Stanley Luck, Wilmington, DE (US); Marymar Goncalves Butruille, Des Moines, IA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 911 days.

This patent is subject to a terminal disclaimer.

(21) Appl. No.: 12/502,365

(22) Filed: Jul. 14, 2009

(65) Prior Publication Data

US 2010/0015623 A1 Jan. 21, 2010

Related U.S. Application Data

(60) Provisional application No. 61/080,783, filed on Jul. 15, 2008.

(51) Int. Cl.
*C12Q 1/68* (2006.01)
*A01H 1/04* (2006.01)

(52) U.S. Cl.
CPC ............... *C12Q 1/6895* (2013.01); *A01H 1/04* (2013.01)
USPC ........................................................ 435/6.1

(58) Field of Classification Search
None
See application file for complete search history.

(56) References Cited

U.S. PATENT DOCUMENTS

| | | | |
|---|---|---|---|
| 6,455,758 B1 | 9/2002 | Johnson | |
| 7,401,528 B2 | 7/2008 | Deppermann et al. | |
| 2006/0141495 A1* | 6/2006 | Wu | 435/6 |
| 2006/0223102 A1 | 10/2006 | Broglie et al. | |
| 2007/0125155 A1 | 6/2007 | Barreiro et al. | |
| 2007/0294994 A1 | 12/2007 | Deppermann et al. | |

FOREIGN PATENT DOCUMENTS

| WO | 0149104 | 7/2001 |
|---|---|---|
| WO | 2005012516 | 2/2005 |
| WO | 2007149984 | 12/2007 |
| WO | 2008087208 | 7/2008 |
| WO | 2009089928 | 7/2009 |

OTHER PUBLICATIONS

Wall (Nature Reviews Genetics (2003) vol. 4, pp. 587-597).*
Flint-Garcia et al., Theor Appl Genet. Phenotypic vs marker-assisted selection for stalk strength and second-generation European corn borer resistance in maize, vol. 107, p. 1331-1336, 2003.
Flint-Garcia et al., Crop Science. Genetic relationship of stalk strength and ear height in maize, vol. 43, p. 23-31, 2003.
Flint-Garcia et al., Crop Science. Quantitative trait locus analysis of stalk strength in four maize populations, vol. 43, p. 13-22, 2003.
Lee et al., Maize Genetics Cooperation Newsletter. Chromosome arm dosage analysis—identification of potential QTLs on the short arm of chromosome 5, vol. 65, p. 58, 1991.
Lu et al., Theor Appl Genet. Genetic basis of heterosis explored by simple sequence repeat markers in a random-mated maize population, vol. 107, p. 494-502, 2003.
Cardinal et al., Theoretical and Applied Genetics; International Journal of Plant Breeding Research. Genetic relationships between resistance to stalk-tunneling by the European corn borer and cell-wall components in maize population, vol. 111(1), p. 1-7, 2005.
Bohn et al., Theoretical and Applied Genetics. QTL mapping for resistance against the European corn borer (*Ostrinia nubilalis* H.) in early maturing European dent germplasm, vol. 101(5-6), p. 907-917, 2000.
Krakowsky et al., Crop Science. QTL mapping of resistance to stalk tunneling by the European corn borer in RILs of maize population B73XDe811, vol. 44(1), p. 274-282, 2004.
Ching et al., Planta. Brittle stalk 2 encodes a putative glycosylphosphatidylinositol-anch ored protein that affects mechanical strength of maize tissues by altering the composition and structure of secondary cell walls, vol. 222(5), p. 1174-1184, 2006.
Papst et al., Theoretical and Applied Genetics. QTL mapping for European corn borer resistance (*Ostrinia nubilalis* Hb.), agronomic and forage quality traits of testcross progenies in early-maturing European maize (*Zea mays* L.) germplasm, vol. 108(8), p. 1545-1554, 2004.
James B. Holland, Genetic architecture of complex traits in plants, CurrentOpinionin Plant Biology, 2007, pp. 156-161, vol. 10.
Ada Ching et al., Brittle stalk 2 encodes a putative glycosylphosphatidylinositol-anchored protein that affects mechanical strength of maize tissues by altering the composition and structure of secondary cell walls, Plants, 2006, pp. 1174-1184, vol. 224.

* cited by examiner

*Primary Examiner* — Juliet Switzer

(57) ABSTRACT

The invention relates to methods and compositions for identifying and for selecting maize plants with mechanical stalk strength characteristics. The methods use molecular markers to identify and select plants with increased mechanical stalk strength or to identify and counter-select plants with decreased mechanical stalk strength. Maize plants generated by the methods of the invention are also a feature of the invention.

1 Claim, 20 Drawing Sheets

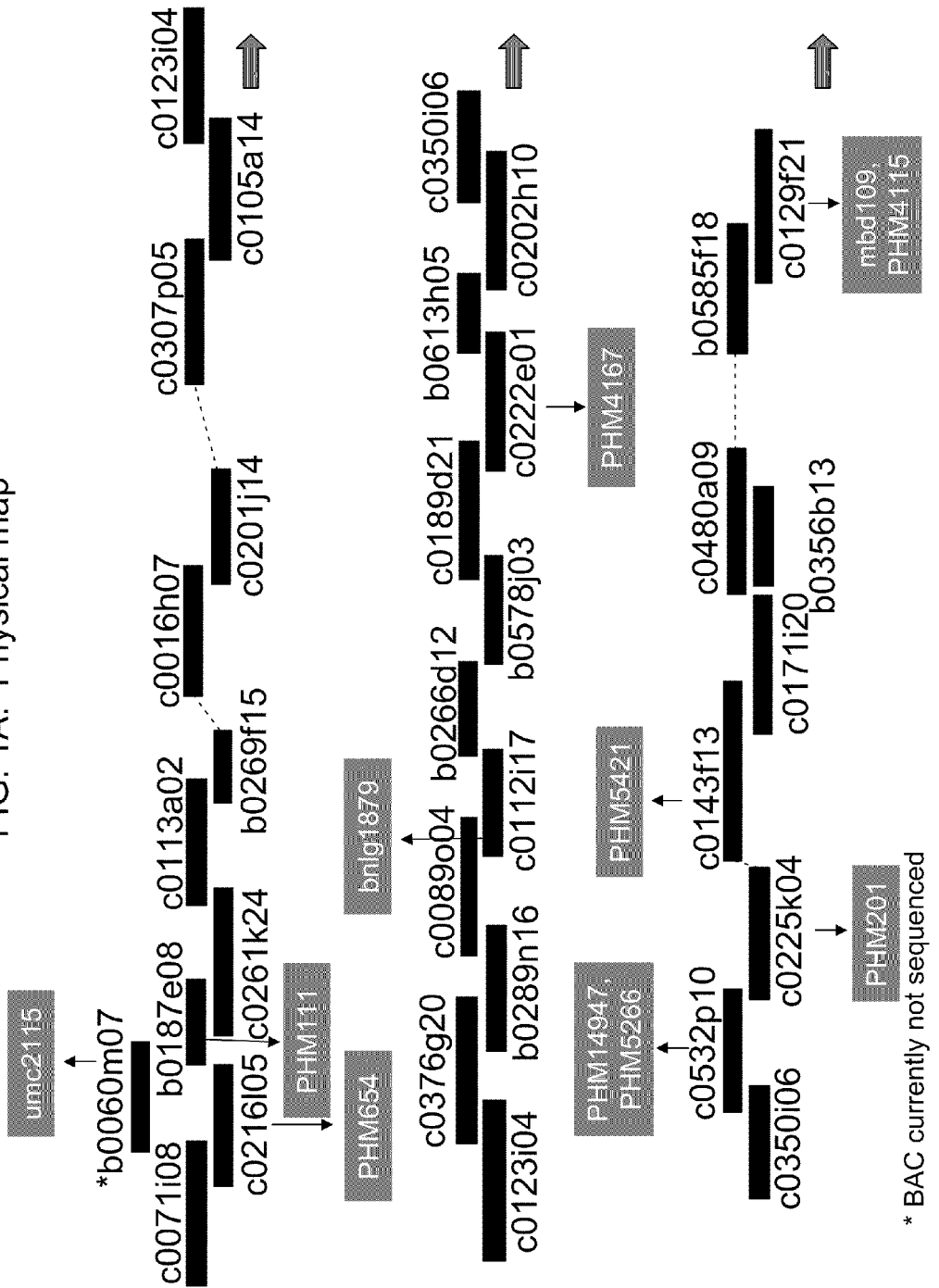
FIG. 1A: Physical map

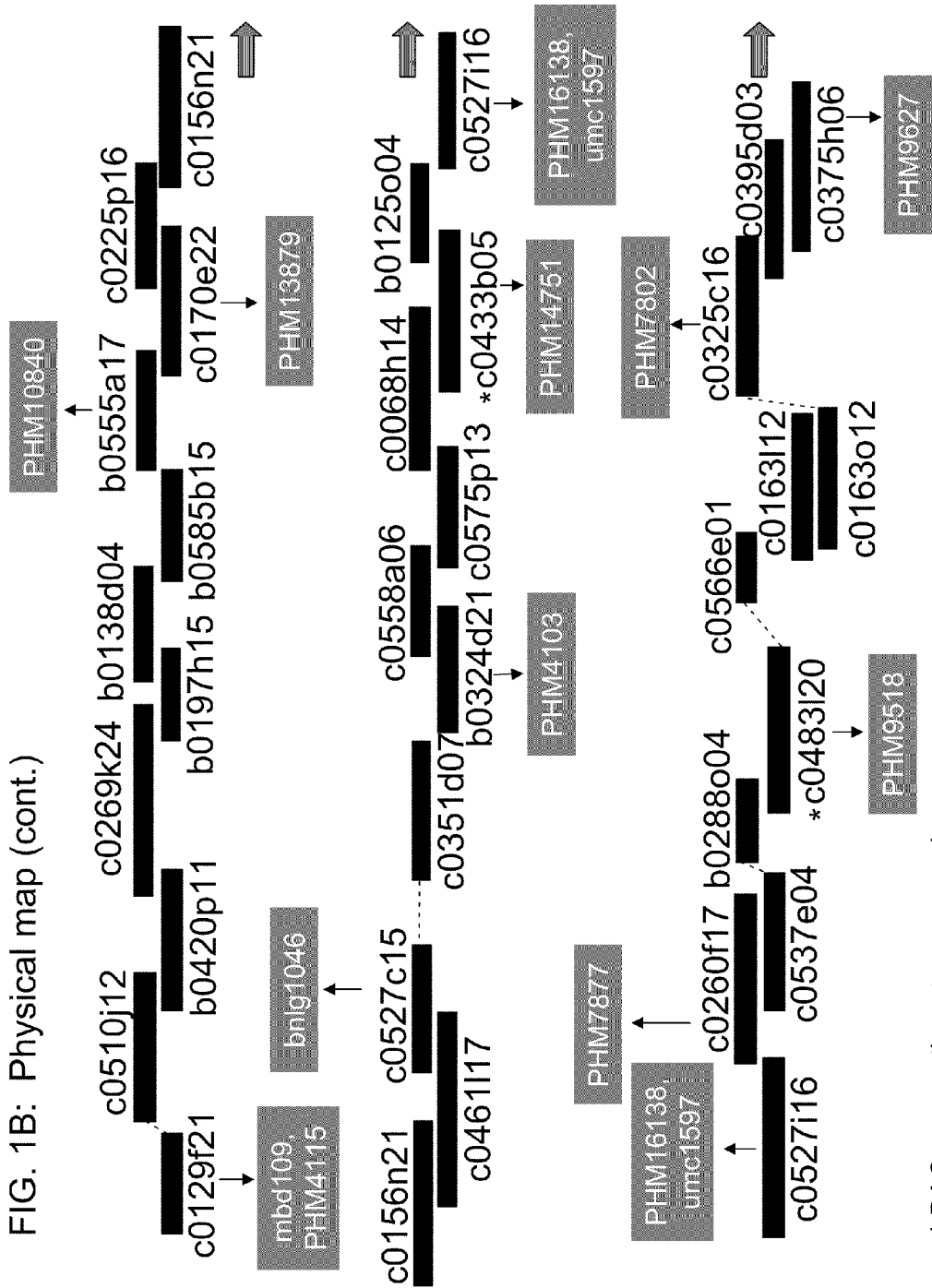
FIG. 1B: Physical map (cont.)

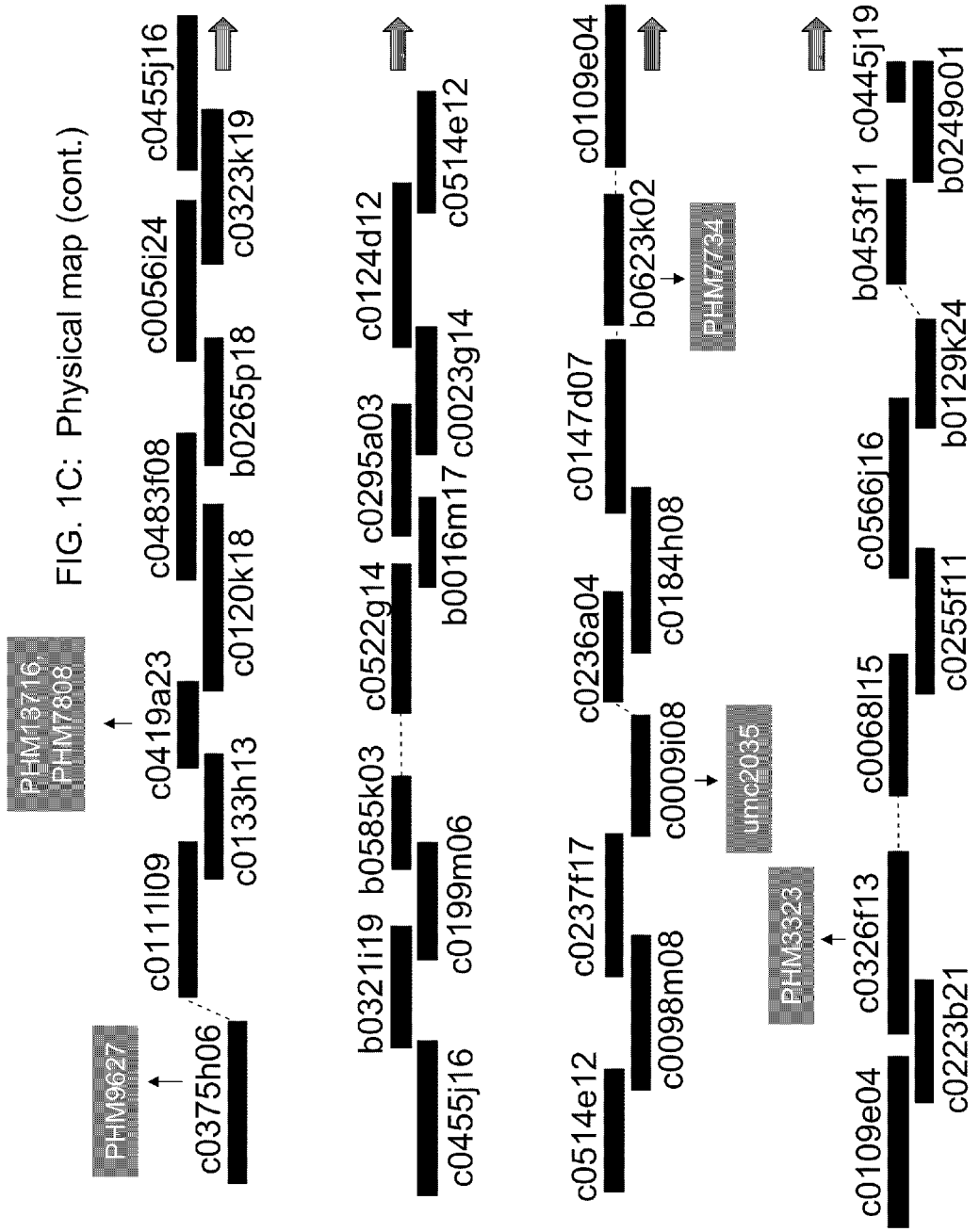
FIG. 1C: Physical map (cont.)

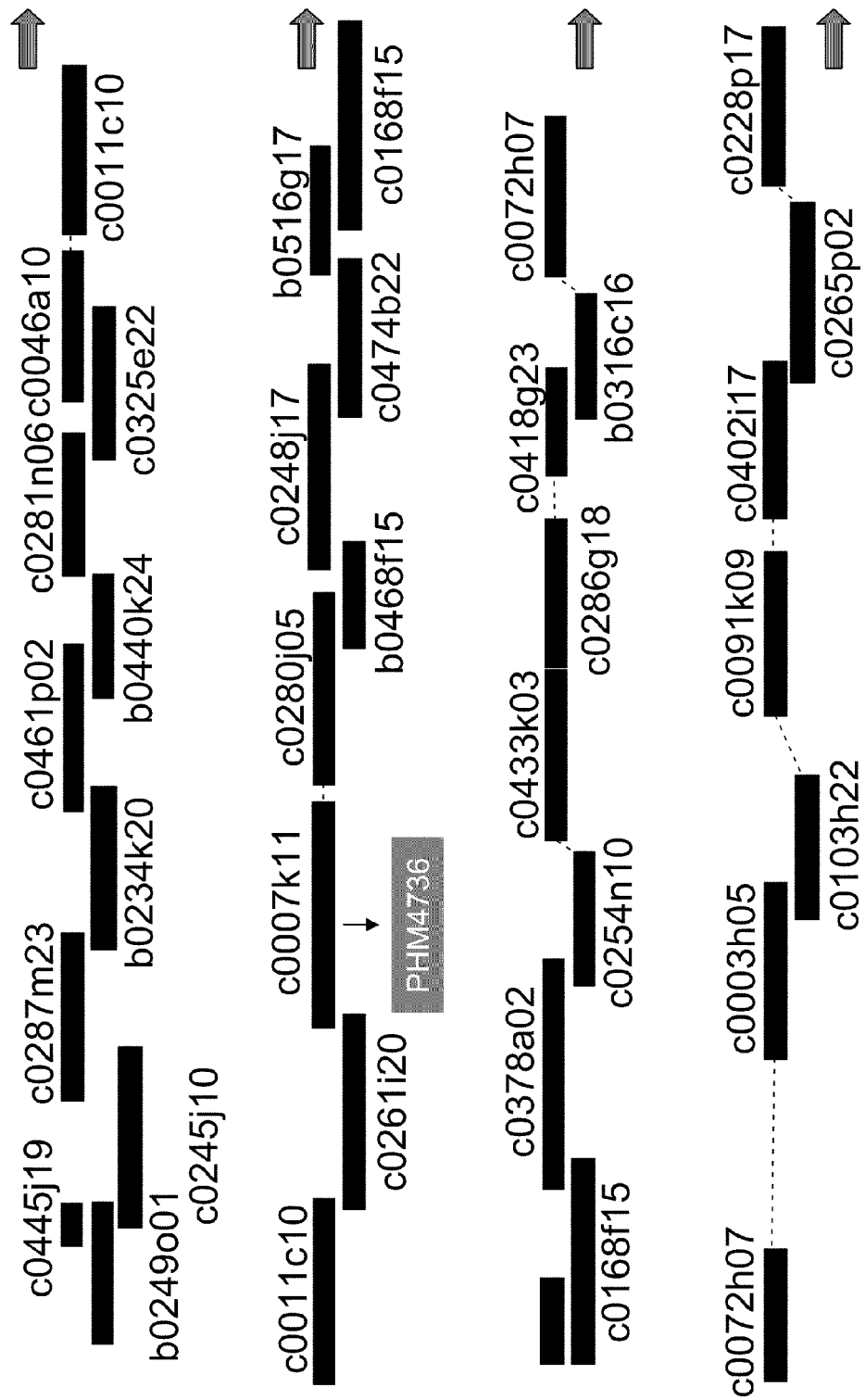

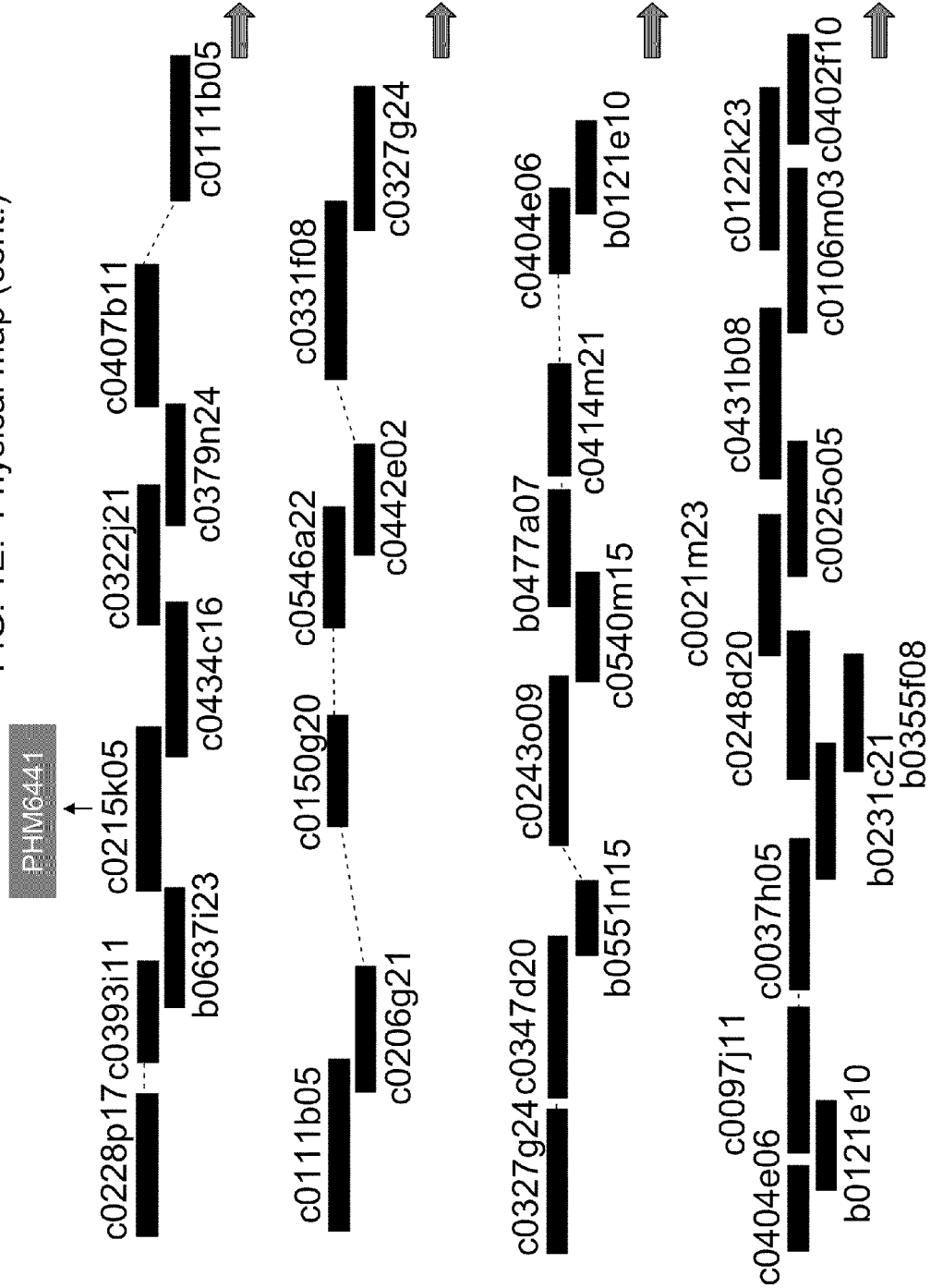
FIG. 1E: Physical map (cont.)

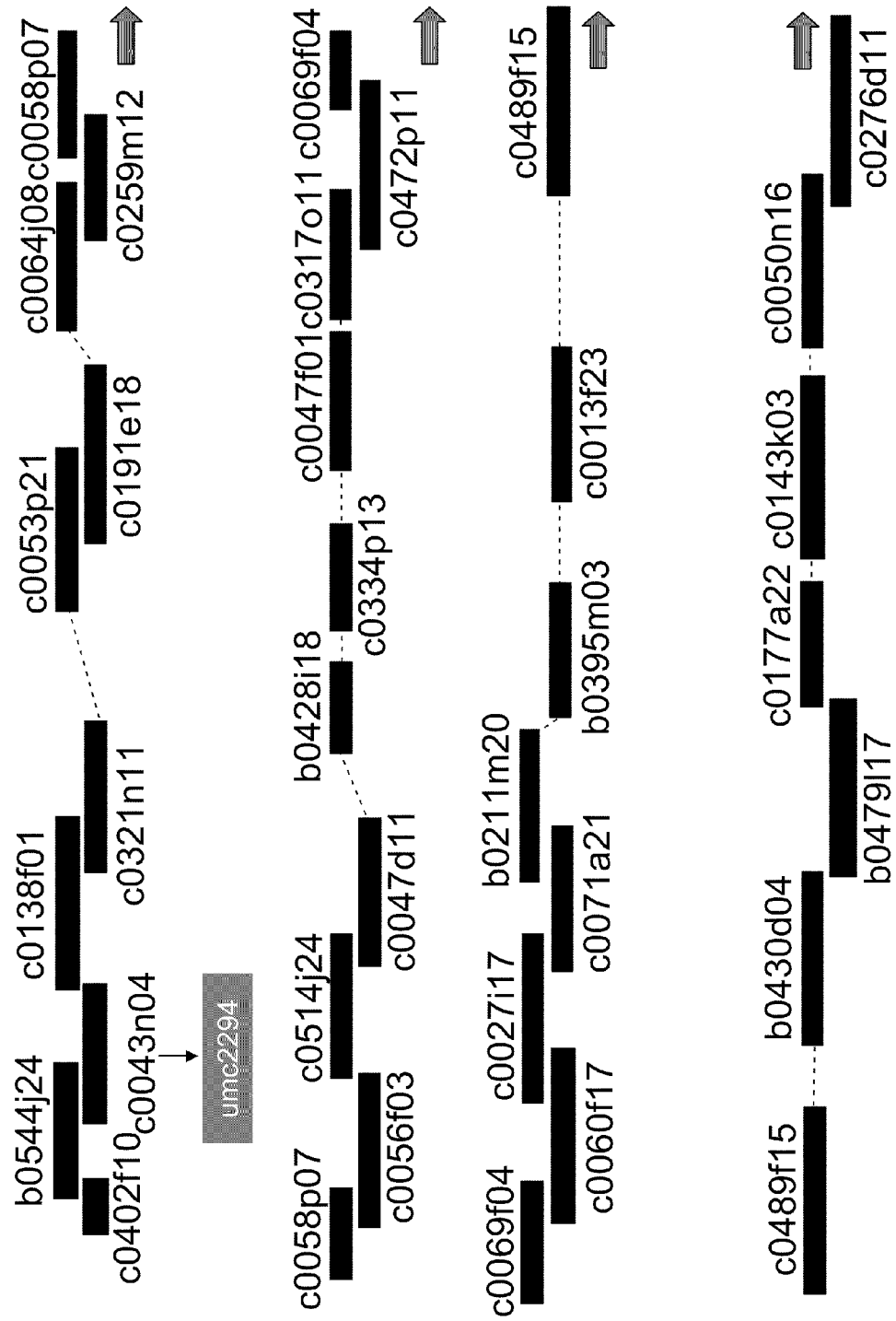
FIG. 1F: Physical map (cont.)

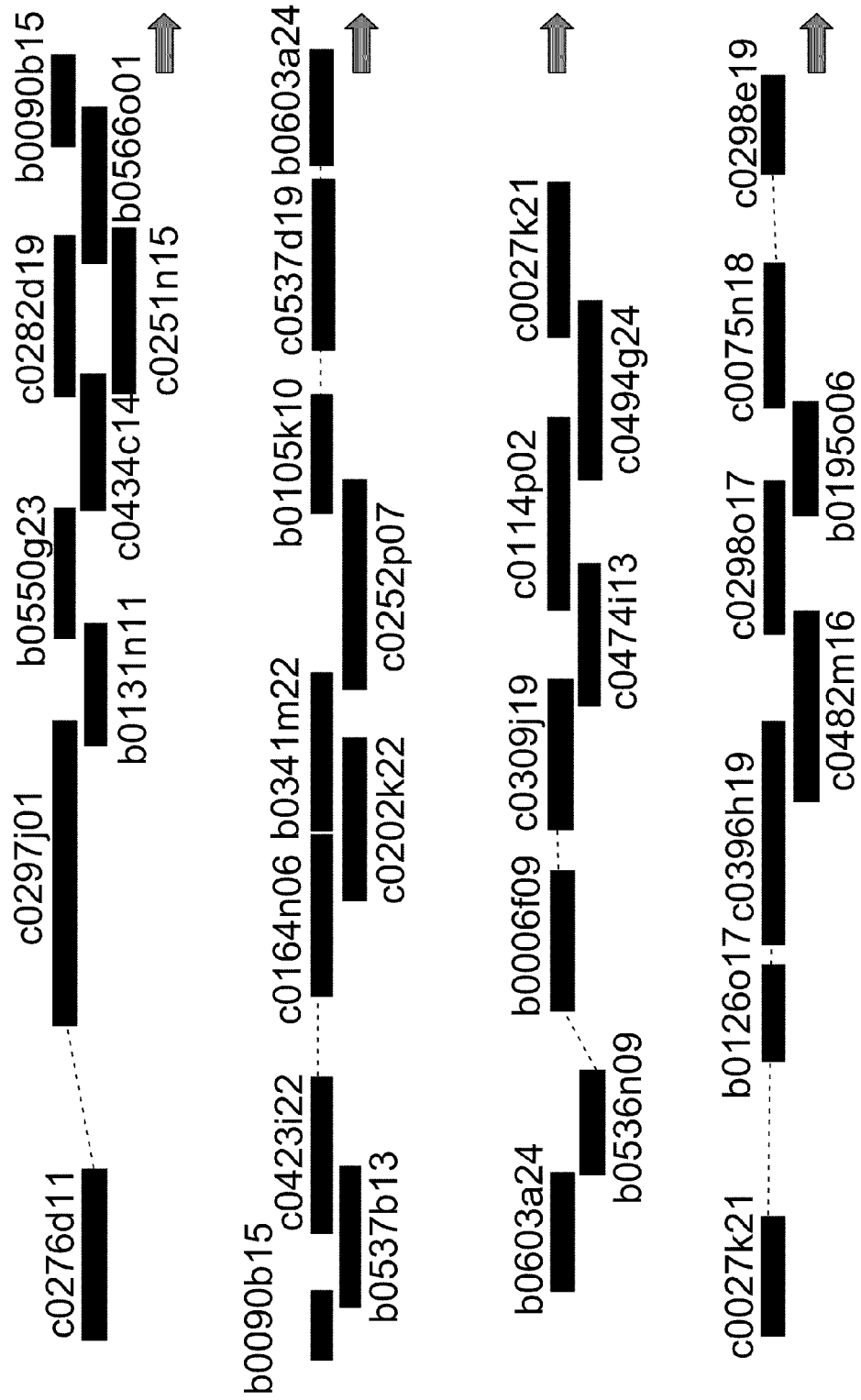
FIG. 1G: Physical map (cont.)

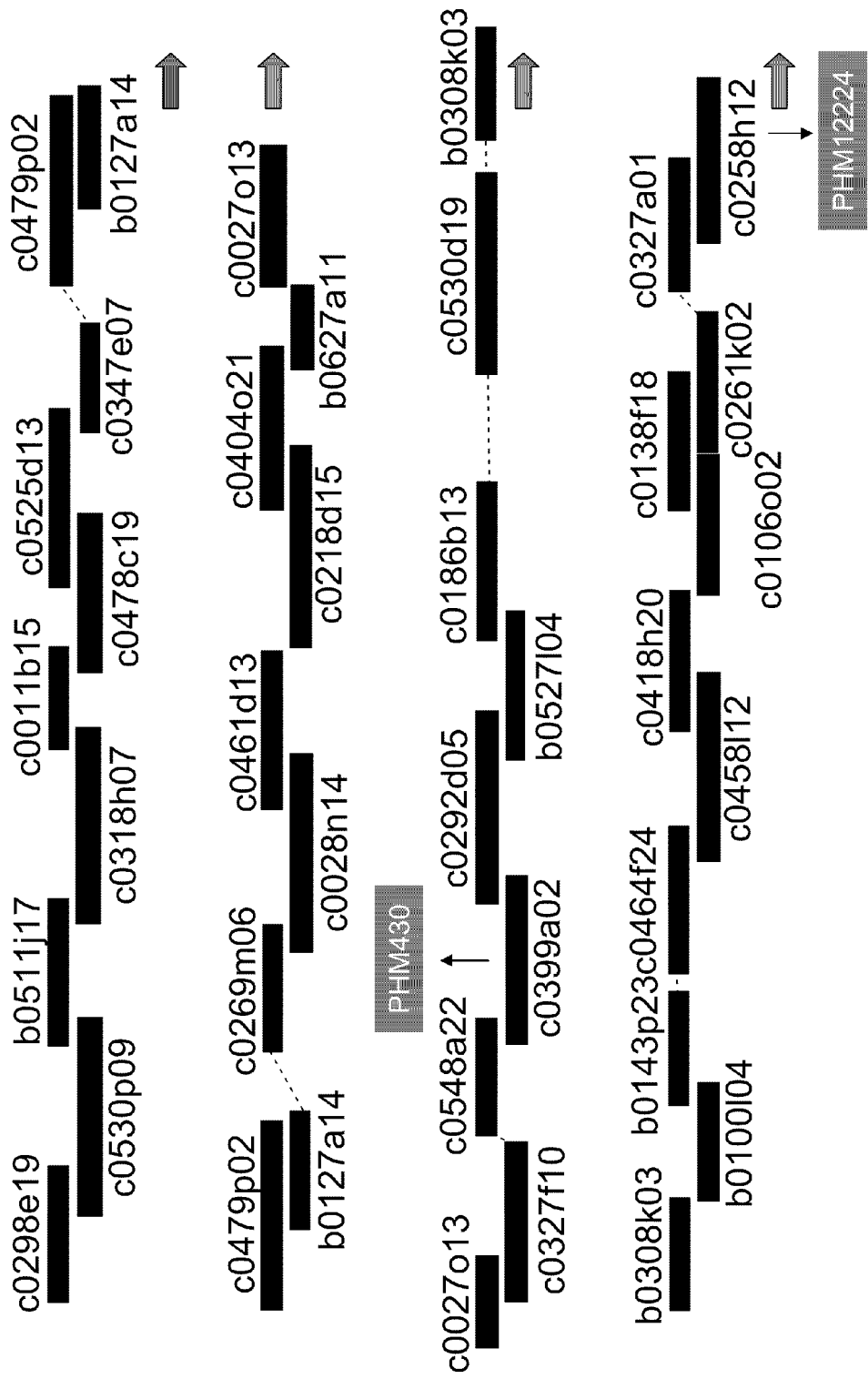
FIG. 1H: Physical map (cont.)

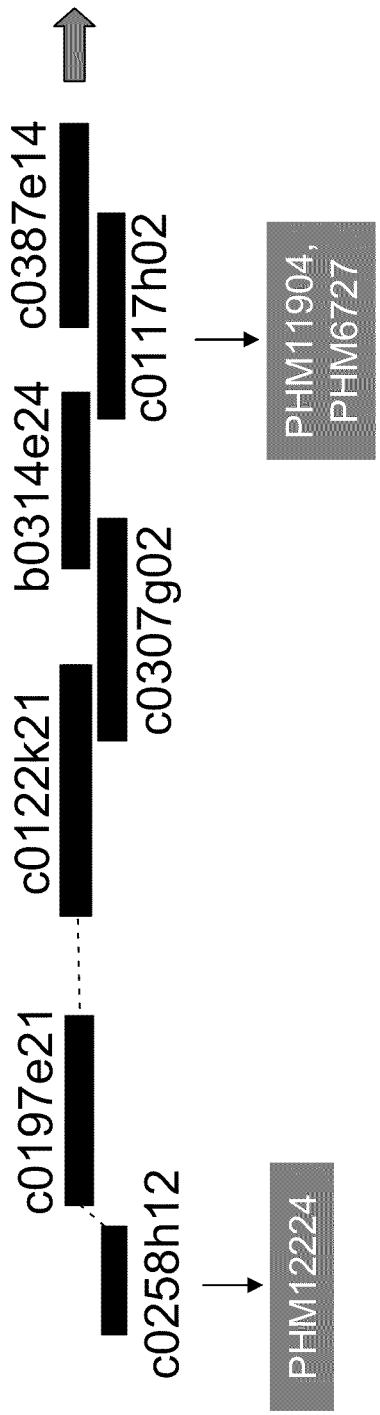
FIG. 1I: Physical map (cont.)

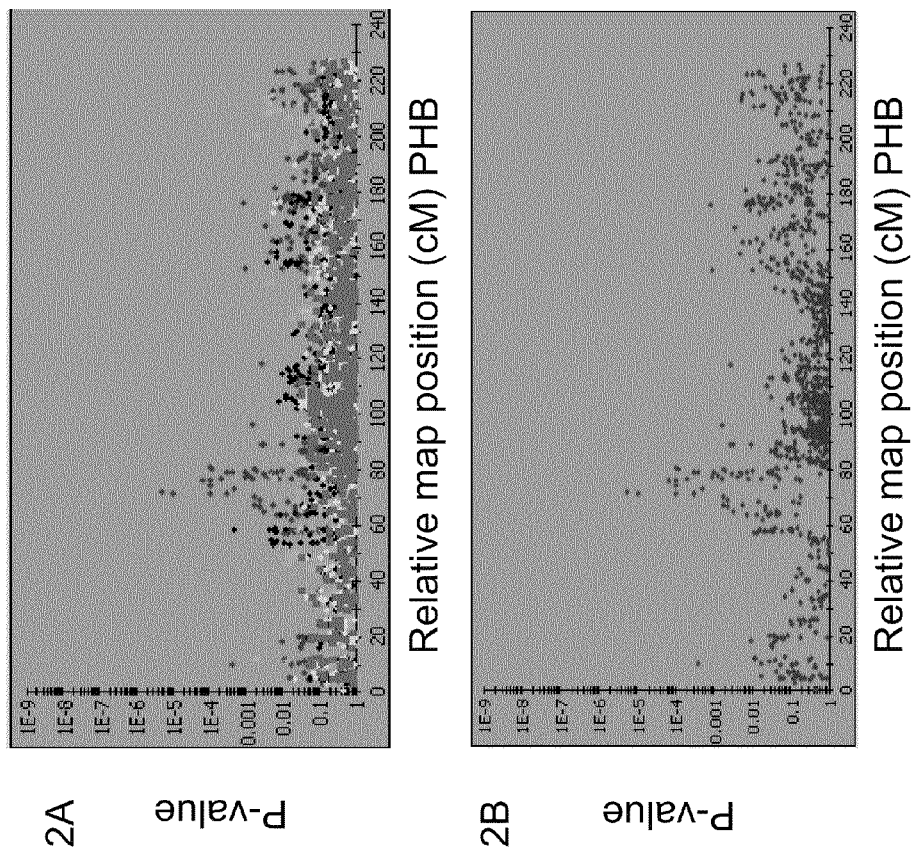
FIG. 2: Associations between chromosome 5 marker loci and mechanical stalk strength FIG. 3: Associations between chromosome 9 marker loci and mechanical stalk strength in NSS subpopulation FIG. 4: Associations between chromosome 1 marker loci and mechanical stalk strength in NSS subpopulation

FIG. 5: PHM Marker Alleles

A) PHM201

| | Identifier | PHM201.9 | PHM201.10 | PHM201.12 | PHM201.13 | PHM201.14 | PHM201.15 | PHM201.16 | PHM201.17 |
|---|---|---|---|---|---|---|---|---|---|
| Polymorphism Type: | | SNP | SNP | SNP | SNP | SNP | SNP | SNP | SNP |
| Position in reference sequence (SEQ ID NO:10) | | 94 | 132 | 135 | 138 | 150 | 171 | 178 | 195 |
| Allele | 1 | C | G | T | T | A | G | T | C |
| | 2 | T | T | T | C | T | T | C | C |
| | 4 | C | T | C | T | A | G | C | G |
| | 5 | C | T | C | T | A | G | C | G |

| | Identifier | PHM201.18 | PHM201.19 | PHM201.20 | PHM201.21 | PHM201.22 | PHM201.67 | PHM201.23 |
|---|---|---|---|---|---|---|---|---|
| Polymorphism Type: | | SNP | SNP | SNP | SNP | SNP | DEL | SNP |
| Position in reference sequence (SEQ ID NO:10) | | 230 | 242 | 270 | 275 | 279 | 321 | 324 |
| Allele | 1 | A | G | A | A | A | W | T |
| | 2 | A | G | C | A | G | W | A |
| | 4 | A | G | A | T | G | M | A |
| | 5 | A | G | A | T | G | W | A |

"W" and "M" refer to insertion/deletion polymorphisms. "W" indicates that the allele is more prevalent in the selection of lines that were genotyped; "M" indicates an allele other than "W".

FIG. 5 (cont.)

B) PHM5421

| Polymorphism type: | SNP | SNP | SNP | SNP | SNP | SNP |
|---|---|---|---|---|---|---|
| Position in reference sequence (SEQ ID NO:12) | 257 | 303 | 314 | 357 | 373 | 426 |
| Identifier | PHM5421.2 | PHM5421.3 | PHM5421.5 | PHM5421.6 | PHM5421.7 | PHM5421.8 |
| Allele 2 | G | G | G | C | C | T |
| Allele 3 | G | G | T | C | C | C |

| Polymorphism type: | SNP | SNP | SNP | SNP | SNP |
|---|---|---|---|---|---|
| Position in reference sequence (SEQ ID NO:12) | 472 | 498 | 501 | 526 | 534 |
| Identifier | PHM5421.9 | PHM5421.10 | PHM5421.11 | PHM5421.15 | PHM5421.16 |
| Allele 2 | G | A | G | C | C |
| Allele 3 | G | A | G | C | C |

FIG. 5 (cont.)

C) PHM3468

| Polymorphism Type: | SNP | SNP | SNP | DEL | SNP | SNP | SNP | SNP | DEL | DEL |
|---|---|---|---|---|---|---|---|---|---|---|
| Position in reference sequence (SEQ ID NO:15): | 93 | 95 | 101 | 105 | 105 | 106 | 116 | 122 | 204 | 213 |
| Identifier | PHM3468.1 | PHM3468.3 | PHM3468.4 | PHM3468.43 | PHM3468.5 | PHM3468.6 | PHM3468.8 | PHM3468.9 | PHM3468.39 | PHM3468.53 |
| Allele 2 | G | C | C | W | A | A | C | G | M | W |
| Allele 6 | G | C | C | W | G | A | C | G | W | M |
| Allele 8 | G | C | T | W | G | C | C | C | W | M |

| Polymorphism Type: | DEL | SNP | DEL | SNP | DEL | SNP | SNP | SNP | SNP | INS |
|---|---|---|---|---|---|---|---|---|---|---|
| Position in reference sequence (SEQ ID NO:15): | 215 | 217 | 227 | 230 | 234 | 236 | 240 | 245 | 249 | 268 |
| Identifier | PHM3468.54 | PHM3468.12 | PHM3468.49 | PHM3468.14 | PHM3468.15 | PHM3468.16 | PHM3468.17 | PHM3468.18 | PHM3468.50 | PHM3468.44 |
| Allele 2 | W | C | M | D | T | A | T | A | M | W |
| Allele 6 | W | G | M | D | C | A | T | A | M | W |
| Allele 8 | W | C | W | T | T | A | T | G | W | W |

| Polymorphism Type: | SNP | DEL | SNP | DEL | DEL | DEL | SNP | SNP | SNP | SNP |
|---|---|---|---|---|---|---|---|---|---|---|
| Position in reference sequence (SEQ ID NO:15): | 276 | 290 | 291 | 296 | 299 | 306 | 327 | 407 | 416 | 426 |
| Identifier | PHM3468.22 | PHM3468.45 | PHM3468.23 | PHM3468.48 | PHM3468.51 | PHM3468.40 | PHM3468.28 | PHM3468.33 | PHM3468.34 | PHM3468.35 |
| Allele 2 | G | W | C | W | M | W | A | A | A | G |
| Allele 6 | G | W | C | W | M | W | A | G | A | C |
| Allele 8 | G | M | D | W | W | M | G | A | A | G |

"W" and "M" refer to insertion/deletion polymorphisms. "W" indicates that the allele is more prevalent in the selection of lines that were genotyped; "M" indicates an allele other than "W".

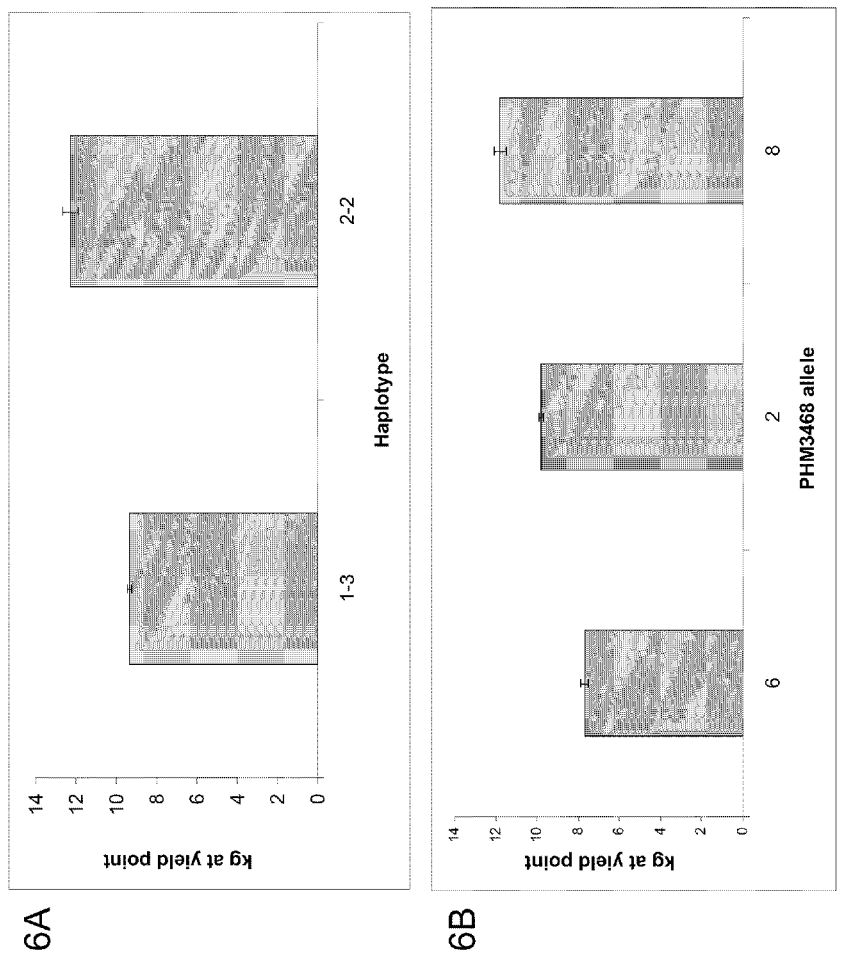
FIG. 6: Average mechanical stalk strength values for: A) haplotypes constituting marker alleles of PHM201 and PHM5421 and B) PHM3468 marker alleles

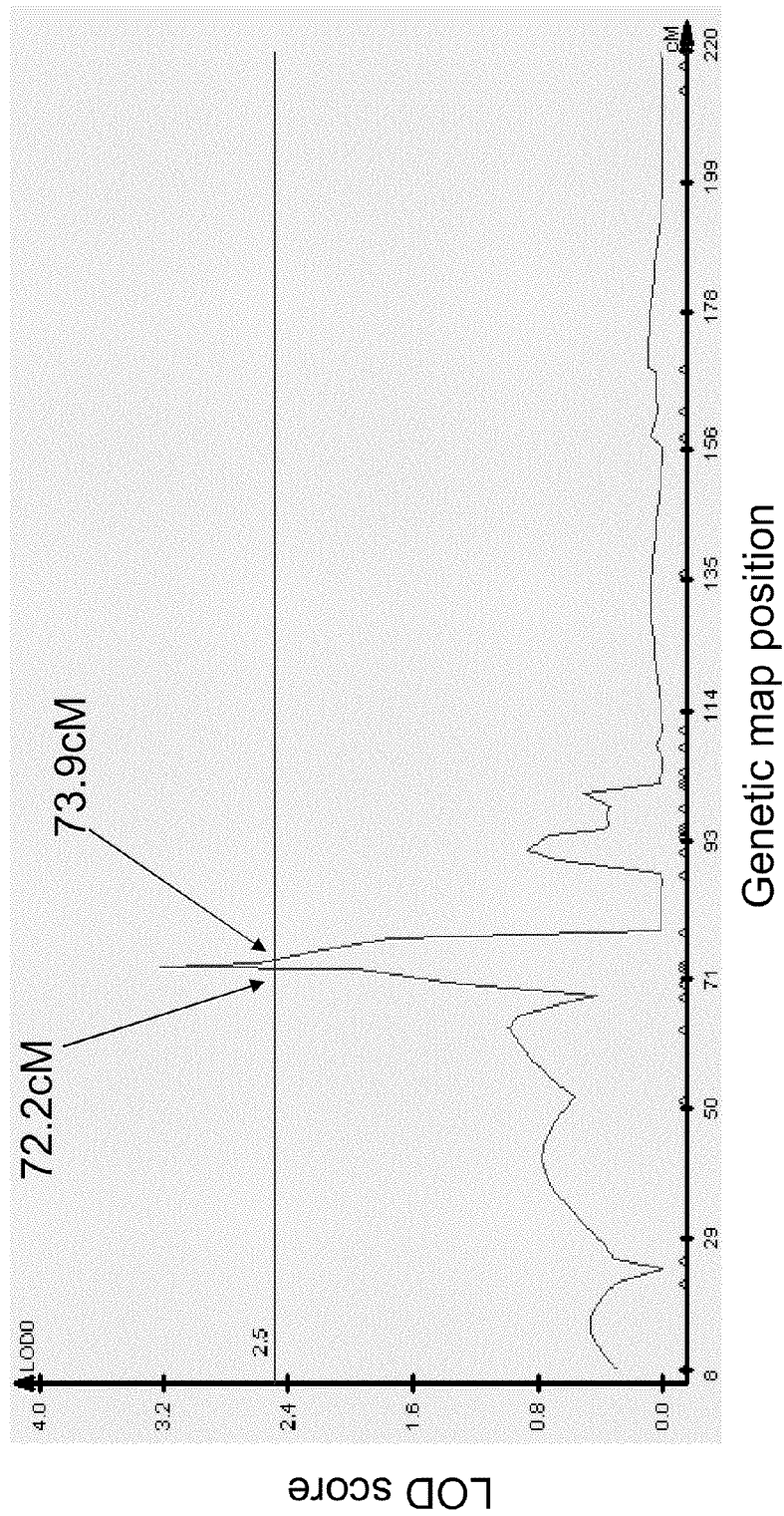
FIG. 7 CIM1

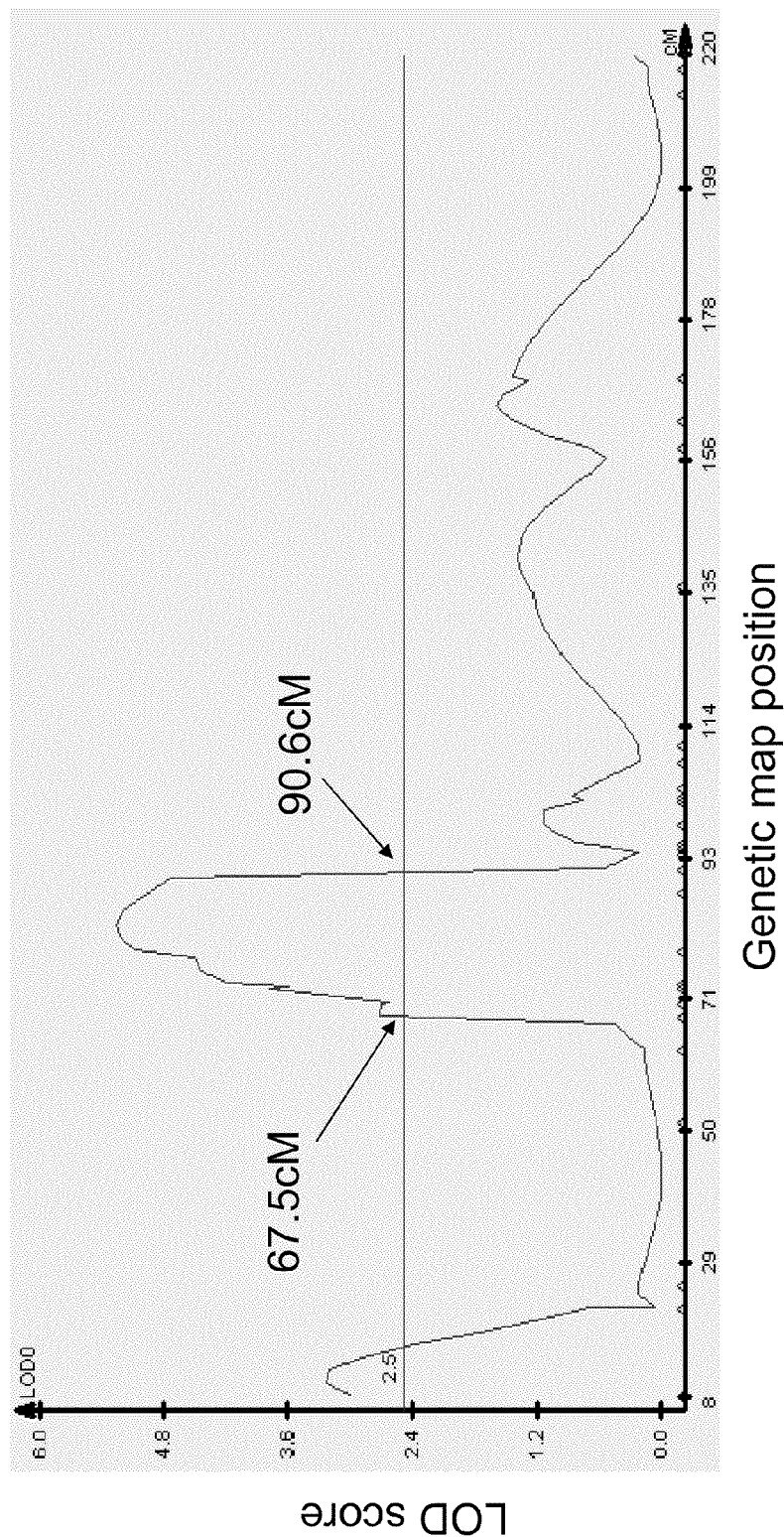
FIG. 8 CIM2

SEQUENCE LISTING

<160> NUMBER OF SEQ ID NOS: 389

<210> SEQ ID NO 1
<211> LENGTH: 537
<212> TYPE: DNA
<213> ORGANISM: Artificial
<220> FEATURE:
<223> OTHER INFORMATION: PHM654 reference sequence

<400> SEQUENCE: 1

| | | | | | |
|---|---|---|---|---|---|
| tcccagtcac | gacgttgccc | ggttccaatt | cgtattcaag | ctgcattaca | ttggcctctg | 60 |
| cttcctctgc | atccccgga | tgtacaagta | ctacatacag | accaaagacg | tggctgcgaa | 120 |
| gcggctcgca | aagctgtggg | ttctcacgtt | aacccttggg | actctctgct | ggctagttga | 180 |
| tcgcatcttc | tgcaagaagc | tttcgcattg | gtatgtcaac | ccgcaggggc | acgcatggtg | 240 |
| gcatgtgctt | atgggcctca | actcatacta | tgcaaacaca | ttcctaatgt | tctgtcgggc | 300 |
| tcagcagcgc | gggtgggagg | cgcgaatcac | ctaccttctt | ggattttgc | cttatgtcaa | 360 |
| ggtccagaaa | ccagagaaga | agagggaatg | atttgtctct | gcttaacact | gatgctactc | 420 |
| agtccaccgc | cagtaagcta | atgtctatcc | ctcaccccat | ccccaccca | atgtgcgcag | 480 |
| acaagttgtg | gcattttgt | atatggcatc | caaatgatta | cgactataat | tcgacgc | 537 |

<210> SEQ ID NO 2
<211> LENGTH: 636
<212> TYPE: DNA
<213> ORGANISM: Artificial
<220> FEATURE:
<223> OTHER INFORMATION: PHM111 reference sequence

<400> SEQUENCE: 2

| | | | | | |
|---|---|---|---|---|---|
| cgaccakrgs | tcraaartar | ccksgsccaa | gccggrsgsr | scccmsgacr | actcykccca | 60 |
| aamawaaagw | gaamcaaccg | racaarcgya | ssaacccrcc | cmggscccac | acamcamaaa | 120 |
| ccccaacaca | gcsammaaaa | aacaaaaaaa | cacacgargg | aaattcccag | tcacgacgca | 180 |
| ctctgccaaa | ggacgaggta | tgtttccagc | aagtgaatgt | actgtcatgt | tcttggcagt | 240 |
| actgttcgac | gttctgaat | gatttgattg | acttgtatca | aacgaaaacc | gtctaggtgg | 300 |
| agaggatggt | tgacgaagct | gagaagtttg | caaaggagga | taaggagaag | agagatgcca | 360 |
| ttgacaccaa | gaaccaagcc | gagtcggtca | tctaccagac | cgagaaacaa | ctgaaggaac | 420 |
| taggggacaa | ggtcccggc | gacgtcaagg | ggaaggtcga | gtcgaagctg | caagagctca | 480 |
| aggatgctgt | tgctggtggc | tccacacaga | cgatgaagga | cgccattagt | gcattgaacc | 540 |
| aggaagtcat | gcagattggg | cagtccctct | acagccagca | ggtgccccag | gcgccggacc | 600 |
| tgtccagctg | atgcttctgc | tgttcagcgc | gcattc | | | 636 |

<210> SEQ ID NO 3
<211> LENGTH: 526
<212> TYPE: DNA
<213> ORGANISM: Artificial
<220> FEATURE:
<223> OTHER INFORMATION: PHM10100 reference sequence

<400> SEQUENCE: 3

| | | | | | |
|---|---|---|---|---|---|
| gtgtcccccc | gggtggtatt | gtttgtattg | ttgatatgaa | tatctggtat | gcatggactg | 60 |
| actatgttt | cagtgattgc | ctgtcaccgt | tggtctgaat | atctggtgaa | catagatatg | 120 |
| ctcagtgacg | gtgcttgtca | ttgttgttgg | tctggatatt | tgggttcgca | aggatatatt | 180 |
| tgcagtgctg | agatgcaagt | gcttaaccga | actgtagcca | aagtaaccct | atgctagaag | 240 |

```
tagctggcaa ccatgttgaa ttgttaatct cgttagtttt ttgtctgggg tcttgaaaat        300
gccctccaga tctctcacgc gaacgtgaac ttcacctatc ttctctatcg agctgcatcg        360
ccctctcttt tggcgagcag gtctttggat tcaccgtttg cttgtgtgat atctgcttag        420
ttgtgtgggg atgatcaagt ggttggaaag ctttgctgtg actgttcgtt gatcttcttt        480
ctgccgctgg ttggatatgg tcatagcggg gccttggcgg gggggg                      526

<210> SEQ ID NO 4
<211> LENGTH: 459
<212> TYPE: DNA
<213> ORGANISM: Artificial
<220> FEATURE:
<223> OTHER INFORMATION: PHM7357 reference sequence

<400> SEQUENCE: 4
gggaaggtcc cagtcacgac gctgatgttt aatcattaca agaattaag agcaagtcga          60 aacatgaatg tactgcctga gatgtacata tcagtgcata catttattga ctccattttc        120
acactgtttt atgttatctt tatacagaac gagaacaggc tgctctggaa attggggaca        180
ttgccgccag ggcttctaac ttttttacaag ctgacacacc ctctggacaa atcatggcat       240
gtgcttggtt tagggtacaa tccgaccgtt gagcgctcag aaatagacaa tgccgcagtc       300
atccactaca atggtaacat gaagccatgg ctggaaatcg caatgacaaa gtatcggcct       360
tactggacaa agtacatcaa ttatgagcat ccttacattc atggatgcaa gttcagccaa       420
tagaactacc taaacattct tcgggaaatt tgttgtaa                               459

<210> SEQ ID NO 5
<211> LENGTH: 468
<212> TYPE: DNA
<213> ORGANISM: Artificial
<220> FEATURE:
<223> OTHER INFORMATION: PHM5349 reference sequence

<400> SEQUENCE: 5 taccaaccccc tctagctgat agcgcaaatc gtggtgttat atttcaatta tatttgaagc        60
gcttgagagg aatatacata gccactggaa tcaagcagtt catggtctca ctgcaaatgt       120
gcgcaagatg tttctggaca tggacagtga actatttgaa gagtgccagc agcagtatat       180
ggataaacaa gcaaaagcca aagagatgca ggagcaacga gaatcagcat ggagacaatt       240
ggaagctgtt gttgctgcca aggctgctgg ggatgacatg ttttggtca actaggtaat       300 ataaccaacc tttccacttc atttatttgt tagtgcttgt tgttttagt cttgtaacct       360 aaaattgtac tacttttgtt ctcggctttg ttctagcata tctgtgagat gcattgccac       420 ttttttgtact gctcaccttt tgtttatggt caaagctgtc ccaccaac                   468

<210> SEQ ID NO 6
<211> LENGTH: 632
<212> TYPE: DNA
<213> ORGANISM: Artificial
<220> FEATURE:
<223> OTHER INFORMATION: PHM4167 reference sequence

<400> SEQUENCE: 6
cctttaatgt aactttgcta cctttgatag cttatcatac tatccttctg ggttcatgtt        60
acatgtgttc cctttttactg tgctagacaa atcggacct tgctcattta ataagtagct       120
gatgatcttt ttgtttttga taccaggttc ttgccactct acatgaagct ggttttcatg       180
```

```
ttgatattga cgcgagtgac aggacaatac aaaagaaggt acttaccagt taccaagctc    240 tttttaggctt ttgcaccgtt tcttttaatt tcttgttctt atatttgctt gttcctttt    300 atacaatttt ttcaataaaa aagaaggaa ttgcatgtag ccaactgtga gacctcaata    360
aattctgcag gtacgggaag ctcaactggc ccaattcaac tacattcttg tcgtaggtgc    420
acaagaggcc gagactggaa atgtaagtcc tctttacctc gtgtcctcct tttcttctgc    480
atgcggcgta cttaccagta tcaccaatat tgctgcaacc aaaatatatt tggttccttt    540
ctgtttgacg tggatctcct gtgtaactgc agatatgcgt tagggtaaga gacaatgctg    600
acctgtcaca acgagtaaat tggggtaatt ac                                   632

<210> SEQ ID NO 7
<211> LENGTH: 543
<212> TYPE: DNA
<213> ORGANISM: Artificial
<220> FEATURE:
<223> OTHER INFORMATION: PHM14947 reference sequence

<400> SEQUENCE: 7
gcggaggcaa acttacgttg gaccggtgtc ggctgcgtgg gcgcatctcg tcgctgcagg     60
agcaggtgga ggcgctgcag gcgcagctgg cgctggcgca ggccgagatg gtcaggctca    120
ggatgaccaa cgactacatc gtgcaccgcc tcaaggcggc cagcagggcc ggcggcgggg    180
gcagcagcta cgccggctcg ccctcgtcca tgtcctcgcc caagacgcg gagccggagg    240 cgcactgcaa ggccacgccg gagctgctgg acatggtcgt ggaccagccc ggcatggacg    300
acgcccactt ctggtcgtcc tactagccta gggccgggat ggaggccgct gacaaccgcg    360
cgctccatcg ggcgcttctc ttctgatcta ttagtcgtcg tgtcgtcgat caggtgctgt    420
tttttgagtc acagatggtg gtaatggtgt catcaggtat atggtgtgcg cgcgctggta    480
acagcgtcac actaggagga atggaaggcg agcgtacgta tggtcatagc tgttcctacc    540
cgg                                                                  543

<210> SEQ ID NO 8
<211> LENGTH: 643
<212> TYPE: DNA
<213> ORGANISM: Artificial
<220> FEATURE:
<223> OTHER INFORMATION: PHM5266 reference sequence

<400> SEQUENCE: 8
ccttaaaaat tgctagggta aatgtgaggg acctggtac aataaacgat ggcctcggtg     60
ctgctcgtga agcagatgcc ctattggttc aggatgagtc taccaggagc cagcaagagg    120
gtcaacagaa tggaatttct gagccagctg ccaacaatgc tctccagtat caagagcaaa    180
accctcagcg agctggaagt accctgcag gctcaggctc cctcaaccca tttgggtccc    240
ttttgctgtg gttgctggga ggcggtgctt ctgatggcat agtttctttc ttctctatgt    300
tcagagatgt tcgtgatcat ggtcaagatt acaccgatcc acctcgaaat ggaaatgatc    360
aggtgacata gaatcatggg gatgaaagtg ggccaatgac tgaactcgag tgcttgggcg    420
gcagcagtct ctttctaata tgatataatg ccagcacctc ccttcaaaag gataatgacg    480
aatattggtg gcaactatac agactggtgt cgctggagat gccatgttag tattatctgt    540
ttctcacttt tttagttagt aggtaagggt gaaggttgta tctatatcat tacatgtgca    600
cattccctac cgtctgaatg gagcgcccct ccatcctaca tat                      643
```

<210> SEQ ID NO 9
<211> LENGTH: 451
<212> TYPE: DNA
<213> ORGANISM: Artificial
<220> FEATURE:
<223> OTHER INFORMATION: PHM12632 amplicon sequence

<400> SEQUENCE: 9

| atattaaggg gaaggtccca gtcacgacgc atgtatttct tacaggttag cgatttggaa | 60 |
| agccagattg ataacttcga agcagagatt gaagggcttt caattaaaaa gggaaagcaa | 120 |
| agaccgcctc gattggtaag aacagctata ttcattccat accaatacta cttttattat | 180 |
| tttttattga acttgttttt ctgtaatttg tatggttgta agaagtgatt ttgcatgatt | 240 |
| aggtacattt agagacgtct attacgagac ataaagctca tataaagaaa ttggagtcaa | 300 |
| tcttgcggct tttggataat gatgagttga gtcctgagca agtcaatgat gttaaagatt | 360 |
| ttcttgatga ctatgttgaa cgtaatcagg tatgtctgcc ttcgtagttg actcatgctc | 420 |
| tctccatcct aattggggac gggctgttta t | 451 |

<210> SEQ ID NO 10
<211> LENGTH: 376
<212> TYPE: DNA
<213> ORGANISM: Artificial
<220> FEATURE:
<223> OTHER INFORMATION: PHM201 reference sequence

<400> SEQUENCE: 10

| gttmgagaaa tttcccagtc acgacggatt ctcgtgtgac catgaattct aaatgtacat | 60 |
| aaaagtctgg cggaacttat agcatcttgt aatctctgtg agccgcggtc tgtcagtatt | 120 |
| gggtgggctt gctgtggtaa ctggtggaca tgtcgagttc atccatttgg gtaggccttg | 180 |
| gtgaacacgg acgccccaca tcatgtctca gtttgagtag tttgtgtgaa ctgaagggta | 240 |
| cgtgcttctc ccatgtggtt gcagcgttaa cttgagtcaa gtgctaacaa gagtagataa | 300 |
| aattttgccc cagttcgtct ttgtgacagt cttttaaagt cttttttctg agtatctttc | 360 |
| aaagttttca ggtaaa | 376 |

<210> SEQ ID NO 11
<211> LENGTH: 502
<212> TYPE: DNA
<213> ORGANISM: Artificial
<220> FEATURE:
<223> OTHER INFORMATION: PHM4861 reference sequence

<400> SEQUENCE: 11

| ggtaagaccc agtcacgacg ctgctgggtg ttcttgtgta cgctttctac ggccgaaccc | 60 |
| acagctccct aatagatgtt gtctacgttc cggcagcgca agctgatgag atatacagga | 120 |
| gttcatcagg atatgtatca tagaaaagaa cagctgcagt catgtgacac gatagagcca | 180 |
| cagaaagacc gagcggatga cagttactca aaaggtggtt gtccatcagc tgtagaaaat | 240 |
| tggttatcag ccggggaaga cggaactgac tgttatttct ttcatgctcg gctagcatga | 300 |
| tctcgtggat gcaactttgc aagatatgta tgctgctcac gagccaggtc aatttataca | 360 |
| ttgttggagt gtgtagatat ggtgtatata aaaccaactg ggtggagtat gtgatgtcat | 420 |
| acataataat ttgtctaatt catgtaaaag ccctttgtgc agttgtgctg aaatgtgagg | 480 |
| cattaaagac ctatatttttt tt | 502 |

<210> SEQ ID NO 12

<211> LENGTH: 583
<212> TYPE: DNA
<213> ORGANISM: Artificial
<220> FEATURE:
<223> OTHER INFORMATION: PHM5421 reference sequence

<400> SEQUENCE: 12

```
gtccgacgac gactgggtga ctgccggcgc cccaggcctg agcctccatc ttcgggccct      60
tcactggcta cgagcaccac caggtacgca taccctcct cttccgttcc ttctgtacga     120
gcaccctaac cctagtttaa gatacttgta atcggatctg atccaatttc aggtgtactg    180
ggtccgatcc atctgagtct gatcttttgt ttctcgggtt cctggcagag gattatggat    240
tggctggggc agaagcgcgc ggagatgctg atgcaggtgc tgctggtggc gtctgctgtg    300
gcggcgttcc tggtgggcta cgtgcgcgcg gacttccagc tcatgctgct cgtctacgcc    360
ggcggcgtcg tgctcacagc gctcgtcacc gtccccaact ggcccttctt caaccgtaac    420
ccgctcaagt ggctcgacgc tgccgaggcc gagcgccacc cgcgccccca ggtcagcgcc    480
ggtgcggcag caggggaaa gaagaagtcc ggaagaacaa gtaatcgatc tttcggagcg    540
atatgtgttc ttgtcgatta ctaaacctat tatttatttt ttt                      583
```

<210> SEQ ID NO 13
<211> LENGTH: 542
<212> TYPE: DNA
<213> ORGANISM: Artificial
<220> FEATURE:
<223> OTHER INFORMATION: PHM4115 reference sequence

<400> SEQUENCE: 13

```
caagtcaaaa cgttgtaatc gttggtgaag agaaaactga ggacagtcag gcagctgaat      60
ctgcggtgcc ttccctggcg tcttcagagg gagagaagaa agagaacggt ggtgccactg    120
aaccagcagc acctcctcca gctgatgcag acaagggcgc ggagaattca ggccaggtga    180
acaccgcccc ccaagaaccg acggcagcga actgcgacaa ggggcagatc caacctggtg    240
cctctgctgt caggtgcaca taagggagct tggtctccga tgagagaccg ttgctttgtg    300
tgtttagggc ataccctcgc atttgctttg agaattataa tcgtggttaa cctgacagga    360
cagcgctgtg cagcactagg ctgcccagca cgtagttatc ttttccgtttt ttttatggcg    420
gcagggacaa atgcgtgtac ccggttcaaa gtgtaactcg ttattagcgt gctgaacatt    480
gatctctgga gcggactgga ggacgtagta ctgtctccaa cttttttaacg aatttkgggt    540
tt                                                                   542
```

<210> SEQ ID NO 14
<211> LENGTH: 547
<212> TYPE: DNA
<213> ORGANISM: Artificial
<220> FEATURE:
<223> OTHER INFORMATION: PHM12521 reference sequence

<400> SEQUENCE: 14

```
gggaggggt tcgcggtgtc gacggtcata gacatgtaac acttagttac ttgcttagtt      60
gccatataca tgaataaact ggacacggta aacagtaaa tgcactgtaa acataatga    120
gaacactatg ttatcgggtt tgatccgga gacctgacca atatgtcgca catgtttgaa    180
ctgacgcttg tattcctgat gtagaacagt gaacagttac cattcactag ctaccacaac    240
ctcttagcat cctcaaaaca ttgccttttt catttcattt acaatatttg cagcttgcta    300
ctgtgcgaaa ctatactatg caatagcaag gtgttcatct ttctgaggg atctcagagt    360
```

```
gcaatatcaa atctaggact gcatgccaaa ataatttgtt gtatgcttat agctgtatca      420
cactgaaatg tgtccgtttc cattcagctt gagatgatgt ctgatgctat tgatgaaaca      480
cttacaaagt gagcaaaggg gtaattaaag gggaagggc taaaaaaaaa aaaaaaaagg       540
gggaagg                                                               547

<210> SEQ ID NO 15
<211> LENGTH: 666
<212> TYPE: DNA
<213> ORGANISM: Artificial
<220> FEATURE:
<223> OTHER INFORMATION: PHM3468 reference sequence

<400> SEQUENCE: 15
ccgtgattgc cccgttctgc ggaagccgac ctgaggatgt caaggggtac cgggagctcc       60
gggaggccct ggaggccatg ttcgtctcct ccggcagcgc caacgacaac aacaacctgt      120
cggagttcgc cgtcacctac caggacaagg acggcgacct catgctcgtc ggagacgtgc      180
cgttcgagta cgtacagcgt tttttccatc tctcatcttc cgttctagct tgttcatttt      240
ctttgtacaa tacgttgtta cgttacgtac cagcagcaag attaatcgcg ctgacgacga      300
cgatggtgtg ttctttaatt tgattgatct gcaggatgtt cgctagcacc tgcaggaagc      360
tgaggatcat gaagagatct gaagccacag gcctgggatc ggcgagacaa tgaagaaggt      420
ctgacgacga ccgagggccc gacaacgttc atgtcgatct cttcttttt tttcttttg       480 ccccattatt ttattttgtt cttcttgtcc gagagacccc aagccaaaag gatgagcttg      540
gtgggtggcg catcaatcta caaagcgcat gcatatacgc ggatgtgttt tcggctttgg      600
ttctgtaaga cgacgactag tagctaggtc ttttttagca gcagcccaga agctaaatgg      660
tcaagc                                                                666

<210> SEQ ID NO 16
<211> LENGTH: 533
<212> TYPE: DNA
<213> ORGANISM: Artificial
<220> FEATURE:
<223> OTHER INFORMATION: PHM10840 reference sequence

<400> SEQUENCE: 16
ttcagatgca gatggctatg ttctccatta cttggtcaca aattacaggt aaaaaaaaac       60
tctccatgga ttgtgtaagt acttatcaat ataactactt atcaaccaac tatatatatg      120
acaaaatcat tattgtgttc tcgtgaatat ataggtggaa acccgtcagc ggtgggacaa      180
tgttattcta tccaggactg caatttccag aaggcttcca catccagctt cttccaaaaa      240
tcccaaacgt ggttccataa accctatgaa gaaatatgaa tacagaataa tttaagcaaa      300
tattctaaat gtaccatggg ggaatgaatt gaagttcgat aacgatgtgg tacgggctga      360
ttatggtgac ctagggatca ctaggaggat gggaggtcga attaaggagt aaattagttc      420
atttccccat caaccccttc caatcctccc gtgatccact tgttaccaaa tcaaccctaa      480
tggtagcagg tcgaattgtc ggaatggtca tagctgcctt ggcgcggggg ggg             533

<210> SEQ ID NO 17
<211> LENGTH: 520
<212> TYPE: DNA
<213> ORGANISM: Artificial
<220> FEATURE:
<223> OTHER INFORMATION: PHM12755 reference sequence
```

<400> SEQUENCE: 17

```
cccagtcaca acaaaatcag ccgcgacgac gatgacgacg gaggaggagg agagtggggt    60
cccgacgtcg agcgacatca actctctgag gtcgatgagg ctggccaaca acagcggtgg   120
gagcgagagg agcagcggca gcagtgacgt gaacaacaag agcagcgacg acaggagcgc   180
cgccgcggcg gggaaggcga aggggacgat gctgatgccg aagaagatgc tgagcaagct   240
ctggtccggg aaaacgaacg ccggcgagag cagcagctcg acacgtcgg atagccctgg    300
gtccgccaac ccggaggagg cgaagtccac gcagtcgcgg atcacatggc gctcggtatc   360
ctagtcgcgc gcgcgcggcg ggggttcagc ggggtcacag gctcacagcc ttagttttgt   420
tcttggtctt gattttgcct tcgcctagcg agtacagcag tagcgatctc ataacatatg   480
agttactgct actgtttcac tgtcataatt tcttattaag                         520
```

<210> SEQ ID NO 18
<211> LENGTH: 569
<212> TYPE: DNA
<213> ORGANISM: Artificial
<220> FEATURE:
<223> OTHER INFORMATION: PHM13879 reference sequence

<400> SEQUENCE: 18

```
aacgagagca cccactaaac cccgttcagg acgacgtcgg cgggctcgac gtccggcggc    60
gctccgacgg cgagtgggtc cgcgtcaggc ccgtgcccga ctctttcatc atcaacgtcg   120
gcgacctcat ccaggtacgt gctcacctga tgaactgagc tgaacataag ttgcatgcac   180
tgcatgtgta tagctaggct tctcagatcg cttcgtgtgg cgtaaggtgt ggagcaacga   240
caggtacgag agcgcggagc accgggtgtc agtgaactcg gcgagagaga ggttctccat   300
gccctacttc ttcaacccgg cgacctacac catggtggag ccggtggagg agctggtgag   360
cgaggacgat ccgcccaggt acgacgccta caactggggc gacttcttca gcaccaggaa   420
gaacagcaac ttcaagaagc tcaacgtgga gaacattcag atcgcgcatt tcaagaagag   480
cctcgtcctc gcctaactac gtactgctag tactggccta ctgctaggat ccatgccatt   540
gccatgtcat ggtcatagct gtgctttcc                                     569
```

<210> SEQ ID NO 19
<211> LENGTH: 633
<212> TYPE: DNA
<213> ORGANISM: Artificial
<220> FEATURE:
<223> OTHER INFORMATION: PHM4103 reference sequence

<400> SEQUENCE: 19

```
ttcaggcatc tgttatggac acttgggggt tgatgtccaa gatttgaagt ttggctacaa    60
aatgcgaaca gatgtttgga acatggata attgactgca gaaatcatta cttacgttcc    120
aatttatgtg atcctgtgtc tatgattatg gtagcatagt caatcatttt ggaatcccac   180
aagcattttc tcagttgtac tagttgtcat gttttttttta cgaactttct gttcttcgtt   240
tttaatttct cgtcgaagtt tcttatagta acctgacctc ttcgggaatc cgatttcgca   300
ggcaactttc agtgacattc ttaagaagct cggtaagatt ttgagacatg ttttactgat   360
tttcagtcgt tcatgctaga tgcactaaca aactttatct tgtagacaat cactacaaaa   420
tggatctgac cccaaagaaa gaagccatca agttatgat ccaagacgag ttaaccaagc    480
tatcagagga ggatgaagaa ggagagggag acgaagacac cggaagaaa cagcagcagc    540
ctcaggcgca ggagatcgag gcatgaggat ccgcgaaccc cgtagctgta gtagccgctg   600
```

```
ttaattatcc tgtacttagg cgtatttcca tag                                    633
```

<210> SEQ ID NO 20
<211> LENGTH: 696
<212> TYPE: DNA
<213> ORGANISM: Artificial
<220> FEATURE:
<223> OTHER INFORMATION: PHM5363 reference sequence

<400> SEQUENCE: 20

```
ctgccgtccc ccattttccg gacgagaaat cgccatcacc agctgcgcca tggacggcta       60
cctcgacgag ggggtggggtt ctcttctcgg cgctgccccg ctctgctctc tagtcattcc     120
aatcatgtgc cattccttcg tcgtgaaaat actatctata gtcatggcgt cgccgcgcta     180
atattgcagg gggatcggtg caagctggat atcgtgagcg ggtgcacgga ccccagctcc     240
gacatgttcg acccgctggc caccgtcgac gacggctcct gcccctcga gtctgatttc      300
gaggaatgaa ggagcttcag ttcgatccta aaaagttagg acccttaaat aattttagtt     360
taaaaatgaa taggaatagg atcccatcct aatccgatta gatccttaaa gtttgtagcg     420
taaaattgaa agcccattac caccctatg tccatacatc ttatcagtgc aagtttgtga      480
tcatgtgata cattaagcat atacgtgtat gtatttcacc agagtacctg caccggtgag     540
caagatgatc tcctacttgc accaccatta gagcagtgga tatgatctca tacttgcgcg     600
ttgcactagt agagttgtgg atacttagga tccatcattg caaactctga tacaaacgat     660
cttgccatca ttaaattgtg caaacctagt gtccat                               696
```

<210> SEQ ID NO 21
<211> LENGTH: 736
<212> TYPE: DNA
<213> ORGANISM: Artificial
<220> FEATURE:
<223> OTHER INFORMATION: PHM14751 reference sequence

<400> SEQUENCE: 21

```
acaaactgtt tttcgttgcc cacggtttca aggtttggtt ccctggaggt ttcatagtat       60
gaccttcaaa tgcatgtagg tgtgcaatgc atacaccgag ttaaacgatc ctgttgtgca     120
gagacaacgg tttgaggggc aactaaaggt aattttttaac ttaatgaaca ctcaagtaac    180
tgtgcagatt gtataattct tttagaagca acctagtcat cactatgttt tggatttctg     240
agttcatgca tgcaagtatg caactaagaa tatagaacca aaaaggattg tatgttggaa     300
aggatagaat gccaatagca caaagttcat gaacctttt gctattatat ttacagtcag     360
gaattaactg agacttgcat atgattttcg tatccttgtt ttcttaggag tagagagttg    420
tataatctgt atcttctgct caggatcgtc aatctggtga tgatgaagct atggccttgg    480
acgaaacatt ctgtgctgcc cttgagtatg gtctaccacc aacaggtggt tggggcttgg    540
gaattgatcg cctcacgatg ttgcttacag attctcagaa cattaaggtt cgagtatttc    600
catcaactct tttccatatg aatttccaat gctttcttga cattcttggc tttcagtgga    660
atattattga ctgatcatat tatctttcaa tgcaaactca gaattttcat tcaattttat    720
tcaaattttt ggaaaa                                                    736
```

<210> SEQ ID NO 22
<211> LENGTH: 452
<212> TYPE: DNA
<213> ORGANISM: Artificial
<220> FEATURE:

<223> OTHER INFORMATION: PHM16138 reference sequence

<400> SEQUENCE: 22

```
cgggaaagtc ccagtcacga caagcgtgag ctcggctact accgcccaaa ctacaggggc    60
aaccagtggt caggcagcgt gctccccgac gtcctgccgg tgaagcctga cgtcggtccg   120
gcccacgtcg tctcgcacaa gagaggcgct acgacggtgg gtgtcacgcc ttggatcgac   180
aactacaatg tccccgtgct cgtgtaaggac gtcgccaccg tcaggaggat cacccgtggt   240
gtcactggac gcagcggagg gcttcccacg gtgcaggctc tcgcgctctt ccatggagat   300
gactgcaccg agattgcgtg cttgctggat ccagaccatg ccagcgccta tcaagttcag   360
accgtcgtgg aacagattgc aggagaccag ggacttgagg ttgagcagga tactacactg   420
acataaccaa gacgagggaa ggggtagaaa aa                                  452
```

<210> SEQ ID NO 23
<211> LENGTH: 542
<212> TYPE: DNA
<213> ORGANISM: Artificial
<220> FEATURE:
<223> OTHER INFORMATION: PHM7877 reference sequence

<400> SEQUENCE: 23

```
gggggagggc ccagtcacaa catcgacgcc aagcatgaca aaggggtcgt ttggagaagc    60
atgaaacgga tactggaacc tcttgtgaca cccgacaccc ttcagaatga ccctgtgaaa   120
gagctccagg aattctgtga tagcaaaggt tacactttgg agtacacggt aactcgtgac   180
aacggtgtat cctcggtggt cgcagaagtg cggaccgaag ggactacgta caaggccact   240
cggacaggct tctctaagct tgacgccaaa aagttggcag ccagttccgt gctccgtgat   300
ttgaaggctg cggacacaaa gcagtactct gcaaatggta tcagctgcac ttaagcttca   360
tagctctatg gtataatact tttgtacaaa atcgtcgaat cagtaaggtg tgcaggtgcc   420
taggcacgct acccctacttt tactgcatct acgtctacgg ccacactaaa gcagtacgta   480
cagcaatgtt ttgttttggt catgtctctt gagagtgaaa gttagcttta ctttcttaat   540
aa                                                                   542
```

<210> SEQ ID NO 24
<211> LENGTH: 446
<212> TYPE: DNA
<213> ORGANISM: Artificial
<220> FEATURE:
<223> OTHER INFORMATION: PHM9518 reference sequence

<400> SEQUENCE: 24

```
gataaaaaag gaagtcccag tcacaacgga aatggccagg tccagcgcgg atgggctgtt    60
ccagtttgcg gcggtgatca atctcaacct cgcagccata aacttgttgc ccttgccagc   120
attggacggt ggcaccttgg cattgatcct tcttgaggca gcccggggtg ggcgcaagat   180
cccccgagaa gttgaacagg gtattatgtc atcggggata ctggtggtgc tcatggttgg   240
catgttcctc attgtacgtg acacactcaa ccttgatttc atcaaggaga tcttgtgata   300
cttcgcgtga aaaatcaatt gattgcagtt gtagtaaaat tgccagtgtc agaacttggt   360
tggcttggaa atgtgtagtt gttgtgattc ttttttgcctt tgatggactg ctctagactt   420
tactttctta ttaagtakws ttgatt                                        446
```

<210> SEQ ID NO 25
<211> LENGTH: 676

```
<212> TYPE: DNA
<213> ORGANISM: Artificial
<220> FEATURE:
<223> OTHER INFORMATION: PHM7802 reference sequence

<400> SEQUENCE: 25
cccwattggg gggttgcatc cgtccccatt gggtttgcac tacatcgtcg gcatccgctc    60
gggtgctcct aggcttctac tttgacctcg agcagcggt acgcacgacc tctctgcgcg   120
tggcgttctt cgccgtcact ttgtcttcga cgtctcaggc ttgatacgat ggctgctgga   180
tacaacggtt gcagggtatt tggagcggta tgatcggcgg caccttgatg cagaccttga   240
tcttgatatg ggttacattc aggaccaact ggaacaaaga ggtgtgcaga ccgcaataaa   300
cttaatttgg ttttctgtat gcgcgcgtac attgaagtct tcgaaattta aatttcgcaa   360
ttcacccagc tctacatgta tgtattgaga tgcattcatt tcctaatctc tctctctctc   420
tgtctctccg aatgcaacaa tgcaggttga agaagcacag aagaggttaa acaaatggga   480
cgacggcaag gctcctctgc tgtcagcgca agaatgaaac aactcgtctc tctggtgccc   540
aaccaaagaa caacgagacg tggatatgac ctgtagggaa ctagggacgc ccctcggcag   600
gctcagcgga gacgtcgacg gagtttgatg tcaagtagca attccaccat gtcctaaaat   660
ggacaaaacc gggaat                                                   676

<210> SEQ ID NO 26
<211> LENGTH: 745
<212> TYPE: DNA
<213> ORGANISM: Artificial
<220> FEATURE:
<223> OTHER INFORMATION: PHM2134 reference sequence

<400> SEQUENCE: 26
tttttgggtc agaattttag ggcccagttg gttatagga ctccacatta acttagagtg    60
tcctgggcaa atttaaacca twtgaaaaag gatttgaaat ttctaatgga aaatgcttct   120
aaaatttttt gaaccagata ctaatatatg gattttatct tgcttaaaaa cctatttctt   180
cagggcatca gctgaggagg ccataagggt gctaaatgga agccagctgg gaggtcagag   240
cataaggctc tcatggggcc gtagccctgc aaacaagcag gtaactaact tgtttttatc   300
taatttgcgt gcccttttact tgctgcttta gttcacatcc ccctcgagtg gacatctccc   360
ttagcccgat cgctggattt ctgttccagc ctcagcaaga gcagagccaa tggagtggtg   420
gtggctatta tgggtatccc caaggatacg atccatatgg ctatgctcgg ccccctcaag   480
atcctgccat gtacgcctac gcagcatatc cagggtatgg aaattaccag caacagccac   540
cacagcagcc cccgccacaa caggtaggca cgtttctcga ggcacttgtt gattggtcgt   600
gcaattgtgc gccactaatg atgtcttgtt tctccctttg cagtaatgat gtcccgagag   660
tgatcatttg caagctggtc gcaaatagct ggggttggg cgcagcaact ttggtgcgtt   720
gcatgagaaa tttgcgcgtg tgtgg                                        745

<210> SEQ ID NO 27
<211> LENGTH: 502
<212> TYPE: DNA
<213> ORGANISM: Artificial
<220> FEATURE:
<223> OTHER INFORMATION: PHM7808 reference sequence

<400> SEQUENCE: 27
ggggtaggtc ccagtcacga cgaatggtgg agctgcttcg aagcccgggt tcaatggcta    60
```

```
aagcatgcga cgagcttgca acagtcatcg gcccaagaaa agacatcgag gaatctgata      120
ttgggcggct gccctacctc caagccgtgg tgaaagagac cttcaggctg catcctgctg      180
ccccgctgtt gctaccgcgg cgtgcccagg ccgacgtgaa gatgatgggc tacgtgattc      240
ccgaaggttc tcgagtgttc gtaaacgtat gggcgatggg ccgagacgag gagacgtggc      300
ctgagcctga gaagtttatg cccgagaggt tcctgggaa gaagacgcac gcaggcggtt       360
gatctcaggg gcggggactt cgatctcatc ccgttcggtg gaggacgccg gatctgccct      420
gggatgccgc tggcgatcag gatggtgcat ctgctgcttg cgtcgctctt gaatcagttg      480
catgagtact ttgggttaat at                                               502

<210> SEQ ID NO 28
<211> LENGTH: 513
<212> TYPE: DNA
<213> ORGANISM: Artificial
<220> FEATURE:
<223> OTHER INFORMATION: PHM9627 reference sequence

<400> SEQUENCE: 28
tcgcgctgtc ccggtttgac ggggacagga tcggaagcag gatcgaccgg gtcccggcgg       60
ttacgatcac aactacatgc tcgactccgg cgaagtgagg tcaggcctgc ggcatgtggc      120
gcacgtcgtg gacccgtcca gctcgagggc cctggacatc tgggccgacg cgcctggcgt      180
gcagttctac accggaaatt ctcttggtgg cgtcgtgggc aaaggaggcg cggtctatgg      240
gaagcacgct ggcctctgcc tcgagacgca gggtttcccc aacgctgtta ccagccgag       300 ttttccctcg gtcgtgtttg gccccggtga gaggtacagc catacgatgc tgttcgagct      360
ctctaccgag tgagtcatgt agcccgtctg cctgcccgtg tagatagata gatatacacc      420 gttttatt tccttgttgt tttgtgcttg cgagtagtta agaaactgtg gcgcgcgcgg        480
cgatgatgca aatggtcata gctgcctggg gcc                                   513

<210> SEQ ID NO 29
<211> LENGTH: 627
<212> TYPE: DNA
<213> ORGANISM: Artificial
<220> FEATURE:
<223> OTHER INFORMATION: PHM13716 reference sequence

<400> SEQUENCE: 29
gggatcgtga gaagctttgc caacttttag ggcagaatcc aaaacttttg caaaagctcc       60
cgggaaaatc ttgggaaatg gagttcaagt agtcacttca aattttttgat ccgctggaag    120 ttatttatgc tttgagtttg attacacctg catttggaaa cctagaggat tgggttgatt     180
ggaagggtac cctttaatct caaactgtga tgcaaattga ttttagtttt ttttttctct     240
cgcattgcta acaggatcgc attggccagt tgtagtcgca ctggaggtgc tattgtgaaa     300
gtgaaatctg atgctggtcg atcgctaggt tcctagagta tggtgttgtt ttgttttcgg     360
ctatggctgt agctagatga aagcaactgc cagcttgcta gtcgccgaaa tgtattccta     420
tgtacattat atgtaacttt gttctgtaat gtgaaaattt gtaatgttag tgcgtatcta     480
atttatagtt ttaagtttac cttagtggtt agatcgtgtg acatgcgcag cgacgggaaa    540
acgacgccgc ctttttgtctg caaaggcatt tgacgctaac tacctgtaga gttctgaata    600
tcctgtgcac tctgaaaggg ggataat                                         627

<210> SEQ ID NO 30
<211> LENGTH: 528
```

<212> TYPE: DNA
<213> ORGANISM: Artificial
<220> FEATURE:
<223> OTHER INFORMATION: PHM18731 reference sequence

<400> SEQUENCE: 30

| | | | | | |
|---|---|---|---|---|---|
| cccgggtagc | tcccagtcac | gacgaggagt | acgtcgcctc | tcatcccggc | tctcgcctct | 60 |
| cgctccccag | ccatccatgg | cgatgccacc | gagccgttcg | tgggcggagc | tgcagcacga | 120 |
| cctcctggtg | tcgatcatga | cccgcgtggg | cgcgccggac | ctcctctggg | gcggcgcttc | 180 |
| ccgcgcctgc | tcttcgtggc | gggccgcggc | gcgggaccca | ctcgcgtggc | gacgcgtcga | 240 |
| cctccgcgac | tgggtcgccc | tcacctccgg | ccggcgcgcc | gcgagacctg | gacactccag | 300 |
| ctctcgcgta | cccgtccacg | ccgcgctcgt | cggcatcctg | gaggtcgccg | ccaagttggc | 360 |
| cgaagggcgg | atcgaggccg | tgctgctccc | cgagtttgct | gatgaggacc | atctcttgtt | 420 |
| cctcgctgag | aggtgaaatc | ttctcccctgt | cccttttgaac | ttggctggct | gttccaggtg | 480 |
| ggaaatgccc | gttaccttta | gtgcacaatt | ttaaaaaaac | atttaaaa | | 528 |

<210> SEQ ID NO 31
<211> LENGTH: 548
<212> TYPE: DNA
<213> ORGANISM: Artificial
<220> FEATURE:
<223> OTHER INFORMATION: PHM2189 reference sequence

<400> SEQUENCE: 31

| | | | | | |
|---|---|---|---|---|---|
| ccwcgagatc | gattgcaagg | aagggcagga | gatcatggac | ctggccgacc | tgtccacgcc | 60 |
| cctcccggag | tggttcaccg | aggaggacct | ggacgcctac | gccaagctct | acgagaagtc | 120 |
| cggcttcggg | tacccgctca | agatgccgta | caggtagcca | ctcctttcgc | cggccaaacg | 180 |
| gcagatctct | ctgatgttca | ttaattgctt | cttggctttt | ccatgggaaa | atttgattgc | 240 |
| gcagatctat | gcacaagctc | ccgaaccggc | tggacgccaa | gttccaggtt | tcgatgtggt | 300 |
| gccggtgttc | ccgttttcaa | agtggtgatg | ggggagaagg | actacgcgtt | caagttcccg | 360 |
| gggttcgaga | ccgccatgcg | cggcggcgtc | atggacaact | tcatgccgga | cctcaagatc | 420 |
| acctacatcc | ctgagggggag | ccacttcgtg | caggagcagc | tccagagca | ggtcaacgac | 480 |
| ctgctcctcg | gcttcctcag | ggaccatccc | tccgccgcat | aagcagcgtt | ttaaaatggt | 540 |
| tatagctt | | | | | | 548 |

<210> SEQ ID NO 32
<211> LENGTH: 552
<212> TYPE: DNA
<213> ORGANISM: Artificial
<220> FEATURE:
<223> OTHER INFORMATION: PHM7734 reference sequence

<400> SEQUENCE: 32

| | | | | | |
|---|---|---|---|---|---|
| agtcgtcccc | cggttgtctg | ggtttctctg | caccgggtga | tgcttttcat | gaagggcact | 60 |
| ccagatgctc | ctcgttgcgg | cttcagttcg | aaggttgtga | acgccttgaa | gaaggaaggg | 120 |
| gtcagctttg | ggtccttcga | catcttatct | gacgaggaag | ttaggcaagg | tttgaagacg | 180 |
| tactccaact | ggcctacctt | cccccagctc | tactacaaat | cggagctgat | tggggatgt | 240 |
| gatatcgttc | ttgagatgga | gaagagcgga | gagctgaagt | cgaccctgtc | agagtagaca | 300 |
| cctagctagc | attcttgctt | cgctggcgtt | tttatcacat | tgcctgcatt | ggatcactct | 360 |
| actctggtat | tcatgccatt | gtattcatag | atccacgttg | gtacttgtct | gcagtgccac | 420 |

```
attgctagaa ttgtgacaca tctgcagaag gaataactta cgcttgttca cgcttgttcg      480
gtactgattg cattgttctt atatcaccag ttctatttag cgggtggaag catggtcata      540
gctgttcctt cc                                                          552

<210> SEQ ID NO 33
<211> LENGTH: 714
<212> TYPE: DNA
<213> ORGANISM: Artificial
<220> FEATURE:
<223> OTHER INFORMATION: PHM3323 reference sequence

<400> SEQUENCE: 33
caggttagtc catttatcgg taagttcaaa aaacaagtat ccttggccga tttagttagg       60
ggggacttct ggtaaaatat ttagccgtgg gctctaaatt tttgtagtct gtaaaaacca      120
caagaacata tgtatcatga ttatcttgtt actacagaag tgcatactaa ctaatggcat      180
tgggttcact aattccttgt tgccaaccag tgtgattgtg ggtgccgagt ccttaacctt      240
ctcacggagg ttatcagaag cgcagaagca acaggatgag caggacgatg atgaaggcac      300
tatcgctttc agtaagaact ggctgtctga aaataagaaa cccaagtatg ttctggctta      360
cctctttttt tttcccatta cttggcgtgg aaaacacata atcatactgt tgttcggtgt      420
gcagaacccc aaaggaggat aaaaagcgac cccgggagga tgatgatgtc gcgactgagg      480
aggatcgggt tgaggatttg gtcttgagct cagatgaaga ggatggcaac aatgaggaag      540
cagacgatgg ttttgttccg gttgaaggtg atagtgatga agactttgta gaccctgaca      600
gcgaatataa gaaacaaaag aaggcgaagc tgaagaagag gaacaagcgc cagccatttc      660
tgcacaaggc gccctctaga acaaaaagta attcagccca aaatttgggg aata            714

<210> SEQ ID NO 34
<211> LENGTH: 519
<212> TYPE: DNA
<213> ORGANISM: Artificial
<220> FEATURE:
<223> OTHER INFORMATION: PHM4736 reference sequence

<400> SEQUENCE: 34
tccaaccccc gggggctccc cccggggcag caacacacgc tcatctattc atgtgagtga       60
ggattgcacc atgcctgcat atcaagaacg ccacaaattc atttgaatag cggcgatacg      120
actcactgat ctgaagatgg ttctcctgcc cagattcata atggctaggc cagcaaccat      180
cttgagtctt ggccacaatt tttgcatcgt tgcagatgta gacatgccct attcatacag      240
gactcttaat tttagagaga gaaaaaaaat ctgaagagga ttgtttgaca cgtttcacct      300
tccagtttgc cttggagcaa ccgggttaga ctggctgtgt atgcctctgt atagagtgag      360
ttgtatcata catcagggta tcggaaatca gaaagtaggt tcagttcctg tgtcatctct      420
tttctgcttt atgttgtctg cccttctatt ttgagctagc tttgaagtgg catttcattg      480
taccatatcc atggtcatag ctgtccctac ccctacctc                             519

<210> SEQ ID NO 35
<211> LENGTH: 495
<212> TYPE: DNA
<213> ORGANISM: Artificial
<220> FEATURE:
<223> OTHER INFORMATION: PHM6441 reference sequence

<400> SEQUENCE: 35
gggaaggtcc cagtcacaac gggaaaagta aatgccgtta tgttttttcat ccagcaacca      60
```

```
agtgcaagaa tggctggagt tggaccatca gttgagcgaa cagacaaagc ctccggtacc    120
gctcctggta gttaatctca tttgacccat tgctatgtga aaaactagtc aatttaccta    180
attagttgtg ttttcgccag tgggacaaga ggcccgggac agattcacgg gtgctgttga    240
ggcattcgcc agaagaaatc caggctctgg tcgccatgga gatcattcca ggcaccaaag    300
ccttgcagat tcctttggca catccaacga agcagtaagt atccgattta gctcttgtag    360
cgtaataagc atccggttta gctgtgttag ctagtaaaca tgaatggtcg aatggagata    420 tacactttt  aaacgaaaaa tatgcactaa attgaaaatg agtgcagtaa atgaaaaggt    480
ctacttcctt taaat                                                    495
```

```
<210> SEQ ID NO 36
<211> LENGTH: 671
<212> TYPE: DNA
<213> ORGANISM: Artificial
<220> FEATURE:
<223> OTHER INFORMATION: PHM430 reference sequence

<400> SEQUENCE: 36
aggtaaacct ggaaaaggtt ttttcgttac caaacatgcg gggttaccgt ccccaagggc     60
tgcggtgagt ataatagctt tagctgggca tggccaatga tcatttgaga cgacaatga    120 catgctggcc cgctcacagt agcagccaga gagggtcctg catgtcgatg tcagtcagct    180
catgctccac gtggcgtgat catggtggaa taatattcta tcatcaatca gacaagtaaa    240
cagacaggga tatttacaag catatgaaaa caacctactc agcagcaact catgtgaaga    300
tcaagacttg cttacctgtg acctgatgac ttttaccac tgcacctgca caaaaaataa     360
accgttagat ttttagatct caggtagtta tgggctatat acatagatta agcattatag    420
atctcgtctg ttaccatcgc ttttactgcc ctcatttcgt gtcccttcca ctgcaggatc    480
aaagcaggac tgaagagcgg ctgaatctga atggagcaag ttggctaaca tacgcacggc    540
agctacaaat acttatagga ataaataaag ttggtcaact gttggtttca tggtgttgga    600
gtacaacaac tgtactgttc ttatcctcat atatgaactc tagtcatcac ataataattt    660
gggaaccgrg g                                                        671
```

```
<210> SEQ ID NO 37
<211> LENGTH: 512
<212> TYPE: DNA
<213> ORGANISM: Artificial
<220> FEATURE:
<223> OTHER INFORMATION: PHM12224 reference sequence

<400> SEQUENCE: 37
ccgctccccc ccgtttcgtt gttagatatg tagaaatata gaacttatat ctacacgagt     60
agataactcc taaataaat  taatctttta tcagattgct atcttctgga tttacaggaa    120
tccatatacc cctaaggtca atgaaaagag catgtataca cctttggtgt cgtgcttctt    180
gagcttgtca tcggaaagaa gccagtaggt gagttttggg acgacgtcaa cattgtccat    240
cgagtcaagt cgatgacaaa cacaaacaag gcgctgatct agatcattgg cctgaggctg    300
tcgaccgtgc acacaaggtc atgcatatat tctgtgtcgc acttctctgc gtcaaggagc    360
agagcatgca tcgacctatg atgtagaagg tggtgcagat gcacagcgaa cttcccaatc    420
cagatgcagg caaggagatg aggttctcgg tagcgatgat ttttccactg cacaattgga    480
ttcatggtca tagctgccct ccccccctcca at                                 512
```

```
<210> SEQ ID NO 38
<211> LENGTH: 465
<212> TYPE: DNA
<213> ORGANISM: Artificial
<220> FEATURE:
<223> OTHER INFORMATION: PHM11904 reference sequence

<400> SEQUENCE: 38
tctgcgcgcc cccatctga tagaatactg gtccactgaa aactatccag aaacgactag     60
cctaacattt gactggcagg aagatgtgga cttgattaag gacattggca tggatgcata    120
ccggttctct atctcgtggt cacgtatctt tccaagtatg taataagaaa attctttgta    180 aaatatttt ctttctttt agcactagat actagtacca catagtttat tatttttctt     240
gctagatgga actggtgaac ctaatgaaga aggattgaat tactataaca gcctcataaa    300
tactctatta gacaaaggta tttcatcttc tcaaatgtga gtcgttgtca actctcagtt    360
tgtgattatc tttctttgat tttatctata tttgtggggc caggtataca accatatgta    420
acactctttc actgggactt tcatggtcat agctgacctt ccctc                    465

<210> SEQ ID NO 39
<211> LENGTH: 493
<212> TYPE: DNA
<213> ORGANISM: Artificial
<220> FEATURE:
<223> OTHER INFORMATION: PHM6727 reference sequence

<400> SEQUENCE: 39
cggaaaacac aaatgaaatc gggaaaggtc caagtcacga cgtttctcta ttgcaaatca     60
tggttgcaag ttagacgtgt ttacctcaga tcttttcctc cagagacatt gggtatctct    120
tttctcatag tggactacat ttctccccct cgaagtcaat atctctttct tcgacttttc    180
attgctggca gttctgcgca tgtcctaaat ccttgaatca tagtaggaca tccatgacag    240
atcacataaa caacacggcc aatacatcac tgggcagttg ggcctcggct cctatcgccg    300
tcatctaact accatctagg gaatcaggaa tggtcctgcc gtgcaagcaa acctttaacg    360
ttccccatgg gataagcatg tgactatgca aatgcccgac acaaattata tcttattatg    420
gttaagaatc ttgtgtttat tttctcttct cctttttatt ttcattatta ttattaaatt    480
tatttaaatt att                                                       493

<210> SEQ ID NO 40
<211> LENGTH: 20
<212> TYPE: DNA
<213> ORGANISM: artificial
<220> FEATURE:
<223> OTHER INFORMATION: PHM654 internal forward primer

<400> SEQUENCE: 40
ttgcccggtt ccaattcgta                                                 20

<210> SEQ ID NO 41
<211> LENGTH: 22
<212> TYPE: DNA
<213> ORGANISM: artificial
<220> FEATURE:
<223> OTHER INFORMATION: PHM654 internal reverse primer

<400> SEQUENCE: 41
catcagaaca tttatagtcc gt                                              22
```

```
<210> SEQ ID NO 42
<211> LENGTH: 21
<212> TYPE: DNA
<213> ORGANISM: artificial
<220> FEATURE:
<223> OTHER INFORMATION: PHM654 external forward primer

<400> SEQUENCE: 42
atgtccttta ttcgccggac t                                              21

<210> SEQ ID NO 43
<211> LENGTH: 21
<212> TYPE: DNA
<213> ORGANISM: artificial
<220> FEATURE:
<223> OTHER INFORMATION: PHM654 external reverse primer

<400> SEQUENCE: 43
agttaccgaa atccagtgtg a                                              21

<210> SEQ ID NO 44
<211> LENGTH: 19
<212> TYPE: DNA
<213> ORGANISM: artificial
<220> FEATURE:
<223> OTHER INFORMATION: PHM111 internal forward primer

<400> SEQUENCE: 44
cactctgcca aaggacgag                                                 19

<210> SEQ ID NO 45
<211> LENGTH: 18
<212> TYPE: DNA
<213> ORGANISM: artificial
<220> FEATURE:
<223> OTHER INFORMATION: PHM111 internal reverse primer

<400> SEQUENCE: 45
cagaagtgcc cgccgctg                                                  18

<210> SEQ ID NO 46
<211> LENGTH: 22
<212> TYPE: DNA
<213> ORGANISM: artificial
<220> FEATURE:
<223> OTHER INFORMATION: PHM111 external forward primer

<400> SEQUENCE: 46
cagatcgaag tcaagtttga ta                                             22

<210> SEQ ID NO 47
<211> LENGTH: 20
<212> TYPE: DNA
<213> ORGANISM: artificial
<220> FEATURE:
<223> OTHER INFORMATION: PHM111 external reverse primer

<400> SEQUENCE: 47
aacaaatctc tccctcgcgg                                                20

<210> SEQ ID NO 48
<211> LENGTH: 22
<212> TYPE: DNA
<213> ORGANISM: artificial
<220> FEATURE:
<223> OTHER INFORMATION: PHM10100 internal forward primer
```

```
<400> SEQUENCE: 48
ctcagtgatt gtttgtcatt gt                                              22

<210> SEQ ID NO 49
<211> LENGTH: 21
<212> TYPE: DNA
<213> ORGANISM: artificial
<220> FEATURE:
<223> OTHER INFORMATION: PHM10100 internal reverse primer

<400> SEQUENCE: 49
atccaatgag cggcagaaag a                                               21

<210> SEQ ID NO 50
<211> LENGTH: 20
<212> TYPE: DNA
<213> ORGANISM: artificial
<220> FEATURE:
<223> OTHER INFORMATION: PHM10100 external forward primer

<400> SEQUENCE: 50
ctactactct gcctgttggt                                                 20

<210> SEQ ID NO 51
<211> LENGTH: 21
<212> TYPE: DNA
<213> ORGANISM: artificial
<220> FEATURE:
<223> OTHER INFORMATION: PHM10100 external reverse primer

<400> SEQUENCE: 51
gtcgttcctc gaacattcac a                                               21

<210> SEQ ID NO 52
<211> LENGTH: 22
<212> TYPE: DNA
<213> ORGANISM: artificial
<220> FEATURE:
<223> OTHER INFORMATION: PHM7357 internal forward primer

<400> SEQUENCE: 52
ctgatgttta atcattacaa ag                                              22

<210> SEQ ID NO 53
<211> LENGTH: 22
<212> TYPE: DNA
<213> ORGANISM: artificial
<220> FEATURE:
<223> OTHER INFORMATION: PHM7357 internal reverse primer

<400> SEQUENCE: 53
tcatcacaga agaatgttta gg                                              22

<210> SEQ ID NO 54
<211> LENGTH: 22
<212> TYPE: DNA
<213> ORGANISM: artificial
<220> FEATURE:
<223> OTHER INFORMATION: PHM7357 external forward primer

<400> SEQUENCE: 54
tttcataata ccaacaactc ta                                              22

<210> SEQ ID NO 55
<211> LENGTH: 20
```

```
<212> TYPE: DNA
<213> ORGANISM: artificial
<220> FEATURE:
<223> OTHER INFORMATION: PHM7357 external reverse primer

<400> SEQUENCE: 55
ttgagtgccc tctaacttca                                            20

<210> SEQ ID NO 56
<211> LENGTH: 22
<212> TYPE: DNA
<213> ORGANISM: artificial
<220> FEATURE:
<223> OTHER INFORMATION: PHM5349 internal forward primer

<400> SEQUENCE: 56
taagcttgat agcgcaaaat cg                                         22

<210> SEQ ID NO 57
<211> LENGTH: 22
<212> TYPE: DNA
<213> ORGANISM: artificial
<220> FEATURE:
<223> OTHER INFORMATION: PHM5349 internal reverse primer

<400> SEQUENCE: 57
aaacaaaagg tgagcagtac aa                                         22

<210> SEQ ID NO 58
<211> LENGTH: 20
<212> TYPE: DNA
<213> ORGANISM: artificial
<220> FEATURE:
<223> OTHER INFORMATION: PHM5349 external forward primer

<400> SEQUENCE: 58
tgctgaacgc gctttgttct                                            20

<210> SEQ ID NO 59
<211> LENGTH: 21
<212> TYPE: DNA
<213> ORGANISM: artificial
<220> FEATURE:
<223> OTHER INFORMATION: PHM5349 external reverse primer

<400> SEQUENCE: 59
tttgtgaact gccatgactc a                                          21

<210> SEQ ID NO 60
<211> LENGTH: 21
<212> TYPE: DNA
<213> ORGANISM: artificial
<220> FEATURE:
<223> OTHER INFORMATION: PHM4167 internal forward primer

<400> SEQUENCE: 60
gaggaaattt cagtgtgcaa c                                          21

<210> SEQ ID NO 61
<211> LENGTH: 20
<212> TYPE: DNA
<213> ORGANISM: artificial
<220> FEATURE:
<223> OTHER INFORMATION: PHM4167 internal reverse primer

<400> SEQUENCE: 61
```
tctacactcg ttgtgaccag                                              20

<210> SEQ ID NO 62
<211> LENGTH: 21
<212> TYPE: DNA
<213> ORGANISM: artificial
<220> FEATURE:
<223> OTHER INFORMATION: PHM4167 external forward primer

<400> SEQUENCE: 62
attggtgtgt ttgatgccct t                                            21

<210> SEQ ID NO 63
<211> LENGTH: 21
<212> TYPE: DNA
<213> ORGANISM: artificial
<220> FEATURE:
<223> OTHER INFORMATION: PHM4167 external reverse primer

<400> SEQUENCE: 63
tccctcaaac gtgtgatgaa g                                            21

<210> SEQ ID NO 64
<211> LENGTH: 18
<212> TYPE: DNA
<213> ORGANISM: artificial
<220> FEATURE:
<223> OTHER INFORMATION: PHM14947 internal forward primer

<400> SEQUENCE: 64
cgtcagggac ccggtgta                                                18

<210> SEQ ID NO 65
<211> LENGTH: 20
<212> TYPE: DNA
<213> ORGANISM: artificial
<220> FEATURE:
<223> OTHER INFORMATION: PHM14947 internal reverse primer

<400> SEQUENCE: 65
acgtacgctc gccttccatt                                              20

<210> SEQ ID NO 66
<211> LENGTH: 18
<212> TYPE: DNA
<213> ORGANISM: artificial
<220> FEATURE:
<223> OTHER INFORMATION: PHM14947 external forward primer

<400> SEQUENCE: 66
tgtacgaggc caacgcgc                                                18

<210> SEQ ID NO 67
<211> LENGTH: 21
<212> TYPE: DNA
<213> ORGANISM: artificial
<220> FEATURE:
<223> OTHER INFORMATION: PHM14947 external reverse primer

<400> SEQUENCE: 67
ctggacatac tggtagaagg t                                            21

<210> SEQ ID NO 68
<211> LENGTH: 22
<212> TYPE: DNA
<213> ORGANISM: artificial

```
<220> FEATURE:
<223> OTHER INFORMATION: PHM5266 internal forward primer

<400> SEQUENCE: 68
taccttacac attgctaggg ta                                             22

<210> SEQ ID NO 69
<211> LENGTH: 22
<212> TYPE: DNA
<213> ORGANISM: artificial
<220> FEATURE:
<223> OTHER INFORMATION: PHM5266 internal reverse primer

<400> SEQUENCE: 69
ttgacatttc tgtacaggac tg                                             22

<210> SEQ ID NO 70
<211> LENGTH: 21
<212> TYPE: DNA
<213> ORGANISM: artificial
<220> FEATURE:
<223> OTHER INFORMATION: PHM5266 external forward primer

<400> SEQUENCE: 70
tctccagaga ttcatgcgaa g                                              21

<210> SEQ ID NO 71
<211> LENGTH: 21
<212> TYPE: DNA
<213> ORGANISM: artificial
<220> FEATURE:
<223> OTHER INFORMATION: PHM5266 external reverse primer

<400> SEQUENCE: 71
aatgtgcaca atctgctgtg a                                              21

<210> SEQ ID NO 72
<211> LENGTH: 22
<212> TYPE: DNA
<213> ORGANISM: artificial
<220> FEATURE:
<223> OTHER INFORMATION: PHM12632 internal forward primer

<400> SEQUENCE: 72
catgtatttc ttacaggtta gc                                             22

<210> SEQ ID NO 73
<211> LENGTH: 22
<212> TYPE: DNA
<213> ORGANISM: artificial
<220> FEATURE:
<223> OTHER INFORMATION: PHM12632 internal reverse primer

<400> SEQUENCE: 73
aacctataat tcaggatgga ga                                             22

<210> SEQ ID NO 74
<211> LENGTH: 22
<212> TYPE: DNA
<213> ORGANISM: artificial
<220> FEATURE:
<223> OTHER INFORMATION: PHM12632 external forward primer

<400> SEQUENCE: 74
attagcttta ttgttgcaag tg                                             22
```

```
<210> SEQ ID NO 75
<211> LENGTH: 22
<212> TYPE: DNA
<213> ORGANISM: artificial
<220> FEATURE:
<223> OTHER INFORMATION: PHM12632 external reverse primer

<400> SEQUENCE: 75
ccgttccaaa ttagatgtca tt                                              22

<210> SEQ ID NO 76
<211> LENGTH: 21
<212> TYPE: DNA
<213> ORGANISM: artificial
<220> FEATURE:
<223> OTHER INFORMATION: PHM201 internal forward primer

<400> SEQUENCE: 76
gattctcgtg tgaccatgaa t                                               21

<210> SEQ ID NO 77
<211> LENGTH: 21
<212> TYPE: DNA
<213> ORGANISM: artificial
<220> FEATURE:
<223> OTHER INFORMATION: PHM201 internal reverse primer

<400> SEQUENCE: 77
gaagatactc tgaaaacact t                                               21

<210> SEQ ID NO 78
<211> LENGTH: 22
<212> TYPE: DNA
<213> ORGANISM: artificial
<220> FEATURE:
<223> OTHER INFORMATION: PHM201 external forward primer

<400> SEQUENCE: 78
atgacatgtg atgtgaaggt ca                                              22

<210> SEQ ID NO 79
<211> LENGTH: 20
<212> TYPE: DNA
<213> ORGANISM: artificial
<220> FEATURE:
<223> OTHER INFORMATION: PHM201 external reverse primer

<400> SEQUENCE: 79
agccttctca tcatcgcaca                                                 20

<210> SEQ ID NO 80
<211> LENGTH: 20
<212> TYPE: DNA
<213> ORGANISM: artificial
<220> FEATURE:
<223> OTHER INFORMATION: PHM4861 internal forward primer

<400> SEQUENCE: 80
ctgctgggtg ttcttgtgta                                                 20

<210> SEQ ID NO 81
<211> LENGTH: 22
<212> TYPE: DNA
<213> ORGANISM: artificial
<220> FEATURE:
<223> OTHER INFORMATION: PHM4861 internal reverse primer
```

-continued

```
<400> SEQUENCE: 81
caataggtcc tttaaatgcc ct                                      22

<210> SEQ ID NO 82
<211> LENGTH: 21
<212> TYPE: DNA
<213> ORGANISM: artificial
<220> FEATURE:
<223> OTHER INFORMATION: PHM4861 external forward primer

<400> SEQUENCE: 82
atgtgttctt cagtggtgac a                                       21

<210> SEQ ID NO 83
<211> LENGTH: 20
<212> TYPE: DNA
<213> ORGANISM: artificial
<220> FEATURE:
<223> OTHER INFORMATION: PHM4861 external reverse primer

<400> SEQUENCE: 83
tttgccgtcc gtgtactgtt                                         20

<210> SEQ ID NO 84
<211> LENGTH: 18
<212> TYPE: DNA
<213> ORGANISM: artificial
<220> FEATURE:
<223> OTHER INFORMATION: PHM5421 internal forward primer

<400> SEQUENCE: 84
acgactgggt gactgccg                                           18

<210> SEQ ID NO 85
<211> LENGTH: 22
<212> TYPE: DNA
<213> ORGANISM: artificial
<220> FEATURE:
<223> OTHER INFORMATION: PHM5421 internal reverse primer

<400> SEQUENCE: 85
taaataggtt tgagtcaaat cg                                      22

<210> SEQ ID NO 86
<211> LENGTH: 19
<212> TYPE: DNA
<213> ORGANISM: artificial
<220> FEATURE:
<223> OTHER INFORMATION: PHM5421 external forward primer

<400> SEQUENCE: 86
gcgctcttct ctctctcgt                                          19

<210> SEQ ID NO 87
<211> LENGTH: 22
<212> TYPE: DNA
<213> ORGANISM: artificial
<220> FEATURE:
<223> OTHER INFORMATION: PHM5421 external reverse primer

<400> SEQUENCE: 87
tttatcattg attagttctg cg                                      22

<210> SEQ ID NO 88
```

```
<211> LENGTH: 22
<212> TYPE: DNA
<213> ORGANISM: artificial
<220> FEATURE:
<223> OTHER INFORMATION: PHM4115 internal forward primer

<400> SEQUENCE: 88
ttgtaatcgt tggtgaagag aa                                              22

<210> SEQ ID NO 89
<211> LENGTH: 21
<212> TYPE: DNA
<213> ORGANISM: artificial
<220> FEATURE:
<223> OTHER INFORMATION: PHM4115 internal reverse primer

<400> SEQUENCE: 89
tcacgttaca acagttggag a                                               21

<210> SEQ ID NO 90
<211> LENGTH: 20
<212> TYPE: DNA
<213> ORGANISM: artificial
<220> FEATURE:
<223> OTHER INFORMATION: PHM4115 external forward primer

<400> SEQUENCE: 90
ataaaggaga cggcaagcca                                                 20

<210> SEQ ID NO 91
<211> LENGTH: 22
<212> TYPE: DNA
<213> ORGANISM: artificial
<220> FEATURE:
<223> OTHER INFORMATION: PHM4115 external reverse primer

<400> SEQUENCE: 91
aacacaaggc aacaacacaa ac                                              22

<210> SEQ ID NO 92
<211> LENGTH: 22
<212> TYPE: DNA
<213> ORGANISM: artificial
<220> FEATURE:
<223> OTHER INFORMATION: PHM12521 internal forward primer

<400> SEQUENCE: 92
gtcatagaca tgtaacactt ag                                              22

<210> SEQ ID NO 93
<211> LENGTH: 20
<212> TYPE: DNA
<213> ORGANISM: artificial
<220> FEATURE:
<223> OTHER INFORMATION: PHM12521 internal reverse primer

<400> SEQUENCE: 93
ctccgcctca tctttgtcaa                                                 20

<210> SEQ ID NO 94
<211> LENGTH: 22
<212> TYPE: DNA
<213> ORGANISM: artificial
<220> FEATURE:
<223> OTHER INFORMATION: PHM12521 external forward primer

<400> SEQUENCE: 94
```
cttcaaaatt caaagctccc tt                                    22

<210> SEQ ID NO 95
<211> LENGTH: 21
<212> TYPE: DNA
<213> ORGANISM: artificial
<220> FEATURE:
<223> OTHER INFORMATION: PHM12521 external reverse primer

<400> SEQUENCE: 95
ctgagaactt tgggttacct g                                     21

<210> SEQ ID NO 96
<211> LENGTH: 20
<212> TYPE: DNA
<213> ORGANISM: artificial
<220> FEATURE:
<223> OTHER INFORMATION: PHM3468 internal forward primer

<400> SEQUENCE: 96
tacctgcgga agctcgacct                                       20

<210> SEQ ID NO 97
<211> LENGTH: 21
<212> TYPE: DNA
<213> ORGANISM: artificial
<220> FEATURE:
<223> OTHER INFORMATION: PHM3468 internal reverse primer

<400> SEQUENCE: 97
ttagcttctg tgctgctgct a                                     21

<210> SEQ ID NO 98
<211> LENGTH: 21
<212> TYPE: DNA
<213> ORGANISM: artificial
<220> FEATURE:
<223> OTHER INFORMATION: PHM3468 external forward primer

<400> SEQUENCE: 98
ctcattcgtc aaggtgagca t                                     21

<210> SEQ ID NO 99
<211> LENGTH: 20
<212> TYPE: DNA
<213> ORGANISM: artificial
<220> FEATURE:
<223> OTHER INFORMATION: PHM3468 external reverse primer

<400> SEQUENCE: 99
agagctaagc cgaaacaacc                                       20

<210> SEQ ID NO 100
<211> LENGTH: 22
<212> TYPE: DNA
<213> ORGANISM: artificial
<220> FEATURE:
<223> OTHER INFORMATION: PHM10840 internal forward primer

<400> SEQUENCE: 100
tttccaagat gcagatggct at                                    22

<210> SEQ ID NO 101
<211> LENGTH: 20
<212> TYPE: DNA

```
<213> ORGANISM: artificial
<220> FEATURE:
<223> OTHER INFORMATION: PHM10840 internal reverse primer

<400> SEQUENCE: 101
tccgacaatt cgacctgcta                                              20

<210> SEQ ID NO 102
<211> LENGTH: 20
<212> TYPE: DNA
<213> ORGANISM: artificial
<220> FEATURE:
<223> OTHER INFORMATION: PHM10840 external forward primer

<400> SEQUENCE: 102
ggatcaaaga tcatgatgtg                                              20

<210> SEQ ID NO 103
<211> LENGTH: 22
<212> TYPE: DNA
<213> ORGANISM: artificial
<220> FEATURE:
<223> OTHER INFORMATION: PHM10840 external reverse primer

<400> SEQUENCE: 103
agttgttaca caacgagctg aa                                           22

<210> SEQ ID NO 104
<211> LENGTH: 19
<212> TYPE: DNA
<213> ORGANISM: artificial
<220> FEATURE:
<223> OTHER INFORMATION: PHM12755 internal forward primer

<400> SEQUENCE: 104
aggtcagccg cgacgacga                                               19

<210> SEQ ID NO 105
<211> LENGTH: 22
<212> TYPE: DNA
<213> ORGANISM: artificial
<220> FEATURE:
<223> OTHER INFORMATION: PHM12755 internal reverse primer

<400> SEQUENCE: 105
acatgacaag tgaaaccagt ag                                           22

<210> SEQ ID NO 106
<211> LENGTH: 19
<212> TYPE: DNA
<213> ORGANISM: artificial
<220> FEATURE:
<223> OTHER INFORMATION: PHM12755 external forward primer

<400> SEQUENCE: 106
gctcgcttct tcccagaga                                               19

<210> SEQ ID NO 107
<211> LENGTH: 20
<212> TYPE: DNA
<213> ORGANISM: artificial
<220> FEATURE:
<223> OTHER INFORMATION: PHM12755 external reverse primer

<400> SEQUENCE: 107
cgctggaaac atcaccaatg                                              20
```

<210> SEQ ID NO 108
<211> LENGTH: 19
<212> TYPE: DNA
<213> ORGANISM: artificial
<220> FEATURE:
<223> OTHER INFORMATION: PHM13879 internal forward primer

<400> SEQUENCE: 108
tgaccatcct gtaccagga                                          19

<210> SEQ ID NO 109
<211> LENGTH: 20
<212> TYPE: DNA
<213> ORGANISM: artificial
<220> FEATURE:
<223> OTHER INFORMATION: PHM13879 internal reverse primer

<400> SEQUENCE: 109
gacatggcaa tggcatggat                                         20

<210> SEQ ID NO 110
<211> LENGTH: 19
<212> TYPE: DNA
<213> ORGANISM: artificial
<220> FEATURE:
<223> OTHER INFORMATION: PHM13879 external forward primer

<400> SEQUENCE: 110
ctgaaccact accctccctt                                         19

<210> SEQ ID NO 111
<211> LENGTH: 20
<212> TYPE: DNA
<213> ORGANISM: artificial
<220> FEATURE:
<223> OTHER INFORMATION: PHM13879 external reverse primer

<400> SEQUENCE: 111
atggcgtgct ctgaatctga                                         20

<210> SEQ ID NO 112
<211> LENGTH: 21
<212> TYPE: DNA
<213> ORGANISM: artificial
<220> FEATURE:
<223> OTHER INFORMATION: PHM4103 internal forward primer

<400> SEQUENCE: 112
aagaagaaac ccacagcaga a                                       21

<210> SEQ ID NO 113
<211> LENGTH: 21
<212> TYPE: DNA
<213> ORGANISM: artificial
<220> FEATURE:
<223> OTHER INFORMATION: PHM4103 internal reverse primer

<400> SEQUENCE: 113
tgcctgtaca tgcgacacat a                                       21

<210> SEQ ID NO 114
<211> LENGTH: 22
<212> TYPE: DNA
<213> ORGANISM: artificial
<220> FEATURE:

<223> OTHER INFORMATION: PHM4103 external forward primer

<400> SEQUENCE: 114
agtatcatcc aagattcacg ag                                              22

<210> SEQ ID NO 115
<211> LENGTH: 21
<212> TYPE: DNA
<213> ORGANISM: artificial
<220> FEATURE:
<223> OTHER INFORMATION: PHM4103 external reverse primer

<400> SEQUENCE: 115
gttctcaagt tggtggctga a                                               21

<210> SEQ ID NO 116
<211> LENGTH: 20
<212> TYPE: DNA
<213> ORGANISM: artificial
<220> FEATURE:
<223> OTHER INFORMATION: PHM5363 internal forward primer

<400> SEQUENCE: 116
atctacccgg acgagaacat                                                 20

<210> SEQ ID NO 117
<211> LENGTH: 22
<212> TYPE: DNA
<213> ORGANISM: artificial
<220> FEATURE:
<223> OTHER INFORMATION: PHM5363 internal reverse primer

<400> SEQUENCE: 117
ttacactggt ttgtatcaga gt                                              22

<210> SEQ ID NO 118
<211> LENGTH: 19
<212> TYPE: DNA
<213> ORGANISM: artificial
<220> FEATURE:
<223> OTHER INFORMATION: PHM5363 external forward primer

<400> SEQUENCE: 118
aagccatggc agaagaagc                                                  19

<210> SEQ ID NO 119
<211> LENGTH: 22
<212> TYPE: DNA
<213> ORGANISM: artificial
<220> FEATURE:
<223> OTHER INFORMATION: PHM5363 external reverse primer

<400> SEQUENCE: 119
attgattgtg tggtacaatc ca                                              22

<210> SEQ ID NO 120
<211> LENGTH: 18
<212> TYPE: DNA
<213> ORGANISM: artificial
<220> FEATURE:
<223> OTHER INFORMATION: PHM14751 internal forward primer

<400> SEQUENCE: 120
atcatcaatc atccagag                                                   18

-continued

```
<210> SEQ ID NO 121
<211> LENGTH: 18
<212> TYPE: DNA
<213> ORGANISM: artificial
<220> FEATURE:
<223> OTHER INFORMATION: PHM14751 internal reverse primer

<400> SEQUENCE: 121
cggaaataga agaacttc                                                18

<210> SEQ ID NO 122
<211> LENGTH: 22
<212> TYPE: DNA
<213> ORGANISM: artificial
<220> FEATURE:
<223> OTHER INFORMATION: PHM14751 external forward primer

<400> SEQUENCE: 122
agacatgtgt gaatccaaca tt                                           22

<210> SEQ ID NO 123
<211> LENGTH: 21
<212> TYPE: DNA
<213> ORGANISM: artificial
<220> FEATURE:
<223> OTHER INFORMATION: PHM14751 external reverse primer

<400> SEQUENCE: 123
ctactcttga ggcttcatag c                                            21

<210> SEQ ID NO 124
<211> LENGTH: 19
<212> TYPE: DNA
<213> ORGANISM: artificial
<220> FEATURE:
<223> OTHER INFORMATION: PHM16138 internal forward primer

<400> SEQUENCE: 124
ggcgtgagct cggctacta                                               19

<210> SEQ ID NO 125
<211> LENGTH: 20
<212> TYPE: DNA
<213> ORGANISM: artificial
<220> FEATURE:
<223> OTHER INFORMATION: PHM16138 internal reverse primer

<400> SEQUENCE: 125
agcgcttcgt ccttggttat                                              20

<210> SEQ ID NO 126
<211> LENGTH: 19
<212> TYPE: DNA
<213> ORGANISM: artificial
<220> FEATURE:
<223> OTHER INFORMATION: PHM16138 external forward primer

<400> SEQUENCE: 126
agtgttcctg tacgcagca                                               19

<210> SEQ ID NO 127
<211> LENGTH: 21
<212> TYPE: DNA
<213> ORGANISM: artificial
<220> FEATURE:
<223> OTHER INFORMATION: PHM16138 external reverse primer
```

<400> SEQUENCE: 127
cgcaagcaat cttgagatac t                                          21

<210> SEQ ID NO 128
<211> LENGTH: 20
<212> TYPE: DNA
<213> ORGANISM: artificial
<220> FEATURE:
<223> OTHER INFORMATION: PHM7877 internal forward primer

<400> SEQUENCE: 128
atcgacgcca agcatgacaa                                            20

<210> SEQ ID NO 129
<211> LENGTH: 22
<212> TYPE: DNA
<213> ORGANISM: artificial
<220> FEATURE:
<223> OTHER INFORMATION: PHM7877 internal reverse primer

<400> SEQUENCE: 129
aaataacgct acactttcac tc                                         22

<210> SEQ ID NO 130
<211> LENGTH: 20
<212> TYPE: DNA
<213> ORGANISM: artificial
<220> FEATURE:
<223> OTHER INFORMATION: PHM7877 external forward primer

<400> SEQUENCE: 130
cgactacctg gacaagtttg                                            20

<210> SEQ ID NO 131
<211> LENGTH: 20
<212> TYPE: DNA
<213> ORGANISM: artificial
<220> FEATURE:
<223> OTHER INFORMATION: PHM7877 external reverse primer

<400> SEQUENCE: 131
tacggaccac atactcgctt                                            20

<210> SEQ ID NO 132
<211> LENGTH: 18
<212> TYPE: DNA
<213> ORGANISM: artificial
<220> FEATURE:
<223> OTHER INFORMATION: PHM9518 internal forward primer

<400> SEQUENCE: 132
gaagtggcca ggtccagc                                              18

<210> SEQ ID NO 133
<211> LENGTH: 19
<212> TYPE: DNA
<213> ORGANISM: artificial
<220> FEATURE:
<223> OTHER INFORMATION: PHM9518 internal reverse primer

<400> SEQUENCE: 133
tggagtgcta gagcagtcc                                             19

<210> SEQ ID NO 134
<211> LENGTH: 20

```
<212> TYPE: DNA
<213> ORGANISM: artificial
<220> FEATURE:
<223> OTHER INFORMATION: PHM9518 external forward primer

<400> SEQUENCE: 134
ctgttgccat cattgcagtg                                            20

<210> SEQ ID NO 135
<211> LENGTH: 22
<212> TYPE: DNA
<213> ORGANISM: artificial
<220> FEATURE:
<223> OTHER INFORMATION: PHM9518 external reverse primer

<400> SEQUENCE: 135
tacgatcagt atagcaagaa ac                                         22

<210> SEQ ID NO 136
<211> LENGTH: 20
<212> TYPE: DNA
<213> ORGANISM: artificial
<220> FEATURE:
<223> OTHER INFORMATION: PHM7802 internal forward primer

<400> SEQUENCE: 136
aacgtcggct gctactacat                                            20

<210> SEQ ID NO 137
<211> LENGTH: 20
<212> TYPE: DNA
<213> ORGANISM: artificial
<220> FEATURE:
<223> OTHER INFORMATION: PHM7802 internal reverse primer

<400> SEQUENCE: 137
atttggcctg gttctgtcca                                            20

<210> SEQ ID NO 138
<211> LENGTH: 20
<212> TYPE: DNA
<213> ORGANISM: artificial
<220> FEATURE:
<223> OTHER INFORMATION: PHM7802 external forward primer

<400> SEQUENCE: 138
cgggactaca tcagctacat                                            20

<210> SEQ ID NO 139
<211> LENGTH: 20
<212> TYPE: DNA
<213> ORGANISM: artificial
<220> FEATURE:
<223> OTHER INFORMATION: PHM7802 external reverse primer

<400> SEQUENCE: 139
agccatctgg ttctgtccat                                            20

<210> SEQ ID NO 140
<211> LENGTH: 20
<212> TYPE: DNA
<213> ORGANISM: artificial
<220> FEATURE:
<223> OTHER INFORMATION: PHM2134 internal forward primer

<400> SEQUENCE: 140
```

```
gtccatatgg agagcttctc                                              20

<210> SEQ ID NO 141
<211> LENGTH: 19
<212> TYPE: DNA
<213> ORGANISM: artificial
<220> FEATURE:
<223> OTHER INFORMATION: PHM2134 internal reverse primer

<400> SEQUENCE: 141
acacaagcaa ccgccgcaa                                               19

<210> SEQ ID NO 142
<211> LENGTH: 21
<212> TYPE: DNA
<213> ORGANISM: artificial
<220> FEATURE:
<223> OTHER INFORMATION: PHM2134 external forward primer

<400> SEQUENCE: 142
cgatccgaac aatactactg t                                            21

<210> SEQ ID NO 143
<211> LENGTH: 21
<212> TYPE: DNA
<213> ORGANISM: artificial
<220> FEATURE:
<223> OTHER INFORMATION: PHM2134 external reverse primer

<400> SEQUENCE: 143
tcataaggcc tcggcaaaaa t                                            21

<210> SEQ ID NO 144
<211> LENGTH: 20
<212> TYPE: DNA
<213> ORGANISM: artificial
<220> FEATURE:
<223> OTHER INFORMATION: PHM7808 internal forward primer

<400> SEQUENCE: 144
aatggtggag ctgcttcgaa                                              20

<210> SEQ ID NO 145
<211> LENGTH: 21
<212> TYPE: DNA
<213> ORGANISM: artificial
<220> FEATURE:
<223> OTHER INFORMATION: PHM7808 internal reverse primer

<400> SEQUENCE: 145
gaagcctcca tgcaaactga t                                            21

<210> SEQ ID NO 146
<211> LENGTH: 20
<212> TYPE: DNA
<213> ORGANISM: artificial
<220> FEATURE:
<223> OTHER INFORMATION: PHM7808 external forward primer

<400> SEQUENCE: 146
tttctgctgg gagtgacaca                                              20

<210> SEQ ID NO 147
<211> LENGTH: 21
<212> TYPE: DNA
<213> ORGANISM: artificial
```

```
<220> FEATURE:
<223> OTHER INFORMATION: PHM7808 external reverse primer

<400> SEQUENCE: 147
tggtcaacgt gatgccgaaa t                                              21

<210> SEQ ID NO 148
<211> LENGTH: 20
<212> TYPE: DNA
<213> ORGANISM: artificial
<220> FEATURE:
<223> OTHER INFORMATION: PHM9627 internal forward primer

<400> SEQUENCE: 148
tttctgaccg ggaccaggat                                                20

<210> SEQ ID NO 149
<211> LENGTH: 18
<212> TYPE: DNA
<213> ORGANISM: artificial
<220> FEATURE:
<223> OTHER INFORMATION: PHM9627 internal reverse primer

<400> SEQUENCE: 149
ttgaacaacc gccgcgcg                                                  18

<210> SEQ ID NO 150
<211> LENGTH: 20
<212> TYPE: DNA
<213> ORGANISM: artificial
<220> FEATURE:
<223> OTHER INFORMATION: PHM9627 external forward primer

<400> SEQUENCE: 150
cggtagacca gacctcaata                                                20

<210> SEQ ID NO 151
<211> LENGTH: 20
<212> TYPE: DNA
<213> ORGANISM: artificial
<220> FEATURE:
<223> OTHER INFORMATION: PHM9627 external reverse primer

<400> SEQUENCE: 151
tcttgctgca ttcctgctac                                                20

<210> SEQ ID NO 152
<211> LENGTH: 19
<212> TYPE: DNA
<213> ORGANISM: artificial
<220> FEATURE:
<223> OTHER INFORMATION: PHMPHM13716 internal forward primer

<400> SEQUENCE: 152
ctccagaagc cattcagag                                                 19

<210> SEQ ID NO 153
<211> LENGTH: 20
<212> TYPE: DNA
<213> ORGANISM: artificial
<220> FEATURE:
<223> OTHER INFORMATION: PHM13716 internal reverse primer

<400> SEQUENCE: 153
acacaagagt gcaacaggat                                                20
```

<210> SEQ ID NO 154
<211> LENGTH: 19
<212> TYPE: DNA
<213> ORGANISM: artificial
<220> FEATURE:
<223> OTHER INFORMATION: PHM13716 external forward primer

<400> SEQUENCE: 154
agcagcaaga ctcagggat                                                    19

<210> SEQ ID NO 155
<211> LENGTH: 19
<212> TYPE: DNA
<213> ORGANISM: artificial
<220> FEATURE:
<223> OTHER INFORMATION: PHM13716 external reverse primer

<400> SEQUENCE: 155
cattttcgag cattaaagc                                                    19

<210> SEQ ID NO 156
<211> LENGTH: 20
<212> TYPE: DNA
<213> ORGANISM: artificial
<220> FEATURE:
<223> OTHER INFORMATION: PHM18731 internal forward primer

<400> SEQUENCE: 156
aggagtacgt cgcctctcat                                                   20

<210> SEQ ID NO 157
<211> LENGTH: 22
<212> TYPE: DNA
<213> ORGANISM: artificial
<220> FEATURE:
<223> OTHER INFORMATION: PHM18731 internal reverse primer

<400> SEQUENCE: 157
aggtgctaat taaaaggtca ac                                                22

<210> SEQ ID NO 158
<211> LENGTH: 22
<212> TYPE: DNA
<213> ORGANISM: artificial
<220> FEATURE:
<223> OTHER INFORMATION: PHM18731 external forward primer

<400> SEQUENCE: 158
aatgacattt acttcttcag tt                                                22

<210> SEQ ID NO 159
<211> LENGTH: 21
<212> TYPE: DNA
<213> ORGANISM: artificial
<220> FEATURE:
<223> OTHER INFORMATION: PHM18731 external reverse primer

<400> SEQUENCE: 159
cctactagta ccataaccta a                                                 21

<210> SEQ ID NO 160
<211> LENGTH: 19
<212> TYPE: DNA
<213> ORGANISM: artificial
<220> FEATURE:
<223> OTHER INFORMATION: PHM2189 internal forward primer -continued

<400> SEQUENCE: 160
ccgagatccc gattgccaa                                                        19

<210> SEQ ID NO 161
<211> LENGTH: 19
<212> TYPE: DNA
<213> ORGANISM: artificial
<220> FEATURE:
<223> OTHER INFORMATION: PHM2189 internal reverse primer

<400> SEQUENCE: 161
tctcacccgc tgcttatgc                                                        19

<210> SEQ ID NO 162
<211> LENGTH: 18
<212> TYPE: DNA
<213> ORGANISM: artificial
<220> FEATURE:
<223> OTHER INFORMATION: PHM2189 external forward primer

<400> SEQUENCE: 162
tcgacgccat catgcccg                                                         18

<210> SEQ ID NO 163
<211> LENGTH: 22
<212> TYPE: DNA
<213> ORGANISM: artificial
<220> FEATURE:
<223> OTHER INFORMATION: PHM2189 external reverse primer

<400> SEQUENCE: 163
ttaattaaca cggtcatgga tc                                                    22

<210> SEQ ID NO 164
<211> LENGTH: 18
<212> TYPE: DNA
<213> ORGANISM: artificial
<220> FEATURE:
<223> OTHER INFORMATION: PHM7734 internal forward primer

<400> SEQUENCE: 164
gaagtccctg gtttcctc                                                         18

<210> SEQ ID NO 165
<211> LENGTH: 19
<212> TYPE: DNA
<213> ORGANISM: artificial
<220> FEATURE:
<223> OTHER INFORMATION: PHM7734 internal reverse primer

<400> SEQUENCE: 165
gcttccaccc gctaaatag                                                        19

<210> SEQ ID NO 166
<211> LENGTH: 18
<212> TYPE: DNA
<213> ORGANISM: artificial
<220> FEATURE:
<223> OTHER INFORMATION: PHM7734 external forward primer

<400> SEQUENCE: 166
ccaaaggaaa gcctggag                                                         18

<210> SEQ ID NO 167

```
<211> LENGTH: 19
<212> TYPE: DNA
<213> ORGANISM: artificial
<220> FEATURE:
<223> OTHER INFORMATION: PHM7734 external reverse primer

<400> SEQUENCE: 167
acttcccaag aacaatggc                                                   19

<210> SEQ ID NO 168
<211> LENGTH: 20
<212> TYPE: DNA
<213> ORGANISM: artificial
<220> FEATURE:
<223> OTHER INFORMATION: PHM3323 internal forward primer

<400> SEQUENCE: 168
aaaggaagaa cgttgcagcc                                                  20

<210> SEQ ID NO 169
<211> LENGTH: 21
<212> TYPE: DNA
<213> ORGANISM: artificial
<220> FEATURE:
<223> OTHER INFORMATION: PHM3323 internal reverse primer

<400> SEQUENCE: 169
ttcttgggcc ctgaattact t                                                21

<210> SEQ ID NO 170
<211> LENGTH: 21
<212> TYPE: DNA
<213> ORGANISM: artificial
<220> FEATURE:
<223> OTHER INFORMATION: PHM3323 external forward primer

<400> SEQUENCE: 170
tttattccac ttgttcggct c                                                21

<210> SEQ ID NO 171
<211> LENGTH: 20
<212> TYPE: DNA
<213> ORGANISM: artificial
<220> FEATURE:
<223> OTHER INFORMATION: PHM3323 external reverse primer

<400> SEQUENCE: 171
gtcggaactc agaagcatac                                                  20

<210> SEQ ID NO 172
<211> LENGTH: 19
<212> TYPE: DNA
<213> ORGANISM: artificial
<220> FEATURE:
<223> OTHER INFORMATION: PHM4736 internal forward primer

<400> SEQUENCE: 172
tggccaagca cacaccacg                                                   19

<210> SEQ ID NO 173
<211> LENGTH: 22
<212> TYPE: DNA
<213> ORGANISM: artificial
<220> FEATURE:
<223> OTHER INFORMATION: PHM4736 internal reverse primer

<400> SEQUENCE: 173
```
ggatatggta caatgaaatg cc                                            22

<210> SEQ ID NO 174
<211> LENGTH: 22
<212> TYPE: DNA
<213> ORGANISM: artificial
<220> FEATURE:
<223> OTHER INFORMATION: PHM4736 external forward primer

<400> SEQUENCE: 174
ttctgacata cttagctatc tc                                            22

<210> SEQ ID NO 175
<211> LENGTH: 21
<212> TYPE: DNA
<213> ORGANISM: artificial
<220> FEATURE:
<223> OTHER INFORMATION: PHM4736 external reverse primer

<400> SEQUENCE: 175
cgggcgaaag ttgtcagaac a                                             21

<210> SEQ ID NO 176
<211> LENGTH: 22
<212> TYPE: DNA
<213> ORGANISM: artificial
<220> FEATURE:
<223> OTHER INFORMATION: PHM6441 internal forward primer

<400> SEQUENCE: 176
gaaaaagtaa atgccgttat gt                                            22

<210> SEQ ID NO 177
<211> LENGTH: 22
<212> TYPE: DNA
<213> ORGANISM: artificial
<220> FEATURE:
<223> OTHER INFORMATION: PHM6441 internal reverse primer

<400> SEQUENCE: 177
aaggactcct tttccattta ct                                            22

<210> SEQ ID NO 178
<211> LENGTH: 22
<212> TYPE: DNA
<213> ORGANISM: artificial
<220> FEATURE:
<223> OTHER INFORMATION: PHM6441 external forward primer

<400> SEQUENCE: 178
ttgtttggtc tacattcttg gt                                            22

<210> SEQ ID NO 179
<211> LENGTH: 20
<212> TYPE: DNA
<213> ORGANISM: artificial
<220> FEATURE:
<223> OTHER INFORMATION: PHM6441 external reverse primer

<400> SEQUENCE: 179
gggttagcag aaagatttcc                                               20

<210> SEQ ID NO 180
<211> LENGTH: 19
<212> TYPE: DNA

```
<213> ORGANISM: artificial
<220> FEATURE:
<223> OTHER INFORMATION: PHM430 internal forward primer

<400> SEQUENCE: 180
tcagctgacc aacaggtct                                              19

<210> SEQ ID NO 181
<211> LENGTH: 22
<212> TYPE: DNA
<213> ORGANISM: artificial
<220> FEATURE:
<223> OTHER INFORMATION: PHM430 internal reverse primer

<400> SEQUENCE: 181
gctctcttac agatttatat ta                                          22

<210> SEQ ID NO 182
<211> LENGTH: 18
<212> TYPE: DNA
<213> ORGANISM: artificial
<220> FEATURE:
<223> OTHER INFORMATION: PHM430 external forward primer

<400> SEQUENCE: 182
cgacgctcct cctcatcc                                               18

<210> SEQ ID NO 183
<211> LENGTH: 20
<212> TYPE: DNA
<213> ORGANISM: artificial
<220> FEATURE:
<223> OTHER INFORMATION: PHM430 external reverse primer

<400> SEQUENCE: 183
ataagcctct ccagctgtcc                                             20

<210> SEQ ID NO 184
<211> LENGTH: 22
<212> TYPE: DNA
<213> ORGANISM: artificial
<220> FEATURE:
<223> OTHER INFORMATION: PHM12224 internal forward primer

<400> SEQUENCE: 184
gttcgttgtt cagatatgtc ag                                          22

<210> SEQ ID NO 185
<211> LENGTH: 21
<212> TYPE: DNA
<213> ORGANISM: artificial
<220> FEATURE:
<223> OTHER INFORMATION: PHM12224 internal reverse primer

<400> SEQUENCE: 185
gaatccaatt gtgcagtgga a                                           21

<210> SEQ ID NO 186
<211> LENGTH: 22
<212> TYPE: DNA
<213> ORGANISM: artificial
<220> FEATURE:
<223> OTHER INFORMATION: PHM12224 external forward primer

<400> SEQUENCE: 186
cttgattttg tgtacattta tg                                          22
```

-continued

<210> SEQ ID NO 187
<211> LENGTH: 20
<212> TYPE: DNA
<213> ORGANISM: artificial
<220> FEATURE:
<223> OTHER INFORMATION: PHM12224 external reverse primer

<400> SEQUENCE: 187
acccaagctt gatgagatca                                           20

<210> SEQ ID NO 188
<211> LENGTH: 22
<212> TYPE: DNA
<213> ORGANISM: artificial
<220> FEATURE:
<223> OTHER INFORMATION: PHM11904 internal forward primer

<400> SEQUENCE: 188
aactgaataa gaatactggt cc                                        22

<210> SEQ ID NO 189
<211> LENGTH: 20
<212> TYPE: DNA
<213> ORGANISM: artificial
<220> FEATURE:
<223> OTHER INFORMATION: PHM11904 internal reverse primer

<400> SEQUENCE: 189
gaaggtccca gtgaaagagt                                           20

<210> SEQ ID NO 190
<211> LENGTH: 22
<212> TYPE: DNA
<213> ORGANISM: artificial
<220> FEATURE:
<223> OTHER INFORMATION: PHM11904 external forward primer

<400> SEQUENCE: 190
cttaacttct atgactaagt ac                                        22

<210> SEQ ID NO 191
<211> LENGTH: 22
<212> TYPE: DNA
<213> ORGANISM: artificial
<220> FEATURE:
<223> OTHER INFORMATION: PHM11904 external reverse primer

<400> SEQUENCE: 191
tttaaccatc caccatatct gt                                        22

<210> SEQ ID NO 192
<211> LENGTH: 22
<212> TYPE: DNA
<213> ORGANISM: artificial
<220> FEATURE:
<223> OTHER INFORMATION: PHM6727 internal forward primer

<400> SEQUENCE: 192
tttctctatt gcaaatcatg gt                                        22

<210> SEQ ID NO 193
<211> LENGTH: 21
<212> TYPE: DNA
<213> ORGANISM: artificial
<220> FEATURE:

<223> OTHER INFORMATION: PHM6727 internal reverse primer

<400> SEQUENCE: 193
cgaatagaaa aggagaaaga g                                           21

<210> SEQ ID NO 194
<211> LENGTH: 18
<212> TYPE: DNA
<213> ORGANISM: artificial
<220> FEATURE:
<223> OTHER INFORMATION: PHM6727 external forward primer

<400> SEQUENCE: 194
tcccatcctg caccgaga                                               18

<210> SEQ ID NO 195
<211> LENGTH: 20
<212> TYPE: DNA
<213> ORGANISM: artificial
<220> FEATURE:
<223> OTHER INFORMATION: PHM6727 external reverse primer

<400> SEQUENCE: 195
gatttgcata gttatctcaa                                             20

<210> SEQ ID NO 196
<211> LENGTH: 609
<212> TYPE: DNA
<213> ORGANISM: artificial
<220> FEATURE:
<223> OTHER INFORMATION: PHM4578 reference sequence

<400> SEQUENCE: 196
cccatcatca cacacttatt tgtttgtgtg gtgctttaca acgtaaggag ccattccctc      60
tcccactact atgttctctt tagttgtgct ggcaagaatt atacagaaat atcagcacac     120
aagtaacgct tgcctgtgg acatggtctt tgcaggtgaa tgcattccct atcactgtca      180
tgtttgggat gtgttctatc ttcctcttca tggcagcaat cttgcagaga cggctgatgg     240
ttgtctctga tcaagtacac aaatcatcaa ctagtacgtg atattctgat tcccttctt     300 ctgttccagc aatcctgcgc caatgaaggc ttaaattgtt atctctgata aactggagaa     360
aatcaggttc atttttttca ttgctaacct tagggtaaca ttccttgcag aagcacaaga     420
aatgatcggg gaagatgagc cactaaatcc ttagatgtcg acagaaccat acatgcgaaa     480
tcagatattg aagacgacgt acatactgca tttcgtttcg tcacctgtgc aataagatgg     540
acgtcaaaac catgtagtct agtggttttc gtttctgtag tgtagatttg accaggctgc     600
atgtcatag                                                            609

<210> SEQ ID NO 197
<211> LENGTH: 581
<212> TYPE: DNA
<213> ORGANISM: artificial
<220> FEATURE:
<223> OTHER INFORMATION: PHM11186 reference sequence

<400> SEQUENCE: 197 ccccccaacac ccccagtccc aacagattag gattaaagca tgtcggagtc cccggagttg     60
tacaggcccg cggaagcgcc ggccttctcg ccgtcctgcg ccacgcaggc tcccgctcgt    120
gttcgccggc gacgactact gctgcaggac gccgacgggc agcgggatct gctacctgag    180
ggagcccacc acgtgcccgc ccgcgccccg gaagccgccg ccgccgccgc ccatgtgcag    240

```
gaagcgcctc ttccaagcgg cggatcagca ggttgctgag gcggggcccg tccctgttat    300
cagcatccgc ctcgacgagc tggagcgcct cttccgcccc tgtccgccgc cgaccaccac    360
caccaccgac aagcgacgcc gctccggctc cggccccagc cccagatccg ccacgaaaca    420
tggtgctcag ctgcagctgc gcagcatgaa ttgaattggg ttagcgtaac gtagcttgca    480
cgcaccaacc aaccactccc tttttagttt ttgctgctgc atctgtctgc ttcttgtgct    540
caacaagcaa agccagaatt tggtattatg cawctaactt t                        581

<210> SEQ ID NO 198
<211> LENGTH: 480
<212> TYPE: DNA
<213> ORGANISM: artificial
<220> FEATURE:
<223> OTHER INFORMATION: PHM14053 reference sequence

<400> SEQUENCE: 198
ccggcttgag cagtgaaggc gccccagctg gaggcagttg aacggcgcac gtgaggcggc     60
ggcgcaggcg gtggcgagct gatggggtgc ccccgaacgc gagggacatg aagaaggacg    120
agaagagcgt ggccaacctg gtgcagctgc tggacccgag cccccagaac acggccaaga    180
agtacgccat ctcctgcctg ctggcgcttt cgacgagcaa gcggtgcaag aagctgatga    240
tctcccacgg cgctatcggg tacctgaaga agctctcgga gtcggagaag gacgtggccg    300
gcgcgaagaa gctgctcgag aagctggacc gaggaaggct acgcagcctg ttcggcagga    360
agtagccacc aggcgatcga tcgttcttca tgtacaaaga tcccgtccgt cctgtttgtg    420
tcatagcctc tatgactatg atgaagtgaa gtgcgatggt catagctgtt tctgccccccc   480

<210> SEQ ID NO 199
<211> LENGTH: 610
<212> TYPE: DNA
<213> ORGANISM: artificial
<220> FEATURE:
<223> OTHER INFORMATION: PHM16736 reference sequence

<400> SEQUENCE: 199
gtcacggagg cctaaacgtc tatttgattt cttaattata aaccgtgaga gcatgtttgt     60
atagctattt taaatttata atcctatggc tcctcttttg cattgaagta ctgaacttat    120
gcaattatct ctttagctac tatcaggttc ggttattttt ttttcattat ttttctcctc    180
tctgaagcgg ctatccacat gccccgaatt ggttaccaag gtggctccca acgatcagaa    240
tggtatacaa tagaacgcct gctcaggaaa cactcatctc tccatggaat cgacattttt    300
gtgtatgcca tgagaacaca gtttcattta tgagttacta ccgtcgata tgtacttgct    360 aatgaagaac aactgctacc aaccattttc ctcctgcaga tactactttc agcgacgaca    420
ggcagattgc cagattgtaa cccaggtagg tcatgctgac gattcgaccc aagcgtaggg    480
atgtctctgt aaaaacccac tacatcagaa gaatctggga ttatgtgtag ctagctgcaa    540
caatttgtct tttgtttttac tgccccttct ctctggacca aaacgcctat aattgatgaa    600
tttataaacc                                                           610

<210> SEQ ID NO 200
<211> LENGTH: 646
<212> TYPE: DNA
<213> ORGANISM: artificial
<220> FEATURE:
<223> OTHER INFORMATION: PHM7844 reference sequence
```

<400> SEQUENCE: 200

```
agattgatcg agttatgcac tcttcccctt ggcacattca aaaattaggg gatcttgtag    60
ttgccagggg gatcatgcag cagaacagtt tatatgatgg tgtgccttat aagatgtagt   120
gcatattcct ttttttgtt aagtttgttc tcgcaacagt cattgtagat tatgacaagt   180
ggcttcatga taagatgttt gctcgtatta tacctgacgt tcattgtttg tcttggttca   240
tgcaattctt gaaaattagt aactcaaatt cattttttctg attattgcat gttctggtat   300
atgcttctag gcttttgctt gggcgtacgc tcgaggagat catacaacat ttgaccacct   360
actggtatat tggctggcgc ccctgcaagc aaccctttctg ggagtatggg cggtgaccttt  420
cttcactaaa ccaaagaaga tcaaggagca aaggtagat gaaaacaaga taagaagga    480
atagactatt cttgaattag agctagagct tcataccatc ttcttagtca gataacttgt   540
ggctacacac aaggcgaaat gtttcgaagc taatctaaga aatggcaacc tatcatggtc   600
agcttctgtg aagtctcctt gatgggattc ctgaaacttt aaataa                646
```

<210> SEQ ID NO 201
<211> LENGTH: 571
<212> TYPE: DNA
<213> ORGANISM: artificial
<220> FEATURE:
<223> OTHER INFORMATION: PHM8029 reference sequence

<400> SEQUENCE: 201

```
caccgtcaca acgttctaca ccatgctgac ggaggagctg caggcggtgc ggctggcgtg    60
ctcgaggcac ccgggctaca agccggcgat cacgttcgtg gtggtccaga agaggcagca   120
caccaggctg ttccacaggg agaagaatgg cggcggtggc ggtggcggcg gcggcggctc   180
cacgcactat gccgaccaga atgtgccgcc ggggacggtg gtggacaccg tgatcacgca   240
tccgagggag ttcgacttct acctgtgcag ccactggggc accaagggga cgaccaggcc   300
gacgcactac cgcgtgctgt gggacagaaa cggcttcggg tccgacgaga tgcagcagct   360
gatacacagc ctttgctaca cgttcgcccg gtgcaccaag cccgtgtccc tcgtcccgcc   420
ggcgtactac cgcacctgg ccgcgtacag aggacggctg taccttgaga ggtcggactc   480
ggcggcgacc ggccggacga ctctgtacag gccggcgcca ttgcagactg cgccgctccc   540
taagctcaga atagctactt tccggtttag t                                  571
```

<210> SEQ ID NO 202
<211> LENGTH: 660
<212> TYPE: DNA
<213> ORGANISM: artificial
<220> FEATURE:
<223> OTHER INFORMATION: PHM2130 reference sequence

<400> SEQUENCE: 202

```
ctttttaagt tgaaggatta gttgctgcta tgtctacttg ctcctatgca ttttgttcaa    60
ccagctttgt gttattgtta aaacctactg tttacggcca tcactctacc attcgatctc   120
ataatgtttc cattttttgt ggataatcat cctgccatga tcatgtcatc tttctcaaca   180
ctgttattta tttcagttat tgcacaaaga agctggcaga aggctgggaa gcggaccagg   240
cggcagtgac gaaatcaaga accacaagtg gttcaagtct gtaaactgga agaggctgga   300
ggcccggcag atcgagccaa gcttccggcc gaatgttgct ggcaagacct gcattgcgaa   360
cttttgacagag tgctgacga acatgcccgt gcttgattct ccggtggcca gccctgttgc   420
ggccaacagc aactttgtgg ggttcagtta tgtgaggccc gcaccgttcc tccagaagcc   480
```

```
gagtcccctt ggctaaagaa ctacttccgt gatctgatat ctaccccaga gttcaaataa      540
ctatctttga gtccgaatcc tatgtatttc ttcaagacat tagtgatggg aatctaacct      600
tattgttgtg ttgtgggtag gccagccaag cgcctattgc ttgaaaacaa cagcttggca      660
```

<210> SEQ ID NO 203
<211> LENGTH: 834
<212> TYPE: DNA
<213> ORGANISM: artificial
<220> FEATURE:
<223> OTHER INFORMATION: PHM11754 reference sequence

<400> SEQUENCE: 203

```
cccagtcaca acaattctac aagaatgtgg tagttaaaac cgttattgta cttaagtcag       60
taccagttct agctaattaa aggaactgat actaagaaca tctccaaaag actagctaaa      120
taactcccca agccaaattt tggatactca atagcaaaat aactctccaa cagattagct      180
atcggactcg ccaagttatc cgactcttca aattcactct ctcactagcc aaatttggct      240
agccacctaa ctagcaaaac tagatagata gtctgttgga atgagagtgt aatcttgatg      300
aaaagttaaa tagatagtta aatatagagc taaaaattag gagtctcatg gagatgctct      360
aatttcctca cacggaagct ctgatctcta gcaatgagac taatttccat cggttttcgt      420
aagtaagccg attgaaaatt aatctctccg tttcgtttta gttgtcgtta gatagtgcaa      480
aattgaacta tctagcgaca actaaaaaaa cagagggagt agctattttc tgtccgttgc      540
taacaaaaat tagctatttt ttattcatta atatagaaga gctagagtct caagaaaatt      600
attcagatta cttactttgg tgaatataaa gcaaaccaga ctgcatgatc gacagggtta      660
ttacactagc taggcatgcc gatatgcggc aatttccgac ctacgacaca cgcgcggtac      720
acaccaaacg gcaaacgtac aatacaaaca caaacgaaag ccggcccatc catttttatt      780
ttctttgtca caactcacac gacaataatc tatacagcga aagggcttat aaac           834
```

<210> SEQ ID NO 204
<211> LENGTH: 593
<212> TYPE: DNA
<213> ORGANISM: artificial
<220> FEATURE:
<223> OTHER INFORMATION: PHM1481 reference sequence

<400> SEQUENCE: 204

```
agaagggagg acccagtcaa cgtgatctcg atgaagagga tgatgatgca gttgatcctg       60
ctgaatcaaa catgagagat gtcctagatg accttgaatc ttttgacttg ggtaatggag      120
ggtccaaaac tacagcaaag aagaaagagg cgtcccacaa gcaccacaag aagccccagc      180
ggaagaagga tcggtcctgg agggttggca atgatggtgg cgacggaaca gcagttgtaa      240
gagtgtacca gaaacccgca gttaatttgt ccacgggctc tttaagtggc agggtctgat      300
gccctaactt ttactgctcg cacaaccccg gcacacatgg gcaagggcat gggacctctt      360
actgtagcaa cggctgaact ctgaagctac ttcgatggaa ggaagaaagg agtactgagc      420
atacgagagt ttgaaaacct tagaaacaac attgtagtcg tgccgaacta ccccggctac      480
acatgggcaa gggcatggga cctcttactg tagcaacggc tgaactctga agctacttcg      540
atggaaggaa gaaaggagta ctgagcatac gagagtttga aaaccttaga aac             593
```

<210> SEQ ID NO 205
<211> LENGTH: 744
<212> TYPE: DNA

<213> ORGANISM: artificial
<220> FEATURE:
<223> OTHER INFORMATION: PHM15089 reference sequence

<400> SEQUENCE: 205

| | | | | | |
|---|---|---|---|---|---|
| ggtaaggtcc | cagtcacgac | gagtgccaca | agcgcaacca | cccgtcggcg | cggctgatga | 60 |
| cagcgctccg | cgagctcgac | ctggacgtgt | accacgccag | cgtgtccgtc | gtcaaggacc | 120 |
| tcatgatcca | gcaggtcgcc | gtcaagatgg | ccagccgcgt | gtacacgcag | gaccagctca | 180 |
| gcgccgcgct | ctacagccgc | ctcgcggagc | ccgggtctgc | catgggcagg | taatcaagga | 240 |
| ggagagctgc | tcagctcgcc | tgtggctgcc | ggaatagggg | acgacactga | tactactgct | 300 |
| actcaccacc | ggactgtcct | gtcgtcgtgg | tcaccacggt | tacaacacga | taggcagaaa | 360 |
| gattcaggag | ggagggagac | gacgacgatg | ccggtgctgt | ataaactta | gaaggatgga | 420 |
| tggatggatg | atgataccga | gcttctgctc | ctgttcatca | tcatcttctt | gtgttttgc | 480 |
| tagtagcgtg | ttaattagca | gattaagcaa | ccaacaagtt | ccaacctta | atttgaaata | 540 |
| gcagcttatt | tgataagctg | gtgaaaagca | gcttctgctt | gttggctgct | tttagttcat | 600 |
| tctgagaagc | agctgaactg | ataagctgct | ggagaagctg | cctgttttggc | agaacttcag | 660 |
| cttaaatttg | tgaagaagct | gaaaataagc | tgtgccaaaa | caggcctaag | caaccaacaa | 720 |
| gttccaaccg | tgaaatkgtg | gtta | | | | 744 |

<210> SEQ ID NO 206
<211> LENGTH: 585
<212> TYPE: DNA
<213> ORGANISM: artificial
<220> FEATURE:
<223> OTHER INFORMATION: PHM574 reference sequence

<400> SEQUENCE: 206

| | | | | | |
|---|---|---|---|---|---|
| tcgckkacttt | ttttgcgcgt | actgtaagaa | agcaagaatg | taattcacca | tttactcaga | 60 |
| tcaccaaact | ggcttatctt | tattgttgcc | tggctaacat | gatatgctat | ttccagatac | 120 |
| tctttgtcat | ctccaaacca | gatgtgttca | agagcccgaa | ttccgacacg | tatgtcatat | 180 |
| tcggcgaggc | taagatcgag | gacctcagct | cccagctgca | gacccaggca | gcagagcagt | 240 |
| tcaaggctcc | tgacttgagc | cagatgatct | cgaatccaga | gacgtctggc | ccgggacagg | 300 |
| aggacaatga | tgaggaggtc | gacgaaactg | gtgttgaggc | caaggacatt | gagctggtga | 360 |
| tgacccaggc | atctgtttca | aggcccaagg | ctgtcaaggc | cctcaaggct | tctaatgggg | 420 |
| acattgtcac | tgccatcatg | gatctgacaa | cctagggtga | tatttctgtc | cgtgccactt | 480 |
| ttgttttgga | gtgctattgc | aacttgagtg | ttatatgtgg | acctatgctt | cgatgatgtt | 540 |
| acatgattgc | ttcttgggtc | aaggtcattc | aaatggtcat | agctg | | 585 |

<210> SEQ ID NO 207
<211> LENGTH: 503
<212> TYPE: DNA
<213> ORGANISM: artificial
<220> FEATURE:
<223> OTHER INFORMATION: PHM6427 reference sequence

<400> SEQUENCE: 207

| | | | | | |
|---|---|---|---|---|---|
| aatggggaag | ggcccagtca | cgaagcccat | atcttatctg | catttagtgt | acactacagt | 60 |
| ctacaaggcg | tctttgttca | attggcaacc | aaaataaatg | ggggtgatt | catgagacag | 120 |
| acaaatctaa | tgtggaacat | aaagcagatt | aattagtcca | ttacgggcat | gtagccatct | 180 |
| catgtttgtc | taaataacct | tccaagacag | tttgtcaaat | gccaaataaa | agagaatggg | 240 |

```
aagtaaatgt gttcatcttc taaagtgaaa tatttgatcg ccgttgatgt ttctaaatgt    300
tggactggct tttattgcat tgtcaggcta ataataagat ggagttcgtc ttcgcaagtc    360
attcttttga tgtttgtgag agctggatgc tggaagggtg cctttcagaa tactgcaaac    420
ttgttaatcg caaaaatgct atggtacgtt cattcatcct tgccattcta agcagataaa    480
cttactacaa attttttat taa                                             503

<210> SEQ ID NO 208
<211> LENGTH: 509
<212> TYPE: DNA
<213> ORGANISM: artificial
<220> FEATURE:
<223> OTHER INFORMATION: PHM11125 reference sequence

<400> SEQUENCE: 208
cccggataaa tcccagtcaa aatgacgcgc aaagctccgc atccgcaccg ccaccgccc     60 gcccgcccgc gccggccgcc ggcggcgtgg atggggaagc tctccgccct gaagcgggaa   120
gcggtcggag tggactaggc gctcggtgac ttcctagttt agaagcggta ggtggaggcg   180
atgcggggcg gggcgatgaa ggccctgcgg cgatccagca cctcctcggc gccatcgcca   240
agggtgccgt cttccccgcg gtcttattcg tggatccacc gccggtcgct tctcgttacc   300
tcgccggcct cgccggcgac gtcctctgtg tctgaatcgg cgaatttgcc cgcggagggt   360
tcggattcag cgccagcgtc agtggtggca gcttcctcgt cgccctcgct ggctgcttcg   420
tctccgaaca tggaatggtg gggctatcct gtccggattt ctcctcgtgc tgcatggtcg   480
cttcaaaatt ggataacttt tcttaaaaa                                     509

<210> SEQ ID NO 209
<211> LENGTH: 433
<212> TYPE: DNA
<213> ORGANISM: artificial
<220> FEATURE:
<223> OTHER INFORMATION: PHM13958 reference sequence

<400> SEQUENCE: 209
acgtacaacc accaatatag cactttcggc gtctctagag ataaacaacc ctcagtggac    60
gtatcgttga tacagcatgc ctgagaatgt atcatgtaaa tgatggagca gatgaaaaat   120
tccgcggttg ctagattggc ttaaactttt gcagcagtgg tgtaatagat gttaatctca   180
ttgctctgta ggattgaagt cagctgaatt tggaatgctc tcttgctttt ggagagctgc   240
tcatgtccac tgtgaatcgt cttttgacgc tcctgtatat cttgggtagc tagctaatga   300
tcatattttt ggtgctgctc tttcaaatga tgctacattt atcattactt ctcttttaat   360
aattagggag tcttttagga ttttttgttt tccacatcca gaaactttag gatggtcata   420
gctgtacctt ccc                                                      433

<210> SEQ ID NO 210
<211> LENGTH: 508
<212> TYPE: DNA
<213> ORGANISM: artificial
<220> FEATURE:
<223> OTHER INFORMATION: PHM10468 reference sequence

<400> SEQUENCE: 210
tcatgagcga ggaccccgt aaaggatgtg atgaacagag gaagtcatct atgcctagtt      60
tgcctatgca tggtggtaaa tcactaatcg tccattgttg ggagcatgtt catccacgga   120
```

```
cggacgagat aaggtgctga gttgatatga ccataatcca tgtacagtgt gtcacctgaa    180
cacttgtttg tactgatttg gatgctgtca gacatgtcgt atttgtgaat cggaattcta    240
ggactattat gctagtatat acttcacatg aatggcgaag atggatggtg tgtcggatcc    300
tagcatagtg atggtgttgg cagcacacag tccaagcaaa tcgaatctca atcgaagaac    360
atcgccatac aatccaagct tctctggtag ctatgtgatc ggcctgagcc acaggacagg    420
acatgcattg gggagcgcta gagaagacgg tggccgcaaa caccaatgac atcgtcatgg    480
tcatagctga cctttccccc attttttt                                      508

<210> SEQ ID NO 211
<211> LENGTH: 541
<212> TYPE: DNA
<213> ORGANISM: artificial
<220> FEATURE:
<223> OTHER INFORMATION: PHM12706 reference sequence

<400> SEQUENCE: 211
ggaagggccc agtccaacga aagccctaag agtcaccaaa actgggtatt catctgtcat     60
tggatatttc cacctaatat tgtttaatgc tattgtttcc atatttccag atccctcact    120
tgaggcctgc tgagtacaaa aggtccaggt tgcctaggag ccgcaggact gtgaaccgtc    180
cttatggtgg agtactctct ggaattgctg ttagggagag gtgagtaaat aggggggtgga    240 catattgtgt gtggaggtc caggttctgt aattttcgta gtcttatgaa ttacaactac    300
tgtatgcaga atcattcgtg ctttcttggt cgaggagcag aagattgtca agaaggtcct    360
gaaaatacaa aaaccaagg acaagacagc tgcaaagtaa atctccagga atggggaagc    420
ctagccctgt tttgtacact gcgaaaatta attttggtgg atggaaaatc taggtgcctt    480
gttgagcatt tagcatgtgt gagtttagag agtctgagag tctacactaa acttaaggta    540
a                                                                   541

<210> SEQ ID NO 212
<211> LENGTH: 469
<212> TYPE: DNA
<213> ORGANISM: artificial
<220> FEATURE:
<223> OTHER INFORMATION: PHM405 reference sequence

<400> SEQUENCE: 212
cccagtcaca acgtgatgat gactacgacg accagcctcc agcccggatg gtgatgagga     60
atcagcaacg actactggcg acggagaagc ggctgatcga gctcgagagg aagcgcttct    120
tcgcgatgcc gccgcagcag taccagcacg tctacttcga ctgcagcatc ggggacgacg    180
acggccaggg ccagccacca ccacgacatc ttcccctcat cataacccaa ccagctcggg    240
caagcagcag cagcagttac gacgacgacg acgacgacat ccaactccca gaaagcccat    300
tcacgtcgtc agccgtgccg atgctgatgt aatgggccgg gaaagggaaa ccaaggtcca    360
cttaattagc ttcttttgtt acacaggaca ggacaggaca caaaaacacc ctctttttg    420 ttgtagatat aaacaaatta aggagtcaca tacacagaaa atttatkta              469

<210> SEQ ID NO 213
<211> LENGTH: 600
<212> TYPE: DNA
<213> ORGANISM: artificial
<220> FEATURE:
<223> OTHER INFORMATION: PHM12025 reference sequence

<400> SEQUENCE: 213
```

```
atctgatttt ctatcaacgg gggcaatcag tggtggtatc acaagcagta gcgaagctag      60
caaataattt atcggggtca tcagtattat ctactggatc tttaccatag aacttttgtt     120
attaacaccg tttttctatt agatatttcg caaaccccgt gatatggtat ctgattttct     180
atcaacgggg gcaatcggtg gtggtatcac aaggggggcat gagacaggca ctaacaagga    240
ccacgcggca cctgctatat atggtatgtt tggttgcgcc ggaattagaa cggcattcaa     300
ggatatatag ggtctgtttg gttcgctact agcttgttac gttttattta acttttttac     360
ctaaaattag ttcttcaatt cgaacgacta acattaaaca aaccacgaac caaacagact     420
cataatccct tgttagccaa atgttagcta aggtattata tactcctcaa tctcctataa     480
tcctcatgca accaaaacaa aactataaaa ctttatatag gcaagggtat aaaaatggcc     540
aaatttgcaa actaccacag gcgaaatatc aatggttata gctgccccctt cccctttttgt   600
```

<210> SEQ ID NO 214
<211> LENGTH: 22
<212> TYPE: DNA
<213> ORGANISM: artificial
<220> FEATURE:
<223> OTHER INFORMATION: PHM4578 external forward primer

<400> SEQUENCE: 214

```
atgaagatga gatctcagta ca                                              22
```

<210> SEQ ID NO 215
<211> LENGTH: 21
<212> TYPE: DNA
<213> ORGANISM: artificial
<220> FEATURE:
<223> OTHER INFORMATION: PHM4578 internal forward primer

<400> SEQUENCE: 215

```
ttccgcatac cactcaactt a                                               21
```

<210> SEQ ID NO 216
<211> LENGTH: 20
<212> TYPE: DNA
<213> ORGANISM: artificial
<220> FEATURE:
<223> OTHER INFORMATION: PHM4578 internal reverse primer

<400> SEQUENCE: 216

```
gcagcctggt caaatctaca                                                 20
```

<210> SEQ ID NO 217
<211> LENGTH: 22
<212> TYPE: DNA
<213> ORGANISM: artificial
<220> FEATURE:
<223> OTHER INFORMATION: PHM4578 external reverse primer

<400> SEQUENCE: 217

```
gattgacttg ctcatctaat ct                                              22
```

<210> SEQ ID NO 218
<211> LENGTH: 19
<212> TYPE: DNA
<213> ORGANISM: artificial
<220> FEATURE:
<223> OTHER INFORMATION: PHM11186 external forward primer

<400> SEQUENCE: 218
ctcacctgcc ctatacaca                                            19

<210> SEQ ID NO 219
<211> LENGTH: 21
<212> TYPE: DNA
<213> ORGANISM: artificial
<220> FEATURE:
<223> OTHER INFORMATION: PHM11186 internal forward primer

<400> SEQUENCE: 219
gattaggatt acagcatgtc g                                         21

<210> SEQ ID NO 220
<211> LENGTH: 19
<212> TYPE: DNA
<213> ORGANISM: artificial
<220> FEATURE:
<223> OTHER INFORMATION: PHM11186 internal reverse primer

<400> SEQUENCE: 220
cgcttgcgct ttgcttgtt                                            19

<210> SEQ ID NO 221
<211> LENGTH: 19
<212> TYPE: DNA
<213> ORGANISM: artificial
<220> FEATURE:
<223> OTHER INFORMATION: PHM11186 external reverse primer

<400> SEQUENCE: 221
tgggtactgc ttgcttcgt                                            19

<210> SEQ ID NO 222
<211> LENGTH: 21
<212> TYPE: DNA
<213> ORGANISM: artificial
<220> FEATURE:
<223> OTHER INFORMATION: PHM14053 external forward primer

<400> SEQUENCE: 222
tttccaagaa ctcgctgtgt c                                         21

<210> SEQ ID NO 223
<211> LENGTH: 19
<212> TYPE: DNA
<213> ORGANISM: artificial
<220> FEATURE:
<223> OTHER INFORMATION: PHM14053 internal forward primer

<400> SEQUENCE: 223
tgctggaggc caagtcgaa                                            19

<210> SEQ ID NO 224
<211> LENGTH: 21
<212> TYPE: DNA
<213> ORGANISM: artificial
<220> FEATURE:
<223> OTHER INFORMATION: PHM14053 internal reverse primer

<400> SEQUENCE: 224
cgcacttcac ttcatcatag t                                         21

<210> SEQ ID NO 225
<211> LENGTH: 21
<212> TYPE: DNA
<213> ORGANISM: artificial

```
<220> FEATURE:
<223> OTHER INFORMATION: PHM14053 external reverse primer

<400> SEQUENCE: 225
tgttagggac ttcacatgaa c                                              21

<210> SEQ ID NO 226
<211> LENGTH: 20
<212> TYPE: DNA
<213> ORGANISM: artificial
<220> FEATURE:
<223> OTHER INFORMATION: PHM16736 external forward primer

<400> SEQUENCE: 226
gccactcatc tcttcagcaa                                                20

<210> SEQ ID NO 227
<211> LENGTH: 22
<212> TYPE: DNA
<213> ORGANISM: artificial
<220> FEATURE:
<223> OTHER INFORMATION: PHM16736 internal forward primer

<400> SEQUENCE: 227
gcctaaacgt ctatttgatt tc                                             22

<210> SEQ ID NO 228
<211> LENGTH: 21
<212> TYPE: DNA
<213> ORGANISM: artificial
<220> FEATURE:
<223> OTHER INFORMATION: PHM16736 internal reverse primer

<400> SEQUENCE: 228
cctcatctat tcataggcgt t                                              21

<210> SEQ ID NO 229
<211> LENGTH: 21
<212> TYPE: DNA
<213> ORGANISM: artificial
<220> FEATURE:
<223> OTHER INFORMATION: PHM16736 external reverse primer

<400> SEQUENCE: 229
aaagagactg cagatgcaaa c                                              21

<210> SEQ ID NO 230
<211> LENGTH: 22
<212> TYPE: DNA
<213> ORGANISM: artificial
<220> FEATURE:
<223> OTHER INFORMATION: PHM7844 external forward primer

<400> SEQUENCE: 230
gcttagcaac tttcatggtt gt                                             22

<210> SEQ ID NO 231
<211> LENGTH: 22
<212> TYPE: DNA
<213> ORGANISM: artificial
<220> FEATURE:
<223> OTHER INFORMATION: PHM7844 internal forward primer

<400> SEQUENCE: 231
acaagcattt ggaagaacac aa                                             22
```

```
<210> SEQ ID NO 232
<211> LENGTH: 22
<212> TYPE: DNA
<213> ORGANISM: artificial
<220> FEATURE:
<223> OTHER INFORMATION: PHM7844 internal reverse primer

<400> SEQUENCE: 232
gatacaagga atacacatca ag                                              22

<210> SEQ ID NO 233
<211> LENGTH: 22
<212> TYPE: DNA
<213> ORGANISM: artificial
<220> FEATURE:
<223> OTHER INFORMATION: PHM7844 external reverse primer

<400> SEQUENCE: 233
tactgtttcc aatacgacaa tg                                              22

<210> SEQ ID NO 234
<211> LENGTH: 20
<212> TYPE: DNA
<213> ORGANISM: artificial
<220> FEATURE:
<223> OTHER INFORMATION: PHM8029 external forward primer

<400> SEQUENCE: 234
ttcgtgaagg aagtcggcaa                                                 20

<210> SEQ ID NO 235
<211> LENGTH: 20
<212> TYPE: DNA
<213> ORGANISM: artificial
<220> FEATURE:
<223> OTHER INFORMATION: PHM8029 internal forward primer

<400> SEQUENCE: 235
ttctacaagg tgctgacgga                                                 20

<210> SEQ ID NO 236
<211> LENGTH: 21
<212> TYPE: DNA
<213> ORGANISM: artificial
<220> FEATURE:
<223> OTHER INFORMATION: PHM8029 internal reverse primer

<400> SEQUENCE: 236
tcacgctatc tctgagctta g                                               21

<210> SEQ ID NO 237
<211> LENGTH: 22
<212> TYPE: DNA
<213> ORGANISM: artificial
<220> FEATURE:
<223> OTHER INFORMATION: PHM8029 external reverse primer

<400> SEQUENCE: 237
tcatcataag atcagcagta ga                                              22

<210> SEQ ID NO 238
<211> LENGTH: 21
<212> TYPE: DNA
<213> ORGANISM: artificial
<220> FEATURE:
<223> OTHER INFORMATION: PHM2130 external forward primer
```

```
<400> SEQUENCE: 238
gtggaaacag agacaagatt c                                      21

<210> SEQ ID NO 239
<211> LENGTH: 22
<212> TYPE: DNA
<213> ORGANISM: artificial
<220> FEATURE:
<223> OTHER INFORMATION: PHM2130 internal forward primer

<400> SEQUENCE: 239
gttcactcaa tgttgaaagg at                                     22

<210> SEQ ID NO 240
<211> LENGTH: 22
<212> TYPE: DNA
<213> ORGANISM: artificial
<220> FEATURE:
<223> OTHER INFORMATION: PHM2130 internal reverse primer

<400> SEQUENCE: 240
gcaatattgc acattgtcac tt                                     22

<210> SEQ ID NO 241
<211> LENGTH: 21
<212> TYPE: DNA
<213> ORGANISM: artificial
<220> FEATURE:
<223> OTHER INFORMATION: PHM2130 external reverse primer

<400> SEQUENCE: 241
ggcgcttaat aagaacttct g                                      21

<210> SEQ ID NO 242
<211> LENGTH: 22
<212> TYPE: DNA
<213> ORGANISM: artificial
<220> FEATURE:
<223> OTHER INFORMATION: PHM11754 external forward primer

<400> SEQUENCE: 242
aatattagta ccagttggag ac                                     22

<210> SEQ ID NO 243
<211> LENGTH: 22
<212> TYPE: DNA
<213> ORGANISM: artificial
<220> FEATURE:
<223> OTHER INFORMATION: PHM11754 internal forward primer

<400> SEQUENCE: 243
gttctacaag agtgtggtag tt                                     22

<210> SEQ ID NO 244
<211> LENGTH: 21
<212> TYPE: DNA
<213> ORGANISM: artificial
<220> FEATURE:
<223> OTHER INFORMATION: PHM11754 internal reverse primer

<400> SEQUENCE: 244
ctggttgtta ctagattatt g                                      21

<210> SEQ ID NO 245
```

```
<211> LENGTH: 22
<212> TYPE: DNA
<213> ORGANISM: artificial
<220> FEATURE:
<223> OTHER INFORMATION: PHM11754 external reverse primer

<400> SEQUENCE: 245
tgcatatact attcagctgc tg                                              22

<210> SEQ ID NO 246
<211> LENGTH: 20
<212> TYPE: DNA
<213> ORGANISM: artificial
<220> FEATURE:
<223> OTHER INFORMATION: PHM1481 external forward primer

<400> SEQUENCE: 246
cctgaggtgg actttgaaca                                                 20

<210> SEQ ID NO 247
<211> LENGTH: 22
<212> TYPE: DNA
<213> ORGANISM: artificial
<220> FEATURE:
<223> OTHER INFORMATION: PHM1481 internal forward primer

<400> SEQUENCE: 247
tgatctcgat gaagaggatg at                                              22

<210> SEQ ID NO 248
<211> LENGTH: 20
<212> TYPE: DNA
<213> ORGANISM: artificial
<220> FEATURE:
<223> OTHER INFORMATION: PHM1481 internal reverse primer

<400> SEQUENCE: 248
acaagttccg gcaacgacta                                                 20

<210> SEQ ID NO 249
<211> LENGTH: 22
<212> TYPE: DNA
<213> ORGANISM: artificial
<220> FEATURE:
<223> OTHER INFORMATION: PHM1481 external reverse primer

<400> SEQUENCE: 249
ccaccacgtt tagtatgaat ca                                              22

<210> SEQ ID NO 250
<211> LENGTH: 19
<212> TYPE: DNA
<213> ORGANISM: artificial
<220> FEATURE:
<223> OTHER INFORMATION: PHM15089 external forward primer

<400> SEQUENCE: 250
tggagatcga cgccaagat                                                  19

<210> SEQ ID NO 251
<211> LENGTH: 19
<212> TYPE: DNA
<213> ORGANISM: artificial
<220> FEATURE:
<223> OTHER INFORMATION: PHM15089 internal forward primer

<400> SEQUENCE: 251
```

-continued agtgccacaa gcgcaacca                19

<210> SEQ ID NO 252
<211> LENGTH: 21
<212> TYPE: DNA
<213> ORGANISM: artificial
<220> FEATURE:
<223> OTHER INFORMATION: PHM15089 internal reverse primer

<400> SEQUENCE: 252
caacaacggt tggacacttg t             21

<210> SEQ ID NO 253
<211> LENGTH: 20
<212> TYPE: DNA
<213> ORGANISM: artificial
<220> FEATURE:
<223> OTHER INFORMATION: PHM15089 external reverse primer

<400> SEQUENCE: 253
aacccaacgc taacatcggt               20

<210> SEQ ID NO 254
<211> LENGTH: 19
<212> TYPE: DNA
<213> ORGANISM: artificial
<220> FEATURE:
<223> OTHER INFORMATION: PHM574 external forward primer

<400> SEQUENCE: 254
cttggcatga agcccatca                19

<210> SEQ ID NO 255
<211> LENGTH: 19
<212> TYPE: DNA
<213> ORGANISM: artificial
<220> FEATURE:
<223> OTHER INFORMATION: PHM574 internal forward primer

<400> SEQUENCE: 255
tggtgtcagc cgcgtcact                19

<210> SEQ ID NO 256
<211> LENGTH: 21
<212> TYPE: DNA
<213> ORGANISM: artificial
<220> FEATURE:
<223> OTHER INFORMATION: PHM574 internal reverse primer

<400> SEQUENCE: 256
ttgaatgacc ttgacccaag a             21

<210> SEQ ID NO 257
<211> LENGTH: 22
<212> TYPE: DNA
<213> ORGANISM: artificial
<220> FEATURE:
<223> OTHER INFORMATION: PHM574 external reverse primer

<400> SEQUENCE: 257
gaaacttaag agccattgat aa            22

<210> SEQ ID NO 258
<211> LENGTH: 22
<212> TYPE: DNA

-continued

```
<213> ORGANISM: artificial
<220> FEATURE:
<223> OTHER INFORMATION: PHM6427 external forward primer

<400> SEQUENCE: 258
ctaattaccc atgcatataa cc                                              22

<210> SEQ ID NO 259
<211> LENGTH: 22
<212> TYPE: DNA
<213> ORGANISM: artificial
<220> FEATURE:
<223> OTHER INFORMATION: PHM6427 internal forward primer

<400> SEQUENCE: 259
cccatatctt atctgcattt ag                                              22

<210> SEQ ID NO 260
<211> LENGTH: 22
<212> TYPE: DNA
<213> ORGANISM: artificial
<220> FEATURE:
<223> OTHER INFORMATION: PHM6427 internal reverse primer

<400> SEQUENCE: 260
gtgtatgtta agtttatcct gc                                              22

<210> SEQ ID NO 261
<211> LENGTH: 21
<212> TYPE: DNA
<213> ORGANISM: artificial
<220> FEATURE:
<223> OTHER INFORMATION: PHM6427 external reverse primer

<400> SEQUENCE: 261
gaatcagtgc aagtagttcg t                                               21

<210> SEQ ID NO 262
<211> LENGTH: 20
<212> TYPE: DNA
<213> ORGANISM: artificial
<220> FEATURE:
<223> OTHER INFORMATION: PHM11125 external forward primer

<400> SEQUENCE: 262
tttaaccccc ttcctctcca                                                 20

<210> SEQ ID NO 263
<211> LENGTH: 18
<212> TYPE: DNA
<213> ORGANISM: artificial
<220> FEATURE:
<223> OTHER INFORMATION: PHM11125 internal forward primer

<400> SEQUENCE: 263
acgcgcagag ctccgcat                                                   18

<210> SEQ ID NO 264
<211> LENGTH: 22
<212> TYPE: DNA
<213> ORGANISM: artificial
<220> FEATURE:
<223> OTHER INFORMATION: PHM11125 internal reverse primer

<400> SEQUENCE: 264
attattcccc attttgaagc ga                                              22
```

-continued

<210> SEQ ID NO 265
<211> LENGTH: 21
<212> TYPE: DNA
<213> ORGANISM: artificial
<220> FEATURE:
<223> OTHER INFORMATION: PHM11125 external reverse primer

<400> SEQUENCE: 265
ttttgggaat aagtgcgcga a                                                  21

<210> SEQ ID NO 266
<211> LENGTH: 21
<212> TYPE: DNA
<213> ORGANISM: artificial
<220> FEATURE:
<223> OTHER INFORMATION: PHM13958 external forward primer

<400> SEQUENCE: 266
caagatccgc aagtattatg a                                                  21

<210> SEQ ID NO 267
<211> LENGTH: 19
<212> TYPE: DNA
<213> ORGANISM: artificial
<220> FEATURE:
<223> OTHER INFORMATION: PHM13958 internal forward primer

<400> SEQUENCE: 267
tgcattagca actttcggc                                                     19

<210> SEQ ID NO 268
<211> LENGTH: 20
<212> TYPE: DNA
<213> ORGANISM: artificial
<220> FEATURE:
<223> OTHER INFORMATION: PHM13958 internal reverse primer

<400> SEQUENCE: 268
cctaaagttt ctggatgtgg                                                    20

<210> SEQ ID NO 269
<211> LENGTH: 22
<212> TYPE: DNA
<213> ORGANISM: artificial
<220> FEATURE:
<223> OTHER INFORMATION: PHM13958 external reverse primer

<400> SEQUENCE: 269
atacactgta agacagctaa ag                                                 22

<210> SEQ ID NO 270
<211> LENGTH: 18
<212> TYPE: DNA
<213> ORGANISM: artificial
<220> FEATURE:
<223> OTHER INFORMATION: PHM10468 external forward primer

<400> SEQUENCE: 270
cgggacacct gtcaagta                                                      18

<210> SEQ ID NO 271
<211> LENGTH: 20
<212> TYPE: DNA
<213> ORGANISM: artificial
<220> FEATURE:

<223> OTHER INFORMATION: PHM10468 internal forward primer

<400> SEQUENCE: 271
gaccagagga tgtcgatgaa                                          20

<210> SEQ ID NO 272
<211> LENGTH: 20
<212> TYPE: DNA
<213> ORGANISM: artificial
<220> FEATURE:
<223> OTHER INFORMATION: PHM10468 internal reverse primer

<400> SEQUENCE: 272
gacgatgtca ttggtgtttg                                          20

<210> SEQ ID NO 273
<211> LENGTH: 22
<212> TYPE: DNA
<213> ORGANISM: artificial
<220> FEATURE:
<223> OTHER INFORMATION: PHM10468 external reverse primer

<400> SEQUENCE: 273
caataaaggt ttgtcttcca gc                                       22

<210> SEQ ID NO 274
<211> LENGTH: 22
<212> TYPE: DNA
<213> ORGANISM: artificial
<220> FEATURE:
<223> OTHER INFORMATION: PHM12706 external forward primer

<400> SEQUENCE: 274
atcatcatct ggtaatttcc ct                                       22

<210> SEQ ID NO 275
<211> LENGTH: 20
<212> TYPE: DNA
<213> ORGANISM: artificial
<220> FEATURE:
<223> OTHER INFORMATION: PHM12706 internal forward primer

<400> SEQUENCE: 275
aatgccctaa gagtcaccaa                                          20

<210> SEQ ID NO 276
<211> LENGTH: 20
<212> TYPE: DNA
<213> ORGANISM: artificial
<220> FEATURE:
<223> OTHER INFORMATION: PHM12706 internal reverse primer

<400> SEQUENCE: 276
gattcagtgt ccagactctc                                          20

<210> SEQ ID NO 277
<211> LENGTH: 22
<212> TYPE: DNA
<213> ORGANISM: artificial
<220> FEATURE:
<223> OTHER INFORMATION: PHM12706 external reverse primer

<400> SEQUENCE: 277
acagattccc gatattccaa ca                                       22

```
<210> SEQ ID NO 278
<211> LENGTH: 18
<212> TYPE: DNA
<213> ORGANISM: artificial
<220> FEATURE:
<223> OTHER INFORMATION: PHM405 external forward primer

<400> SEQUENCE: 278
cgcttcgtcg gcatggac                                                 18

<210> SEQ ID NO 279
<211> LENGTH: 20
<212> TYPE: DNA
<213> ORGANISM: artificial
<220> FEATURE:
<223> OTHER INFORMATION: PHM405 internal forward primer

<400> SEQUENCE: 279
tgatgatgac tacgacgacc                                               20

<210> SEQ ID NO 280
<211> LENGTH: 20
<212> TYPE: DNA
<213> ORGANISM: artificial
<220> FEATURE:
<223> OTHER INFORMATION: PHM405 internal reverse primer

<400> SEQUENCE: 280
caccaactct ctctgtgtac                                               20

<210> SEQ ID NO 281
<211> LENGTH: 20
<212> TYPE: DNA
<213> ORGANISM: artificial
<220> FEATURE:
<223> OTHER INFORMATION: PHM405 external reverse primer

<400> SEQUENCE: 281
ctttctggca cccttgttta                                               20

<210> SEQ ID NO 282
<211> LENGTH: 22
<212> TYPE: DNA
<213> ORGANISM: artificial
<220> FEATURE:
<223> OTHER INFORMATION: PHM12025 external forward primer

<400> SEQUENCE: 282
tctggataat ggtaatcctg at                                            22

<210> SEQ ID NO 283
<211> LENGTH: 19
<212> TYPE: DNA
<213> ORGANISM: artificial
<220> FEATURE:
<223> OTHER INFORMATION: PHM12025 internal forward primer

<400> SEQUENCE: 283
tggataatgg taatcctga                                                19

<210> SEQ ID NO 284
<211> LENGTH: 20
<212> TYPE: DNA
<213> ORGANISM: artificial
<220> FEATURE:
<223> OTHER INFORMATION: PHM12025 internal reverse primer
```

```
<400> SEQUENCE: 284
tgatatttcg cctgtggtag                                              20

<210> SEQ ID NO 285
<211> LENGTH: 19
<212> TYPE: DNA
<213> ORGANISM: artificial
<220> FEATURE:
<223> OTHER INFORMATION: PHM12025 external reverse primer

<400> SEQUENCE: 285
attgatgggt gctgcctct                                               19

<210> SEQ ID NO 286
<211> LENGTH: 20
<212> TYPE: DNA
<213> ORGANISM: artificial
<220> FEATURE:
<223> OTHER INFORMATION: PHM18693-9-Forward primer

<400> SEQUENCE: 286
caaccgccag ggcattgaga                                              20

<210> SEQ ID NO 287
<211> LENGTH: 32
<212> TYPE: DNA
<213> ORGANISM: artificial
<220> FEATURE:
<223> OTHER INFORMATION: PHM18693-9-Reverse primer

<400> SEQUENCE: 287
tgcctcaggt taaaaagaga aacatgtaac ct                                32

<210> SEQ ID NO 288
<211> LENGTH: 30
<212> TYPE: DNA
<213> ORGANISM: artificial
<220> FEATURE:
<223> OTHER INFORMATION: PHM18693-9-Probe for allele 1

<400> SEQUENCE: 288
acggacgcgg agttatcata tgcggtgttg                                   30

<210> SEQ ID NO 289
<211> LENGTH: 28
<212> TYPE: DNA
<213> ORGANISM: artificial
<220> FEATURE:
<223> OTHER INFORMATION: PHM18693-9-Probe for allele 2

<400> SEQUENCE: 289
cgcgccgagg ctatcatatg cggtgttg                                     28

<210> SEQ ID NO 290
<211> LENGTH: 18
<212> TYPE: DNA
<213> ORGANISM: artificial
<220> FEATURE:
<223> OTHER INFORMATION: PHM10786-11-Forward primer

<400> SEQUENCE: 290
caggacctgc agcagggt                                                18

<210> SEQ ID NO 291
<211> LENGTH: 29
```

-continued

<212> TYPE: DNA
<213> ORGANISM: artificial
<220> FEATURE:
<223> OTHER INFORMATION: PHM10786-11-Reverse primer

<400> SEQUENCE: 291
agtgtgcaga tggaagtgag atcttcttg                                29

<210> SEQ ID NO 292
<211> LENGTH: 25
<212> TYPE: DNA
<213> ORGANISM: artificial
<220> FEATURE:
<223> OTHER INFORMATION: PHM10786-11-Probe for allele 1

<400> SEQUENCE: 292
acggacgcgg agaacagctg ccagc                                    25

<210> SEQ ID NO 293
<211> LENGTH: 23
<212> TYPE: DNA
<213> ORGANISM: artificial
<220> FEATURE:
<223> OTHER INFORMATION: PHM10786-11-Probe for allele 2

<400> SEQUENCE: 293
cgcgccgagg cacagctgcc agc                                      23

<210> SEQ ID NO 294
<211> LENGTH: 19
<212> TYPE: DNA
<213> ORGANISM: artificial
<220> FEATURE:
<223> OTHER INFORMATION: PHM10786-5-Forward primer

<400> SEQUENCE: 294
tcatcgccct cgaatggcg                                           19

<210> SEQ ID NO 295
<211> LENGTH: 25
<212> TYPE: DNA
<213> ORGANISM: artificial
<220> FEATURE:
<223> OTHER INFORMATION: PHM10786-5-Reverse primer

<400> SEQUENCE: 295
tccgagctcc tttcctactc gtaca                                    25

<210> SEQ ID NO 296
<211> LENGTH: 23
<212> TYPE: DNA
<213> ORGANISM: artificial
<220> FEATURE:
<223> OTHER INFORMATION: PHM10786-5-Probe for allele 1

<400> SEQUENCE: 296
acggacgcgg agcggcgggg tcc                                      23

<210> SEQ ID NO 297
<211> LENGTH: 21
<212> TYPE: DNA
<213> ORGANISM: artificial
<220> FEATURE:
<223> OTHER INFORMATION: PHM10786-5-Probe for allele 2

<400> SEQUENCE: 297

-continued cgcgccgagg aggcggggtc c                                              21

<210> SEQ ID NO 298
<211> LENGTH: 17
<212> TYPE: DNA
<213> ORGANISM: artificial
<220> FEATURE:
<223> OTHER INFORMATION: PHM10786-6-Forward primer

<400> SEQUENCE: 298
cgggcagctg gaccagg                                                   17

<210> SEQ ID NO 299
<211> LENGTH: 18
<212> TYPE: DNA
<213> ORGANISM: artificial
<220> FEATURE:
<223> OTHER INFORMATION: PHM10786-6-Reverse primer

<400> SEQUENCE: 299
cctgcccgtc ctaagcgg                                                  18

<210> SEQ ID NO 300
<211> LENGTH: 26
<212> TYPE: DNA
<213> ORGANISM: artificial
<220> FEATURE:
<223> OTHER INFORMATION: PHM10786-6-Probe for allele 1

<400> SEQUENCE: 300
acggacgcgg agtgacgaac ggagcg                                         26

<210> SEQ ID NO 301
<211> LENGTH: 23
<212> TYPE: DNA
<213> ORGANISM: artificial
<220> FEATURE:
<223> OTHER INFORMATION: PHM10786-6-Probe for allele 2

<400> SEQUENCE: 301
cgcgccgagg cgacgaacgg agc                                            23

<210> SEQ ID NO 302
<211> LENGTH: 24
<212> TYPE: DNA
<213> ORGANISM: artificial
<220> FEATURE:
<223> OTHER INFORMATION: PHM8057-801-Forward primer

<400> SEQUENCE: 302
cgtcttcagg atcactcccc ctct                                           24

<210> SEQ ID NO 303
<211> LENGTH: 30
<212> TYPE: DNA
<213> ORGANISM: artificial
<220> FEATURE:
<223> OTHER INFORMATION: PHM8057-801-Reverse primer

<400> SEQUENCE: 303
tcacctcgac gaagaaatct gcattattcg                                     30

<210> SEQ ID NO 304
<211> LENGTH: 29
<212> TYPE: DNA
<213> ORGANISM: artificial

```
<220> FEATURE:
<223> OTHER INFORMATION: PHM8057-801-Probe for allele 1

<400> SEQUENCE: 304
acggacgcgg agtgaatgaa tctctgggg                                          29

<210> SEQ ID NO 305
<211> LENGTH: 27
<212> TYPE: DNA
<213> ORGANISM: artificial
<220> FEATURE:
<223> OTHER INFORMATION: PHM8057-801-Probe for allele 2

<400> SEQUENCE: 305
cgcgccgagg cgaatgaatc tctgggg                                            27

<210> SEQ ID NO 306
<211> LENGTH: 25
<212> TYPE: DNA
<213> ORGANISM: artificial
<220> FEATURE:
<223> OTHER INFORMATION: PHM4044-11-Forward primer

<400> SEQUENCE: 306
tgaggtggag gaagtcgttg atgtc                                              25

<210> SEQ ID NO 307
<211> LENGTH: 39
<212> TYPE: DNA
<213> ORGANISM: artificial
<220> FEATURE:
<223> OTHER INFORMATION: PHM4044-11-Reverse primer
<220> FEATURE:
<221> NAME/KEY: misc_feature
<222> LOCATION: (13)..(13)
<223> OTHER INFORMATION: n is a, c, g, or t

<400> SEQUENCE: 307
tgaactttaa cancaacagg aaagaaatca acagattct                               39

<210> SEQ ID NO 308
<211> LENGTH: 30
<212> TYPE: DNA
<213> ORGANISM: artificial
<220> FEATURE:
<223> OTHER INFORMATION: PHM4044-11-Probe for allele 1

<400> SEQUENCE: 308
acggacgcgg agagcaagaa cttcttgacg                                         30

<210> SEQ ID NO 309
<211> LENGTH: 28
<212> TYPE: DNA
<213> ORGANISM: artificial
<220> FEATURE:
<223> OTHER INFORMATION: PHM4044-11-Probe for allele 2

<400> SEQUENCE: 309
cgcgccgagg tgcaagaact tcttgacg                                           28

<210> SEQ ID NO 310
<211> LENGTH: 22
<212> TYPE: DNA
<213> ORGANISM: artificial
<220> FEATURE:
<223> OTHER INFORMATION: PHM14080-16-Forward primer
```

<400> SEQUENCE: 310
cgagattgat gccgtgtcgt gg        22

<210> SEQ ID NO 311
<211> LENGTH: 34
<212> TYPE: DNA
<213> ORGANISM: artificial
<220> FEATURE:
<223> OTHER INFORMATION: PHM14080-16-Reverse primer

<400> SEQUENCE: 311
cacaatrgct agctgctaat tctgcactag taga        34

<210> SEQ ID NO 312
<211> LENGTH: 29
<212> TYPE: DNA
<213> ORGANISM: artificial
<220> FEATURE:
<223> OTHER INFORMATION: PHM14080-16-Probe for allele 1

<400> SEQUENCE: 312
acggacgcgg agcgcgttac cttcatctt        29

<210> SEQ ID NO 313
<211> LENGTH: 28
<212> TYPE: DNA
<213> ORGANISM: artificial
<220> FEATURE:
<223> OTHER INFORMATION: PHM14080-16-Probe for allele 2

<400> SEQUENCE: 313
cgcgccgagg tgcgttacct tcatcttg        28

<210> SEQ ID NO 314
<211> LENGTH: 15
<212> TYPE: DNA
<213> ORGANISM: artificial
<220> FEATURE:
<223> OTHER INFORMATION: PHM15089-10-Forward primer

<400> SEQUENCE: 314
gcggagcccg ggtct        15

<210> SEQ ID NO 315
<211> LENGTH: 27
<212> TYPE: DNA
<213> ORGANISM: artificial
<220> FEATURE:
<223> OTHER INFORMATION: PHM15089-10-Reverse primer

<400> SEQUENCE: 315
ccggtggyga gtagcagtag tatcagt        27

<210> SEQ ID NO 316
<211> LENGTH: 28
<212> TYPE: DNA
<213> ORGANISM: artificial
<220> FEATURE:
<223> OTHER INFORMATION: PHM15089-10-Probe for allele 1

<400> SEQUENCE: 316
acggacgcgg agcattacct gcccatgg        28

<210> SEQ ID NO 317
<211> LENGTH: 26

```
<212> TYPE: DNA
<213> ORGANISM: artificial
<220> FEATURE:
<223> OTHER INFORMATION: PHM15089-10-Probe for allele 2

<400> SEQUENCE: 317
cgcgccgagg gattacctgc ccatgg                                          26

<210> SEQ ID NO 318
<211> LENGTH: 27
<212> TYPE: DNA
<213> ORGANISM: artificial
<220> FEATURE:
<223> OTHER INFORMATION: PHM9364-6-Forward primer

<400> SEQUENCE: 318
ggatacgaga ctgtcctcac ggatttc                                         27

<210> SEQ ID NO 319
<211> LENGTH: 22
<212> TYPE: DNA
<213> ORGANISM: artificial
<220> FEATURE:
<223> OTHER INFORMATION: PHM9364-6-Reverse primer

<400> SEQUENCE: 319 gccctttct cctcctgttg gt                                               22

<210> SEQ ID NO 320
<211> LENGTH: 28
<212> TYPE: DNA
<213> ORGANISM: artificial
<220> FEATURE:
<223> OTHER INFORMATION: PHM9364-6-Probe for allele 1

<400> SEQUENCE: 320
acggacgcgg agcatggacc atctccca                                        28

<210> SEQ ID NO 321
<211> LENGTH: 27
<212> TYPE: DNA
<213> ORGANISM: artificial
<220> FEATURE:
<223> OTHER INFORMATION: PHM9364-6-Probe for allele 2

<400> SEQUENCE: 321
cgcgccgagg tatggaccat ctcccag                                         27

<210> SEQ ID NO 322
<211> LENGTH: 25
<212> TYPE: DNA
<213> ORGANISM: artificial
<220> FEATURE:
<223> OTHER INFORMATION: PHM201-16-Forward primer

<400> SEQUENCE: 322
tgggcttgyt gyggyaactg gtgga                                           25

<210> SEQ ID NO 323
<211> LENGTH: 28
<212> TYPE: DNA
<213> ORGANISM: artificial
<220> FEATURE:
<223> OTHER INFORMATION: PHM201-16-Reverse primer

<400> SEQUENCE: 323
```
ggagaagcay gtacccttca gttcacac    28

<210> SEQ ID NO 324
<211> LENGTH: 29
<212> TYPE: DNA
<213> ORGANISM: artificial
<220> FEATURE:
<223> OTHER INFORMATION: PHM201-16-Probe for allele 1

<400> SEQUENCE: 324
acggacgcgg agttggtgaa cacsgacgc    29

<210> SEQ ID NO 325
<211> LENGTH: 26
<212> TYPE: DNA
<213> ORGANISM: artificial
<220> FEATURE:
<223> OTHER INFORMATION: PHM201-16-Probe for allele 2

<400> SEQUENCE: 325
cgcgccgagg ctggtgaaca csgacg    26

<210> SEQ ID NO 326
<211> LENGTH: 27
<212> TYPE: DNA
<213> ORGANISM: artificial
<220> FEATURE:
<223> OTHER INFORMATION: PHM201-17-Forward primer

<400> SEQUENCE: 326
tgtcgagttc atccatttgg ktaggcc    27

<210> SEQ ID NO 327
<211> LENGTH: 28
<212> TYPE: DNA
<213> ORGANISM: artificial
<220> FEATURE:
<223> OTHER INFORMATION: PHM201-17-Reverse primer

<400> SEQUENCE: 327
gggagaagca ygtacccttc agttcaca    28

<210> SEQ ID NO 328
<211> LENGTH: 27
<212> TYPE: DNA
<213> ORGANISM: artificial
<220> FEATURE:
<223> OTHER INFORMATION: PHM201-17-Probe for allele 1

<400> SEQUENCE: 328
acggacgcgg agggcgtcsg tgttcac    27

<210> SEQ ID NO 329
<211> LENGTH: 25
<212> TYPE: DNA
<213> ORGANISM: artificial
<220> FEATURE:
<223> OTHER INFORMATION: PHM201-17-Probe for allele 2

<400> SEQUENCE: 329
cgcgccgagg cgcgtcsgtg ttcac    25

<210> SEQ ID NO 330
<211> LENGTH: 30
<212> TYPE: DNA
<213> ORGANISM: artificial

-continued

```
<220> FEATURE:
<223> OTHER INFORMATION: PHM4861-20-Forward primer

<400> SEQUENCE: 330
tgttatttct ttcatgctcg gctagcatga                                          30

<210> SEQ ID NO 331
<211> LENGTH: 25
<212> TYPE: DNA
<213> ORGANISM: artificial
<220> FEATURE:
<223> OTHER INFORMATION: PHM4861-20-Reverse primer

<400> SEQUENCE: 331
rcatcacata ctccacccag ttggt                                               25

<210> SEQ ID NO 332
<211> LENGTH: 28
<212> TYPE: DNA
<213> ORGANISM: artificial
<220> FEATURE:
<223> OTHER INFORMATION: PHM4861-20-Probe for allele 1

<400> SEQUENCE: 332
acggacgcgg agaaagttgc atccacga                                            28

<210> SEQ ID NO 333
<211> LENGTH: 26
<212> TYPE: DNA
<213> ORGANISM: artificial
<220> FEATURE:
<223> OTHER INFORMATION: PHM4861-20-Probe for allele 2

<400> SEQUENCE: 333
cgcgccgagg caagttgcat ccacga                                              26

<210> SEQ ID NO 334
<211> LENGTH: 30
<212> TYPE: DNA
<213> ORGANISM: artificial
<220> FEATURE:
<223> OTHER INFORMATION: PHM4861-21-Forward primer

<400> SEQUENCE: 334
tgttatttct ttcatgctcg gctagcatga                                          30

<210> SEQ ID NO 335
<211> LENGTH: 25
<212> TYPE: DNA
<213> ORGANISM: artificial
<220> FEATURE:
<223> OTHER INFORMATION: PHM4861-21-Reverse primer

<400> SEQUENCE: 335
rcatcacata ctccacccag ttggt                                               25

<210> SEQ ID NO 336
<211> LENGTH: 28
<212> TYPE: DNA
<213> ORGANISM: artificial
<220> FEATURE:
<223> OTHER INFORMATION: PHM4861-21-Probe for allele 1

<400> SEQUENCE: 336
acggacgcgg aggtatgctg ctcacgag                                            28
```

```
<210> SEQ ID NO 337
<211> LENGTH: 26
<212> TYPE: DNA
<213> ORGANISM: artificial
<220> FEATURE:
<223> OTHER INFORMATION: PHM4861-21-Probe for allele 2

<400> SEQUENCE: 337
cgcgccgagg atatgctgct cacgag                                          26

<210> SEQ ID NO 338
<211> LENGTH: 18
<212> TYPE: DNA
<213> ORGANISM: artificial
<220> FEATURE:
<223> OTHER INFORMATION: PHM5421-5-Forward primer

<400> SEQUENCE: 338
tgctggtggc gtctgctg                                                   18

<210> SEQ ID NO 339
<211> LENGTH: 22
<212> TYPE: DNA
<213> ORGANISM: artificial
<220> FEATURE:
<223> OTHER INFORMATION: PHM5421-5-Reverse primer

<400> SEQUENCE: 339
gagcagcatg agctggaagt cc                                              22

<210> SEQ ID NO 340
<211> LENGTH: 24
<212> TYPE: DNA
<213> ORGANISM: artificial
<220> FEATURE:
<223> OTHER INFORMATION: PHM5421-5-Probe for allele 1

<400> SEQUENCE: 340
acggacgcgg agcccaggaa cgcc                                            24

<210> SEQ ID NO 341
<211> LENGTH: 23
<212> TYPE: DNA
<213> ORGANISM: artificial
<220> FEATURE:
<223> OTHER INFORMATION: PHM5421-5-Probe for allele 2

<400> SEQUENCE: 341
cgcgccgagg accaggaacg ccg                                             23

<210> SEQ ID NO 342
<211> LENGTH: 22
<212> TYPE: DNA
<213> ORGANISM: artificial
<220> FEATURE:
<223> OTHER INFORMATION: PHM4115-35-Forward primer

<400> SEQUENCE: 342
gggagcttgg tctccgatga ga                                              22

<210> SEQ ID NO 343
<211> LENGTH: 18
<212> TYPE: DNA
<213> ORGANISM: artificial
<220> FEATURE:
<223> OTHER INFORMATION: PHM4115-35-Reverse primer
```

```
<400> SEQUENCE: 343
tgctgcacag cgctgtcc                                                18

<210> SEQ ID NO 344
<211> LENGTH: 28
<212> TYPE: DNA
<213> ORGANISM: artificial
<220> FEATURE:
<223> OTHER INFORMATION: PHM4115-35-Probe for allele 1

<400> SEQUENCE: 344
acggacgcgg aggcgtggtt aacctgac                                     28

<210> SEQ ID NO 345
<211> LENGTH: 27
<212> TYPE: DNA
<213> ORGANISM: artificial
<220> FEATURE:
<223> OTHER INFORMATION: PHM4115-35-Probe for allele 2

<400> SEQUENCE: 345
cgcgccgagg tcgtggttaa cctgaca                                      27

<210> SEQ ID NO 346
<211> LENGTH: 43
<212> TYPE: DNA
<213> ORGANISM: artificial
<220> FEATURE:
<223> OTHER INFORMATION: PHM12521-18-Forward primer

<400> SEQUENCE: 346
acttgcttag ttgccatata catgaatmaa ctrgacaygg taa                    43

<210> SEQ ID NO 347
<211> LENGTH: 32
<212> TYPE: DNA
<213> ORGANISM: artificial
<220> FEATURE:
<223> OTHER INFORMATION: PHM12521-18-Reverse primer

<400> SEQUENCE: 347
gcacagtagc aagctgcaaa tattgtaaat ga                                32

<210> SEQ ID NO 348
<211> LENGTH: 29
<212> TYPE: DNA
<213> ORGANISM: artificial
<220> FEATURE:
<223> OTHER INFORMATION: PHM12521-18-Probe for allele 1

<400> SEQUENCE: 348
acggacgcgg agatgtgcga catattggt                                    29

<210> SEQ ID NO 349
<211> LENGTH: 27
<212> TYPE: DNA
<213> ORGANISM: artificial
<220> FEATURE:
<223> OTHER INFORMATION: PHM12521-18-Probe for allele 2

<400> SEQUENCE: 349
cgcgccgagg ctgtgcgaca tattggt                                      27

<210> SEQ ID NO 350
```

-continued

```
<211> LENGTH: 29
<212> TYPE: DNA
<213> ORGANISM: artificial
<220> FEATURE:
<223> OTHER INFORMATION: PHM12521-19-Forward primer

<400> SEQUENCE: 350
gttttgatcc ggagacctga ccaatatgt                                29

<210> SEQ ID NO 351
<211> LENGTH: 33
<212> TYPE: DNA
<213> ORGANISM: artificial
<220> FEATURE:
<223> OTHER INFORMATION: PHM12521-19-Reverse primer

<400> SEQUENCE: 351
ggacacattt cagtgtgata cagctataag cat                           33

<210> SEQ ID NO 352
<211> LENGTH: 31
<212> TYPE: DNA
<213> ORGANISM: artificial
<220> FEATURE:
<223> OTHER INFORMATION: PHM12521-19-Probe for allele 1

<400> SEQUENCE: 352
acggacgcgg agcgtcagtt caaacmtgtg c                             31

<210> SEQ ID NO 353
<211> LENGTH: 29
<212> TYPE: DNA
<213> ORGANISM: artificial
<220> FEATURE:
<223> OTHER INFORMATION: PHM12521-19-Probe for allele 2

<400> SEQUENCE: 353
cgcgccgagg tgtcagttca aacmtgtgc                                29

<210> SEQ ID NO 354
<211> LENGTH: 32
<212> TYPE: DNA
<213> ORGANISM: artificial
<220> FEATURE:
<223> OTHER INFORMATION: PHM12521-29-Forward primer

<400> SEQUENCE: 354
tcgcacakgt ttgaactgac rcttgtattc ct                            32

<210> SEQ ID NO 355
<211> LENGTH: 35
<212> TYPE: DNA
<213> ORGANISM: artificial
<220> FEATURE:
<223> OTHER INFORMATION: PHM12521-29-Reverse primer

<400> SEQUENCE: 355
ggacacattt cagtgtgata cagctataag catac                         35

<210> SEQ ID NO 356
<211> LENGTH: 27
<212> TYPE: DNA
<213> ORGANISM: artificial
<220> FEATURE:
<223> OTHER INFORMATION: PHM12521-29-Probe for allele 1

<400> SEQUENCE: 356
```

```
acggacgcgg agcgcacagt agcaagc                                              27

<210> SEQ ID NO 357
<211> LENGTH: 25
<212> TYPE: DNA
<213> ORGANISM: artificial
<220> FEATURE:
<223> OTHER INFORMATION: PHM12521-29-Probe for allele 2

<400> SEQUENCE: 357
cgcgccgagg tgcacagtag caagc                                                25

<210> SEQ ID NO 358
<211> LENGTH: 22
<212> TYPE: DNA
<213> ORGANISM: artificial
<220> FEATURE:
<223> OTHER INFORMATION: C00386-397-Forward primer

<400> SEQUENCE: 358
cgtcttccat cttccatggc gg                                                   22

<210> SEQ ID NO 359
<211> LENGTH: 14
<212> TYPE: DNA
<213> ORGANISM: artificial
<220> FEATURE:
<223> OTHER INFORMATION: C00386-397-Reverse primer

<400> SEQUENCE: 359
gccaccgccg ccac                                                            14

<210> SEQ ID NO 360
<211> LENGTH: 28
<212> TYPE: DNA
<213> ORGANISM: artificial
<220> FEATURE:
<223> OTHER INFORMATION: C000386-397-Probe for allele 1

<400> SEQUENCE: 360
acggacgcgg agaccgatca tagctcgc                                             28

<210> SEQ ID NO 361
<211> LENGTH: 25
<212> TYPE: DNA
<213> ORGANISM: artificial
<220> FEATURE:
<223> OTHER INFORMATION: C00386-397-Probe for allele 2

<400> SEQUENCE: 361
cgcgccgagg gccgatcata gctcg                                                25

<210> SEQ ID NO 362
<211> LENGTH: 29
<212> TYPE: DNA
<213> ORGANISM: artificial
<220> FEATURE:
<223> OTHER INFORMATION: PHM13418-18-Forward primer

<400> SEQUENCE: 362
cggttcatgt ttgtcytgca gagttctga                                            29

<210> SEQ ID NO 363
<211> LENGTH: 27
<212> TYPE: DNA
```

```
<213> ORGANISM: artificial
<220> FEATURE:
<223> OTHER INFORMATION: PHM13418-18-Reverse primer

<400> SEQUENCE: 363
gttgatggtc atcaacatgt gctgcaa                                           27

<210> SEQ ID NO 364
<211> LENGTH: 26
<212> TYPE: DNA
<213> ORGANISM: artificial
<220> FEATURE:
<223> OTHER INFORMATION: PHM13418-18-Probe for allele 1

<400> SEQUENCE: 364
cgcgccgagg agtgtcaccg gatgta                                            26

<210> SEQ ID NO 365
<211> LENGTH: 27
<212> TYPE: DNA
<213> ORGANISM: artificial
<220> FEATURE:
<223> OTHER INFORMATION: PHM13418-18-Probe for allele 2

<400> SEQUENCE: 365
acggacgcgg agggtgtcac cggatgt                                           27

<210> SEQ ID NO 366
<211> LENGTH: 23
<212> TYPE: DNA
<213> ORGANISM: artificial
<220> FEATURE:
<223> OTHER INFORMATION: PHM13418-10-Forward primer

<400> SEQUENCE: 366
ccctctccaa agtcccaggt aca                                               23

<210> SEQ ID NO 367
<211> LENGTH: 26
<212> TYPE: DNA
<213> ORGANISM: artificial
<220> FEATURE:
<223> OTHER INFORMATION: PHM13418-10-Reverse primer

<400> SEQUENCE: 367
acaaacatga accgagctta gggagt                                            26

<210> SEQ ID NO 368
<211> LENGTH: 27
<212> TYPE: DNA
<213> ORGANISM: artificial
<220> FEATURE:
<223> OTHER INFORMATION: PHM13418-10-Probe for allele 1

<400> SEQUENCE: 368
cgcgccgagg gcagcgaggt catattt                                           27

<210> SEQ ID NO 369
<211> LENGTH: 31
<212> TYPE: DNA
<213> ORGANISM: artificial
<220> FEATURE:
<223> OTHER INFORMATION: PHM13418-10-Probe for allele 2

<400> SEQUENCE: 369
acggacgcgg agacagcgag gtcatatttt c                                      31
```

-continued

<210> SEQ ID NO 370
<211> LENGTH: 22
<212> TYPE: DNA
<213> ORGANISM: artificial
<220> FEATURE:
<223> OTHER INFORMATION: PHM113-7-Forward primer

<400> SEQUENCE: 370
ggccggagat ctcattgcag gt                                              22

<210> SEQ ID NO 371
<211> LENGTH: 28
<212> TYPE: DNA
<213> ORGANISM: artificial
<220> FEATURE:
<223> OTHER INFORMATION: PHM113-7-Reverse primer

<400> SEQUENCE: 371
actcaaattg gttgccacaa crtggtca                                        28

<210> SEQ ID NO 372
<211> LENGTH: 25
<212> TYPE: DNA
<213> ORGANISM: artificial
<220> FEATURE:
<223> OTHER INFORMATION: PHM113-7-Probe for allele 1

<400> SEQUENCE: 372
cgcgccgagg ccttgaggtg gtgct                                           25

<210> SEQ ID NO 373
<211> LENGTH: 27
<212> TYPE: DNA
<213> ORGANISM: artificial
<220> FEATURE:
<223> OTHER INFORMATION: PHM113-7-Probe for allele 2

<400> SEQUENCE: 373
acggacgcgg agtcttgagg tggtgct                                         27

<210> SEQ ID NO 374
<211> LENGTH: 19
<212> TYPE: DNA
<213> ORGANISM: artificial
<220> FEATURE:
<223> OTHER INFORMATION: PHM10337-11-Forward primer

<400> SEQUENCE: 374
cctgcgtgat cctgaggcc                                                  19

<210> SEQ ID NO 375
<211> LENGTH: 27
<212> TYPE: DNA
<213> ORGANISM: artificial
<220> FEATURE:
<223> OTHER INFORMATION: PHM10337-11-Reverse primer

<400> SEQUENCE: 375
acaattctga aatgctcgct ccctagt                                         27

<210> SEQ ID NO 376
<211> LENGTH: 29
<212> TYPE: DNA
<213> ORGANISM: artificial
<220> FEATURE:

<223> OTHER INFORMATION: PHM10337-11-Probe for allele 1

<400> SEQUENCE: 376
acggacgcgg agtcaggtag gtaaaacgc                              29

<210> SEQ ID NO 377
<211> LENGTH: 27
<212> TYPE: DNA
<213> ORGANISM: artificial
<220> FEATURE:
<223> OTHER INFORMATION: PHM10337-11-Probe for allele 2

<400> SEQUENCE: 377
cgcgccgagg ccaggtaggt aaaacgc                                27

<210> SEQ ID NO 378
<211> LENGTH: 25
<212> TYPE: DNA
<213> ORGANISM: artificial
<220> FEATURE:
<223> OTHER INFORMATION: PHM16736-8-Forward primer

<400> SEQUENCE: 378
gcctgctcag gaaacactca tctct                                  25

<210> SEQ ID NO 379
<211> LENGTH: 33
<212> TYPE: DNA
<213> ORGANISM: artificial
<220> FEATURE:
<223> OTHER INFORMATION: PHM16736-8-Reverse primer

<400> SEQUENCE: 379
gttggtagca gttgttcttc attagcaagt aca                         33

<210> SEQ ID NO 380
<211> LENGTH: 31
<212> TYPE: DNA
<213> ORGANISM: artificial
<220> FEATURE:
<223> OTHER INFORMATION: PHM16736-8-Probe for allele 1

<400> SEQUENCE: 380
acggacgcgg agagaaactg tgttctcatg g                           31

<210> SEQ ID NO 381
<211> LENGTH: 29
<212> TYPE: DNA
<213> ORGANISM: artificial
<220> FEATURE:
<223> OTHER INFORMATION: PHM16736-8-Probe for allele 2

<400> SEQUENCE: 381
cgcgccgagg tgaaactgtg ttctcatgg                              29

<210> SEQ ID NO 382
<211> LENGTH: 28
<212> TYPE: DNA
<213> ORGANISM: artificial
<220> FEATURE:
<223> OTHER INFORMATION: PHM12025-48-Forward primer

<400> SEQUENCE: 382
tgtttggttc gctactagct tgttacgt                               28

-continued

<210> SEQ ID NO 383
<211> LENGTH: 33
<212> TYPE: DNA
<213> ORGANISM: artificial
<220> FEATURE:
<223> OTHER INFORMATION: PHM12025-48-Reverse primer

<400> SEQUENCE: 383
ggttgcatga ggattatagg agattgagga gta                         33

<210> SEQ ID NO 384
<211> LENGTH: 32
<212> TYPE: DNA
<213> ORGANISM: artificial
<220> FEATURE:
<223> OTHER INFORMATION: PHM12025-48-Probe for allele 1

<400> SEQUENCE: 384
acggacgcgg agtgaaccaa acagactcat aa                          32

<210> SEQ ID NO 385
<211> LENGTH: 27
<212> TYPE: DNA
<213> ORGANISM: artificial
<220> FEATURE:
<223> OTHER INFORMATION: PHM12025-48-Probe for allele 2

<400> SEQUENCE: 385
cgcgccgagg cgaaccaaac agactca                                27

<210> SEQ ID NO 386
<211> LENGTH: 17
<212> TYPE: DNA
<213> ORGANISM: artificial
<220> FEATURE:
<223> OTHER INFORMATION: PHM11186-16-Forward primer

<400> SEQUENCE: 386
cgacgagctg gagcgcc                                           17

<210> SEQ ID NO 387
<211> LENGTH: 19
<212> TYPE: DNA
<213> ORGANISM: artificial
<220> FEATURE:
<223> OTHER INFORMATION: PHM11186-16-Reverse primer

<400> SEQUENCE: 387
gcgycgcttg tcggtggtg                                         19

<210> SEQ ID NO 388
<211> LENGTH: 25
<212> TYPE: DNA
<213> ORGANISM: artificial
<220> FEATURE:
<223> OTHER INFORMATION: PHM11186-16-Probe for allele 1

<400> SEQUENCE: 388
acggacgcgg agacaggggc ggaag                                  25

<210> SEQ ID NO 389
<211> LENGTH: 21
<212> TYPE: DNA
<213> ORGANISM: artificial
<220> FEATURE:
<223> OTHER INFORMATION: PHM11186-16-Probe for allele 2

```
<400> SEQUENCE: 389
cgcgccgagg gcaggggcgg a                                              21
```

GENETIC LOCI ASSOCIATED WITH MECHANICAL STALK STRENGTH IN MAIZE

CROSS-REFERENCE TO RELATED APPLICATION

This application claims the benefit of U.S. Provisional Application No. 61/080,783, filed Jul. 15, 2008, which is incorporated by reference in its entirety.

FIELD OF THE INVENTION

The present disclosure relates to compositions and methods useful in enhancing mechanical stalk strength in maize plants.

BACKGROUND OF THE INVENTION

In maize, stalk lodging, or stalk breakage, accounts for significant annual yield losses in the United States. During a maize plant's vegetative growth phase, rapid growth weakens cell walls, making stalk tissue brittle and increasing the propensity for stalks to snap when exposed to strong, sudden winds and/or other weather conditions. This type of stalk lodging, called green snap or brittle snap, typically occurs at the V5 to V8 stage, when the growing point of a maize plant is emerging from the soil line, or at the V12 to R1 stage, about two weeks prior to tasseling and until just after silking. Another type of stalk lodging, late season stalk lodging occurs near harvest when the stalk cannot support the weight of the ear. Factors that weaken the stalk during late season include insect attack, such as the European corn borer tunneling into stalk and ear shanks, and infection by pathogens such as *Colletotrichum graminicola*, the causative agent in Anthracnose stalk rot. Adverse fall weather conditions also contribute to late season stalk lodging.

The mechanical strength of the maize stalk plays a major role in a plant's resistance to all types of stalk lodging, and therefore, is of great value to the farmer. Enhancing overall mechanical stalk strength in maize will make stalks stronger during both vegetative development and late season, thereby reducing yield and grain quality losses. Moreover, maize plants with increased mechanical stalk strength can remain in the field for longer periods of time, allowing farmers to delay harvest, if necessary.

Selection through the use of molecular markers associated with mechanical stalk strength has the advantage of permitting at least some selection based solely on the genetic composition of the progeny, and selections can be made very early on in the plant life cycle, even as early as the seed stage. The increased rate of selection that can be obtained through the use of molecular markers associated with mechanical stalk strength means that plant breeding for increased mechanical stalk strength can occur more rapidly.

It is desirable to provide compositions and methods for identifying and selecting maize plants that display overall increased mechanical stalk strength.

SUMMARY

Compositions and methods for selecting maize plants with mechanical stalk strength characteristics are provided herein, including compositions and methods for identifying and selecting maize plants with increased mechanical stalk strength and compositions and methods for identifying and counter-selecting maize plants that have decreased mechanical stalk strength.

In one embodiment, methods of selecting a maize plant or germplasm with mechanical stalk strength characteristics are provided. In these methods, DNA is obtained, and the presence of at least one marker allele is detected. The marker allele can include any marker allele that is linked to and associated with any of the following marker alleles: a "G" at PHM3468.1, a "T" at PHM3468.4, a "G" at PHM3468.18, a "T" at PHM12521.12, a "C" at PHM10840.105, an "A" at PHM10840.118, a "C" at PHM10840.130, a "C" at PHM16736.6, an "A" at PHM16736.14, a "C" at PHM14053.7, a "C" at PHM14053.8, a "C" at PHM14053.14, a "T" at PHM405.35, a "C" at PHM12025.26, a "T" at PHM18693-9-U, a "G" at PHM10786-11-U, a "C" at PHM10786-5-U, a "T" at PHM10786-6-U, a "G" at PHM8057-801-U, a "C" at PHM201-16-U, a "C" or a "G" at PHM201-17-U, a "T" or a "G" at PHM4861-20-U, an "A" at PHM4861-21-U, a "G" at PHM5421-5-V, a "G" or a "T" at PHM4115-35-U, a "T" at PHM12521-18-U, an "A" at PHM12521-19-U, a "G" at PHM12521-29-U, a "C" at C00386-397-U, a "C" at PHM13418-18, a "C" at PHM13418-10, a "T" at PHM113-7, a "T" at PHM10337-11-U, an "A" at PHM16736-8-V, a "C" at PHM12025-48, and a "T" at PHM11186-16-V. A maize plant or germplasm that has the marker allele linked to and associated with any of the marker alleles listed above is then selected.

In other embodiments, the marker allele can be linked to any of the following marker alleles: a "G" at PHM3468.1, a "T" at PHM3468.4, a "G" at PHM3468.18, a "T" at PHM12521.12, a "C" at PHM10840.105, an "A" at PHM10840.118, a "C" at PHM10840.130, a "C" at PHM16736.6, an "A" at PHM16736.14, a "C" at PHM14053.7, a "C" at PHM14053.8, a "C" at PHM14053.14, a "T" at PHM405.35, a "C" at PHM12025.26, a "T" at PHM18693-9-U, a "G" at PHM10786-11-U, a "C" at PHM10786-5-U, a "T" at PHM10786-6-U, a "G" at PHM8057-801-U, a "C" at PHM201-16-U, a "C" or a "G" at PHM201-17-U, a "T" or a "G" at PHM4861-20-U, an "A" at PHM4861-21-U, a "G" at PHM5421-5-V, a "G" or a "T" at PHM4115-35-U, a "T" at PHM12521-18-U, an "A" at PHM12521-19-U, a "G" at PHM12521-29-U, a "C" at C00386-397-U, a "C" at PHM13418-18, a "C" at PHM13418-10, a "T" at PHM113-7, a "T" at PHM10337-11-U, an "A" at PHM16736-8-V, a "C" at PHM12025-48, and a "T" at PHM11186-16-V by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM.

In other embodiments, the marker allele can be any of the following marker alleles: a "G" at PHM3468.1, a "T" at PHM3468.4, a "G" at PHM3468.18, a "T" at PHM12521.12, a "C" at PHM10840.105, an "A" at PHM10840.118, a "C" at PHM10840.130, a "C" at PHM16736.6, an "A" at PHM16736.14, a "C" at PHM14053.7, a "C" at PHM14053.8, a "C" at PHM14053.14, a "T" at PHM405.35, a "C" at PHM12025.26, a "T" at PHM18693-9-U, a "G" at PHM10786-11-U, a "C" at PHM10786-5-U, a "T" at PHM10786-6-U, a "G" at PHM8057-801-U, a "C" at PHM201-16-U, a "C" or a "G" at PHM201-17-U, a "T" or a "G" at PHM4861-20-U, an "A" at PHM4861-21-U, a "G" at PHM5421-5-V, a "G" or a "T" at PHM4115-35-U, a "T" at PHM12521-18-U, an "A" at PHM12521-19-U, a "G" at PHM12521-29-U, a "C" at C00386-397-U, a "C" at PHM13418-18, a "C" at PHM13418-10, a "T" at PHM113-7, a "T" at PHM10337-11-U, an "A" at PHM16736-8-V, a "C" at PHM12025-48, and a "T" at PHM11186-16-V.

In another embodiment, methods of selecting a maize plant or germplasm with mechanical stalk strength characteristics are provided. In these methods, DNA is obtained, and the absence of at least one marker allele is detected. The marker allele can include any marker allele that is linked to and associated with any of the following marker alleles: a "T" at PHM2130.24, an "A" at PHM2130.29, a "C" at PHM2130.30, a "G" at PHM2130.33, a "G" at PHM15089.13, a "C" at PHM12706.14, a "C" at PHM201.10, an "A" at PHM201.18, a "T" at PHM4044-11-U, an "A" at PHM14080-16-V, a "C" at PHM15089-10-U, and a "G" at PHM9364-6-U. A maize plant or germplasm that does not have the marker allele linked to and associated with any of the marker alleles listed above is then selected.

In other embodiments, the marker allele can be linked to any of the following marker alleles: a "T" at PHM2130.24, an "A" at PHM2130.29, a "C" at PHM2130.30, a "G" at PHM2130.33, a "G" at PHM15089.13, a "C" at PHM12706.14, a "C" at PHM201.10, an "A" at PHM201.18, a "T" at PHM4044-11-U, an "A" at PHM14080-16-V, a "C" at PHM15089-10-U, and a "G" at PHM9364-6-U, by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM.

In other embodiments, the marker allele can be any of the following marker alleles: a "T" at PHM2130.24, an "A" at PHM2130.29, a "C" at PHM2130.30, a "G" at PHM2130.33, a "G" at PHM15089.13, a "C" at PHM12706.14, a "C" at PHM201.10, an "A" at PHM201.18, a "T" at PHM4044-11-U, an "A" at PHM14080-16-V, a "C" at PHM15089-10-U, and a "G" at PHM9364-6-U.

In another embodiment, methods for identifying maize plants with increased or decreased mechanical stalk strength by detecting at least one marker allele associated with increased or decreased mechanical stalk strength in the germplasm of a maize plant are provided. The marker locus can be selected from any of the marker loci provided in Table 3 or Table 7, as well as any other marker that is linked to these markers. The marker locus can be found within any of the following chromosomal intervals on linkage group 5, comprising and flanked by:
 (i) PHM654 and PHM6727;
 (ii) PHM12632 and PHM3323;
 (iii) PHM201 and PHM3323; and
 (iv) PHM201 and PHM3468.

More than one marker locus can be selected in the same plant with no limitation as to which markers are selected in combination. The markers used in combinations can be any of the markers in Table 3 or Table 7, any other marker linked to the markers in Table 3 or Table 7 (e.g., the linked markers determined from the Maize GDB resource), or any marker within the intervals described herein.

In another embodiment, methods of selecting maize plants with increased mechanical stalk strength are provided. In one aspect, a first maize plant is obtained that has at least one allele of a marker locus wherein the allele is associated with increased mechanical stalk strength. The marker locus can be found within any of the following chromosomal intervals on linkage group 5, comprising and flanked by:
 (i) PHM654 and PHM6727;
 (ii) PHM12632 and PHM3323;
 (iii) PHM201 and PHM3323; or
 (iv) PHM201 and PHM3468.

The first maize plant is crossed to a second maize plant, and the progeny plants resulting from the cross are evaluated for the allele of the first maize plant. Progeny plants that possess the allele from the first maize plant can then be selected as having increased mechanical stalk strength.

In another embodiment, methods for not selecting plants with decreased mechanical stalk strength are provided. In one aspect, a first maize plant is obtained that has at least one allele of a marker locus wherein the allele is associated with decreased mechanical stalk strength. The marker locus can be found within any of the following chromosomal intervals on linkage group 5, comprising and flanked by:
 (i) PHM654 and PHM6727;
 (ii) PHM12632 and PHM3323;
 (iii) PHM201 and PHM3323; and
 (iv) PHM201 and PHM3468.

The first maize plant is crossed to a second maize plant, and the progeny plants resulting from the cross are evaluated for the allele of the first maize plant. Progeny plants that possess the allele from the first maize plant can be identified as having decreased mechanical stalk strength and can be removed from a breeding program or planting.

In another embodiment, methods for selecting a maize plant with mechanical stalk strength characteristics are provided in which at least one marker locus is assayed within the maize plant. The marker locus can be located:
 a. on chromosome 1, within the interval comprising and flanked by PHM7844 and PHM8029;
 b. on chromosome 1, within the interval comprising and flanked by PHM7844 and PHM574;
 c. on chromosome 1, within the interval comprising and flanked by PHM11754 and PHM1481;
 d. on chromosome 1, within the interval comprising and flanked by PHM6427 and PHM1481;
 e. on chromosome 1, within the interval comprising and flanked by PHM11125 and PHM13958;
 f. on chromosome 1, within the interval comprising and flanked by PHM10468 and PHM13958;
 g. on chromosome 9, within the interval comprising and flanked by PHM4578 and PHM11186; or
 h. on chromosome 9, within the interval comprising and flanked by PHM14053 and PHM16736; and is associated with mechanical stalk strength. The maize plant is then selected if it possesses a favorable allele at the marker locus.

In another embodiment, methods for selecting a maize plant with mechanical stalk strength characteristics are provided in which at least one marker locus is assayed within the maize plant. The marker locus can be located:
 a. on chromosome 1, within the interval comprising and flanked by PHM7844 and PHM8029;
 b. on chromosome 1, within the interval comprising and flanked by PHM7844 and PHM574;
 c. on chromosome 1, within the interval comprising and flanked by PHM11754 and PHM1481;
 d. on chromosome 1, within the interval comprising and flanked by PHM6427 and PHM1481;
 e. on chromosome 1, within the interval comprising and flanked by PHM11125 and PHM13958;
 f. on chromosome 1, within the interval comprising and flanked by PHM10468 and PHM13958;
 g. on chromosome 9, within the interval comprising and flanked by PHM4578 and PHM11186; or
 h. on chromosome 9, within the interval comprising and flanked by PHM14053 and PHM16736; and is associated with mechanical stalk strength. The maize plant is then selected if it does not possess an unfavorable allele at the marker locus.

Maize plants identified or selected by any of the methods described herein are also included.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIGS. 1A-I show the physical map arrangement of sequenced BACs (obtained from the Maize Genome Browser, which is publicly available on the internet; http://www.maizesequence.org) that assemble to the chromosome 5 region defined by and including BACs c0216105 and c0117h02. The positions of the markers listed in Table 7 are also indicated.

FIG. 2A shows a structured association analysis, wherein chromosome 5 markers were tested for significance of association with mechanical stalk strength. Mechanical stalk strength values were obtained using an Instron™ machine and a three-point bend test, on a set of 189 lines. Stalk strength values were acquired from plants in late season. X axis: Distance expressed in cM on Chr. 5. Y axis: probability value.

FIG. 2B shows an association analysis of an NSS subpopulation, wherein chromosome 5 markers were tested for significance of association with mechanical stalk strength. The NSS subpopulation consisted of 60 lines, which varied in maturity from a CRM (comparative relative maturity) of 105 to a CRM of 110. Mechanical stalk strength values were obtained using an Instron™ machine and a three-point bend test and were acquired from plants in late season. X axis: Distance expressed in cM on Chr. 5. Y axis: probability value.

FIGS. 2C-E show the clusters of markers on chromosome 5 that co-segregate with mechanical stalk strength in the NSS subpopulation at the following p-levels: C) a p-level of ≤0.01 (white data points represent the region defined by and including PHM654 and PHM6727), D) a p-level of ≤0.001 (white data points represent the region defined by and including PHM12632 and PHM3323, and E) a p-level of ≤0.0001 (white data points represent the region defined by and including PHM201 and PHM3323). Black dots represent associated markers that do not fall within each respective cluster.

FIG. 3 shows associations between chromosome 9 marker loci and mechanical stalk strength in the NSS subpopulation. The NSS subpopulation consisted of 60 lines, which varied in maturity from a CRM (comparative relative maturity) of 105 to a CRM of 110. Mechanical stalk strength values were obtained using an Instron™ machine and a three-point bend test and were acquired from plants in late season. X axis: Distance expressed in cM on Chr. 9. Y axis: probability value.

FIG. 4 shows associations between chromosome 1 marker loci and mechanical stalk strength in the NSS subpopulation. The NSS subpopulation consisted of 60 lines, which varied in maturity from a CRM (comparative relative maturity) of 105 to a CRM of 110. Mechanical stalk strength values were obtained using an Instron™ machine and a three-point bend test and were acquired from plants in late season. X axis: Distance expressed in cM on Chr. 1. Y axis: probability value.

FIG. 5 shows the PHM marker alleles for A) PHM201, B) PHM5421, and C) PHM3468. The positions of the polymorphisms relative to the reference sequence are represented in the numbers at the top of each table.

FIG. 6 depicts a plot of the average mechanical stalk strength values for: A) haplotypes constituting marker alleles at PHM201 and at PHM5421 and B) PHM3468 marker alleles.

Figure 2:
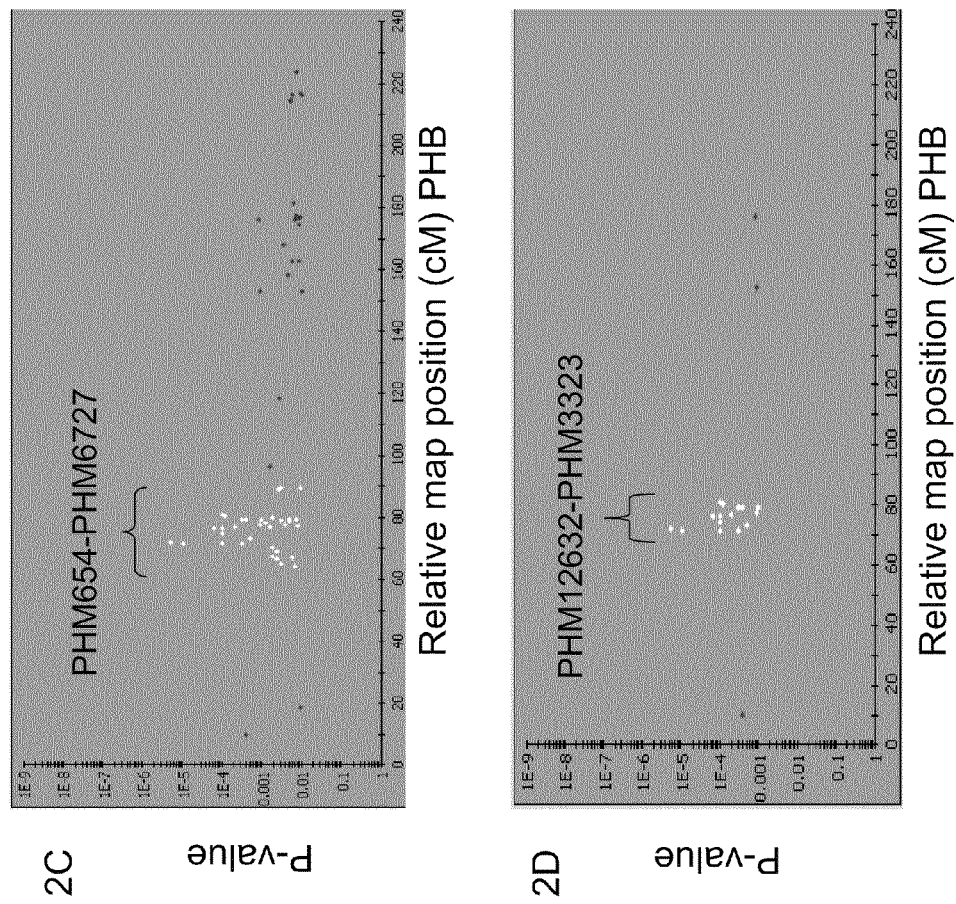
Figure 2:
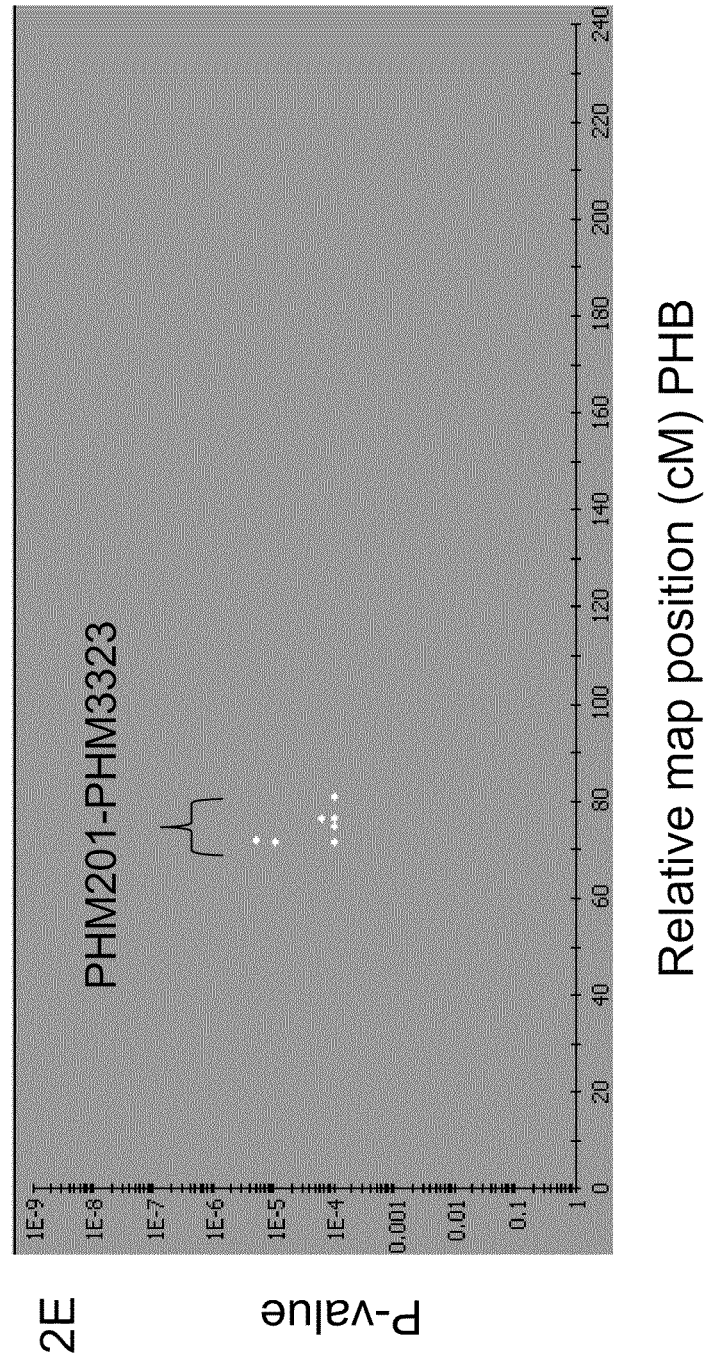

FIG. 7 shows the composite interval mapping results for data set 1 (portable Instron™ data) using the B73×Mo17 (IBM) syn4 population. A peak of significance was identified on chromosome 5. Marker positions on the x-axis correspond to the modified IBM2 genetic map. The y-axis represents the LOD score.

FIG. 8 shows the composite interval mapping results for data set 2 (device and method described in patent application US2007/0125155 (published Jun. 6, 2007)) using the B73×Mo17 (IBM) syn4 population. A peak of significance was identified on chromosome 5. Marker positions on the x-axis correspond to the modified IBM2 genetic map. The y-axis represents the LOD score.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists the sequences described herein that are associated with the PHM markers, along with the corresponding identifiers (SEQ ID NO:) as used in the attached Sequence Listing.

TABLE 1

PHM Marker Sequences

| Marker Locus | Reference sequence (SEQ ID NO:) | | Forward (SEQ ID NO:) | Reverse (SEQ ID NO:) |
|---|---|---|---|---|
| PHM654 | 1 | Internal | 40 | 41 |
|  |  | External | 42 | 43 |
| PHM111 | 2 | Internal | 44 | 45 |
|  |  | External | 46 | 47 |
| PHM10100 | 3 | Internal | 48 | 49 |
|  |  | External | 50 | 51 |
| PHM7357 | 4 | Internal | 52 | 53 |
|  |  | External | 54 | 55 |
| PHM5349 | 5 | Internal | 56 | 57 |
|  |  | External | 58 | 59 |
| PHM4167 | 6 | Internal | 60 | 61 |
|  |  | External | 62 | 63 |
| PHM14947 | 7 | Internal | 64 | 65 |
|  |  | External | 66 | 67 |
| PHM5266 | 8 | Internal | 68 | 69 |
|  |  | External | 70 | 71 |
| PHM12632 | 9 | Internal | 72 | 73 |
|  |  | External | 74 | 75 |
| PHM201 | 10 | Internal | 76 | 77 |
|  |  | External | 78 | 79 |
| PHM4861 | 11 | Internal | 80 | 81 |
|  |  | External | 82 | 83 |
| PHM5421 | 12 | Internal | 84 | 85 |
|  |  | External | 86 | 87 |

TABLE 1-continued

PHM Marker Sequences

| Marker Locus | Reference sequence (SEQ ID NO:) | | Forward (SEQ ID NO:) | Reverse (SEQ ID NO:) |
|---|---|---|---|---|
| PHM4115 | 13 | Internal | 88 | 89 |
|  |  | External | 90 | 91 |
| PHM12521 | 14 | Internal | 92 | 93 |
|  |  | External | 94 | 95 |
| PHM3468 | 15 | Internal | 96 | 97 |
|  |  | External | 98 | 99 |
| PHM10840 | 16 | Internal | 100 | 101 |
|  |  | External | 102 | 103 |
| PHM12755 | 17 | Internal | 104 | 105 |
|  |  | External | 106 | 107 |
| PHM13879 | 18 | Internal | 108 | 109 |
|  |  | External | 110 | 111 |
| PHM4103 | 19 | Internal | 112 | 113 |
|  |  | External | 114 | 115 |
| PHM5363 | 20 | Internal | 116 | 117 |
|  |  | External | 118 | 119 |
| PHM14751 | 21 | Internal | 120 | 121 |
|  |  | External | 122 | 123 |
| PHM16138 | 22 | Internal | 124 | 125 |
|  |  | External | 126 | 127 |
| PHM7877 | 23 | Internal | 128 | 129 |
|  |  | External | 130 | 131 |
| PHM9518 | 24 | Internal | 132 | 133 |
|  |  | External | 134 | 135 |
| PHM7802 | 25 | Internal | 136 | 137 |
|  |  | External | 138 | 139 |
| PHM2134 | 26 | Internal | 140 | 141 |
|  |  | External | 142 | 143 |
| PHM7808 | 27 | Internal | 144 | 145 |
|  |  | External | 146 | 147 |
| PHM9627 | 28 | Internal | 148 | 149 |
|  |  | External | 150 | 151 |
| PHM13716 | 29 | Internal | 152 | 153 |
|  |  | External | 154 | 155 |
| PHM18731 | 30 | Internal | 156 | 157 |
|  |  | External | 158 | 159 |
| PHM2189 | 31 | Internal | 160 | 161 |
|  |  | External | 162 | 163 |
| PHM7734 | 32 | Internal | 164 | 165 |
|  |  | External | 166 | 167 |
| PHM3323 | 33 | Internal | 168 | 169 |
|  |  | External | 170 | 171 |
| PHM4736 | 34 | Internal | 172 | 173 |
|  |  | External | 174 | 175 |
| PHM6441 | 35 | Internal | 176 | 177 |
|  |  | External | 178 | 179 |
| PHM430 | 36 | Internal | 180 | 181 |
|  |  | External | 182 | 183 |
| PHM12224 | 37 | Internal | 184 | 185 |
|  |  | External | 186 | 187 |
| PHM11904 | 38 | Internal | 188 | 189 |
|  |  | External | 190 | 191 |
| PHM6727 | 39 | Internal | 192 | 193 |
|  |  | External | 194 | 195 |
| PHM4578 | 196 | Internal | 215 | 216 |
|  |  | External | 214 | 217 |
| PHM11186 | 197 | Internal | 219 | 220 |
|  |  | External | 218 | 221 |
| PHM14053 | 198 | Internal | 223 | 224 |
|  |  | External | 222 | 225 |
| PHM16736 | 199 | Internal | 227 | 228 |
|  |  | External | 226 | 229 |
| PHM7844 | 200 | Internal | 231 | 232 |
|  |  | External | 230 | 233 |
| PHM8029 | 201 | Internal | 235 | 236 |
|  |  | External | 234 | 237 |
| PHM2130 | 202 | Internal | 239 | 240 |
|  |  | External | 238 | 241 |
| PHM11754 | 203 | Internal | 243 | 244 |
|  |  | External | 242 | 245 |
| PHM1481 | 204 | Internal | 247 | 248 |
|  |  | External | 246 | 249 |
| PHM15089 | 205 | Internal | 251 | 252 |
|  |  | External | 250 | 253 |
| PHM574 | 206 | Internal | 255 | 256 |
|  |  | External | 254 | 257 |
| PHM6427 | 207 | Internal | 259 | 260 |
|  |  | External | 258 | 261 |
| PHM11125 | 208 | Internal | 263 | 264 |
|  |  | External | 262 | 265 |
| PHM13958 | 209 | Internal | 267 | 268 |
|  |  | External | 266 | 269 |
| PHM10468 | 210 | Internal | 271 | 272 |
|  |  | External | 270 | 273 |
| PHM12706 | 211 | Internal | 275 | 276 |
|  |  | External | 274 | 277 |
| PHM405 | 212 | Internal | 279 | 280 |
|  |  | External | 278 | 281 |
| PHM12025 | 213 | Internal | 283 | 284 |
|  |  | External | 282 | 285 |

SEQ ID NOs:1-285 (See Table 1).
SEQ ID NOs:286-389 (See Table 2).

TABLE 2

Production Markers and Their Sequences

| Marker Name | Forward Primer SEQ ID NO: | Reverse Primer SEQ ID NO: | Sense | Allele 1 | Allele 2 | Dye 1 | Dye 2 | Probe 1 SEQ ID NO: | Probe 2 SEQ ID NO: |
|---|---|---|---|---|---|---|---|---|---|
| PHM18693-9-U | 286 | 287 | Anti-Sense | T | C | Red | Fam | 288 | 289 |
| PHM10786-11-U | 290 | 291 | Sense | T | G | Red | Fam | 292 | 293 |
| PHM10786-5-U | 294 | 295 | Anti-Sense | C | A | Red | Fam | 296 | 297 |
| PHM10786-6-U | 298 | 299 | Anti-Sense | T | C | Red | Fam | 300 | 301 |
| PHM8057-801-U | 302 | 303 | Anti-Sense | T | G | Red | Fam | 304 | 305 |
| PHM4044-11-U | 306 | 307 | Sense | T | A | Red | Fam | 308 | 309 |
| PHM14080-16-V | 310 | 311 | Sense | G | A | Red | Fam | 312 | 313 |
| PHM15089-10-U | 314 | 315 | Sense | G | C | Red | Fam | 316 | 317 |
| PHM9364-6-U | 318 | 319 | Sense | G | A | Red | Fam | 320 | 321 |
| PHM201-16-U | 322 | 323 | Anti-Sense | T | C | Red | Fam | 324 | 325 |

TABLE 2-continued

Production Markers and Their Sequences

| Marker Name | Forward Primer SEQ ID NO: | Reverse Primer SEQ ID NO: | Sense | Allele 1 | Allele 2 | Dye 1 | Dye 2 | Probe 1 SEQ ID NO: | Probe 2 SEQ ID NO: |
|---|---|---|---|---|---|---|---|---|---|
| PHM201-17-U | 326 | 327 | Sense | C | G | Red | Fam | 328 | 329 |
| PHM4861-20-U | 330 | 331 | Sense | T | G | Red | Fam | 332 | 333 |
| PHM4861-21-U | 334 | 335 | Anti-Sense | G | A | Red | Fam | 336 | 337 |
| PHM5421-5-V | 338 | 339 | Sense | G | T | Red | Fam | 340 | 341 |
| PHM4115-35-U | 342 | 343 | Anti-Sense | G | T | Red | Fam | 344 | 345 |
| PHM12521-18-U | 346 | 347 | Sense | T | G | Red | Fam | 348 | 349 |
| PHM12521-19-U | 350 | 351 | Sense | G | A | Red | Fam | 352 | 353 |
| PHM12521-29-U | 354 | 355 | Sense | G | A | Red | Fam | 356 | 357 |
| C00386-397-U | 358 | 359 | Sense | T | C | Red | Fam | 360 | 361 |
| PHM13418-18-U | 362 | 363 | Sense | T | C | Fam | Red | 364 | 365 |
| PHM13418-10-U | 366 | 367 | Sense | C | T | Fam | Red | 368 | 369 |
| PHM113-7-U | 370 | 371 | Anti-Sense | C | T | Fam | Red | 372 | 373 |
| PHM10337-11-U | 374 | 375 | Anti-Sense | T | C | Red | Fam | 376 | 377 |
| PHM16736-8-V | 378 | 379 | Sense | T | A | Red | Fam | 380 | 381 |
| PHM12025-48-U | 382 | 383 | Anti-Sense | T | C | Red | Fam | 384 | 385 |
| PHM11186-16-V | 386 | 387 | Sense | T | C | Red | Fam | 388 | 389 |

DETAILED DESCRIPTION

The present invention provides allelic compositions in maize and methods for identifying and for selecting maize plants with favorable mechanical stalk strength. Also within the scope of this invention are allelic compositions and methods used to identify and to counter-select maize plants that have decreased mechanical stalk strength. The following definitions are provided as an aid to understand this invention.

The term "allele" refers to one of two or more different nucleotide sequences that occur at a specific locus.

The term "altered mechanical stalk strength" refers to an increase or a decrease in the ability of maize plants to resist breakage as a result of having a particular allele at a marker locus or a combination of alleles at multiple marker loci.

An "amplicon" is a DNA fragment generated using the polymerase chain reaction.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" can also be referred to as a "linkage group".

The term "complement" refers to a nucleotide sequence that is complementary to a given nucleotide sequence, i.e. the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

Maize plants with "decreased mechanical stalk strength" are more prone to stalk lodging and have mechanically weaker stalks. The term "decreased" relates to the degree of physical strength and/or the degree of resistance to breakage and is used to describe the effect on mechanical stalk strength when a particular allele is present or absent.

A plant referred to herein as "diploid" has two sets (genomes) of chromosomes.

A plant referred to herein as "doubled haploid" is developed by doubling the haploid set of chromosomes. A doubled haploid plant is considered a homozygous plant.

An "elite line" is any line that has resulted from breeding and selection for superior agronomic performance.

A "favorable allele" is the allele at a particular locus that confers, or contributes to an agronomically desirable phenotype and that allows the identification of plants with that agronomically desirable phenotype e.g., increased mechanical stalk strength. A "favorable allele" of a marker is a marker allele that segregates with the favorable phenotype.

Maize plants with "favorable" mechanical stalk strength characteristics have higher than average mechanical stalk strength and are less prone to stalk lodging. Maize plants with "unfavorable" mechanical stalk strength characteristics have lower than average mechanical stalk strength and are more prone to stalk lodging.

An "unfavorable allele" of a marker is a marker allele that segregates with the unfavorable plant phenotype, therefore providing the benefit of identifying plants that can be removed from a breeding program or planting.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by the recombination frequencies between them, and recombinations between loci can be detected using a variety of markers. A genetic map is a product of the mapping population, types of markers used, and the polymorphic potential of each marker between different populations. The order and genetic distances between loci (e.g. markers) can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maize GDB). However, information can be correlated from one map to another using a general framework of common markers. One of ordinary skill in the art can use the framework of common markers to identify the positions of markers and loci of interest on each individual genetic map. A comparison of marker positions between the internally derived genetic map and the IBM2 neighbors genetic map for the chromosome 5 QTL can be seen in Table 7.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" refers to any of following maps: IBM, IBM2, IBM2 neighbors, IBM2 FPC0507, IBM2 2004 neighbors, IBM2 2005 neighbors, or IBM2 2005 neighbors frame. IBM genetic maps are based on a B73×Mo17 population in which the progeny from the initial cross were randommated for multiple generations prior to constructing recombinant inbred lines for mapping. Newer versions reflect the addition of genetic and BAC mapped loci as well as enhanced map refinement due to the incorporation of information obtained from other genetic maps.

The term "inbred" refers to a line that has been bred for genetic homogeneity.

Maize plants with "increased mechanical stalk strength" are resistant to stalk lodging and have mechanically stronger stalks. The term "increased" relates to the degree of physical strength and/or the degree of resistance to breakage and is used to describe the effect on mechanical stalk strength when a particular allele is present or absent.

The term "indel" refers to an insertion or deletion, wherein one line may be referred to as having an insertion relative to a second line, or the second line may be referred to as having a deletion relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

As used herein, the term "linkage" is used to describe the degree with which one marker locus is associated with another marker locus or some other locus (for example, a mechanical stalk strength locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a phenotype. A marker locus can be "associated with" (linked to) a trait, e.g., mechanical stalk strength. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a gene or marker is located.

The term "lodge" is synonymous with break. Hence, stalks that lodge are those that break at a position along the stalk.

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zea mays* L. ssp. *mays* and is also known as corn.

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus. Marker alleles designated with a number, such as e.g. PHM3468 allele 2, represent the specific combination of alleles, also referred to as a "marker haplotype", at that specific marker locus.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus. Nucleic acids are "complementary" when they specifically "hybridize", or pair, in solution, e.g., according to Watson-Crick base pairing rules.

"Mechanical stalk strength" refers to the physical strength of a maize stalk and its resistance to breakage (also known as "lodging").

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

Each "PHM" marker represents two sets of primers that when used in a nested PCR, amplify a specific piece of DNA. The external set is used in the first round of PCR, after which the internal sequences are used for a second round of PCR on the products of the first round. This increases the specificity of the reaction. A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism preferably has a frequency of at least 1% in a population. A polymorphism can include a single nucleotide polymorphism (SNP), a simple sequence repeat (SSR), or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers were developed for specific polymorphisms identified using PHM markers and the nested PCR analysis. These production SNP markers were specifically designed for use with the Invader Plus® (Third Wave Technologies) platform.

The term "progeny" refers to the offspring generated from a cross.

A "progeny plant" is generated from a cross between two plants.

The term "quantitative trait locus" or "QTL" refers to a region of DNA that is associated with the differential expression of a phenotypic trait in at least one genetic background, e.g., in at least one breeding population. QTLs are closely linked to the gene or genes that underlie the trait in question.

A "reference sequence" is a defined sequence used as a basis for sequence comparison. The reference sequence for a PHM marker is obtained by genotyping a number of lines at the locus, aligning the nucleotide sequences in a sequence alignment program (e.g. Sequencher), and then obtaining the consensus sequence of the alignment. Hence, a reference sequence identifies the polymorphisms in alleles at a locus. A reference sequence may not be a copy of an actual DNA sequence; however, it is useful for designing primers and probes for actual polymorphisms in the locus.

"Stalk lodging" refers to the breakage of the stalk. Stalk lodging typically occurs at or below the ear, but can occur at any position along the stalk.

A "three-point bend test" is an electromechanical system for evaluating mechanical stalk strength. In this test, load can be applied to internodes below the ear using an Instron™ machine, such as Model 4411 (Instron Corporation, 100 Royall Street, Canton, Mass. 02021), or other crushing device. The load needed to break the internode is used as a measure of mechanical strength. The mechanical stalk strength values obtained from the three-point bend test have shown to be highly correlated to lodging scores that have been assigned based on field observations.

A "topcross test" is a test performed on progeny derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Turning now to the embodiments:

Stalk Lodging and Mechanical Stalk Strength

Methods for identifying and for selecting maize plants with favorable or unfavorable mechanical stalk strength characteristics through the genotyping of associated marker loci are provided. Mechanical stalk strength in maize is an agronomically important trait, as increased mechanical stalk strength enhances resistance to stalk lodging.

Stalk lodging, or stalk breakage, can occur at various developmental stages. During vegetative growth, internodes are rapidly elongating, causing cell walls to thin, thereby making stalks more prone to breakage. This type of breakage is called green snap, or brittle snap, and most often occurs between the vegetative stages of V5 and V8 and between the vegetative V12 stage and the reproductive R1 stage. Plants that lodge during the V5 to V8 stage usually do not recover, since breakage typically occurs below the growing point. Between the vegetative V12 stage and the reproductive R1 stage, stalks typically break at nodes just below or above the ear. If the site of breakage is below the ear, ear development is severely impeded, resulting in no grain production. If the site of breakage is above the ear, limited or no grain production may still result, due to the lack of photosynthetic surface area, which is required for supplying the developing ear(s) with nutrients.

Stalk lodging can also occur late season. As a maize plant matures, ear weight increases, as does the load imposed on the stalk. The increased load can cause the maize stalk to break, especially when additional mechanical stresses, either biotic or abiotic, are imposed on the plant. If stalk breakage or lodging does occur, the ear may fall to the ground or to a height where harvest machinery cannot access the ear, thereby reducing yield. Alternatively, the proximity of the fallen ear to the ground increases the probability of fungal spores being splashed on to the ear, resulting in a loss of grain quality.

Maize plants with increased mechanical stalk strength, however, have a greater capacity to bear the weight of the ear and any applied mechanical force. It is therefore desirable to identify and select maize plants with increased mechanical stalk strength to prevent yield and grain quality losses due to stalk lodging. It is also desirable to eliminate maize plants with decreased mechanical stalk strength from maize breeding programs for the same purpose.

QTL Mapping

It has been recognized for quite some time that specific chromosomal loci (or intervals) in an organism's genome that correlate with particular quantitative phenotypes, such as mechanical stalk strength, can be mapped genetically using markers. Such loci are termed quantitative trait loci, or QTL. The plant breeder can advantageously use molecular markers to identify desired individuals by identifying marker alleles that show a statistically significant probability of co-segregation with a desired phenotype, manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a quantitative trait such as mechanical stalk strength. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect QTLs are: 1) Population-based structured association analysis and 2) Pedigree-based association analysis. In a population-based structured association analysis, lines are obtained from pre-existing populations with multiple founders, e.g. elite breeding lines. Population-based association analyses rely on the decay of linkage disequilibrium (LD) and the idea that in an unstructured population, only correlations between QTL and markers closely linked to the QTL will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a QTL at that position on the genetic map (which will fall between two particular marker loci).

The present invention provides QTLs that demonstrate statistically significant co-segregation with mechanical stalk strength, as determined by association analyses. Detection of these loci or additional linked loci can be used in marker assisted maize breeding programs to produce plants with a favorable mechanical stalk strength phenotype or to eliminate plants with an unfavorable mechanical stalk strength phenotype from breeding programs or planting.

Markers Associated with Mechanical Stalk Strength

Markers associated with mechanical stalk strength are identified herein.

For the QTL identified on chromosome 5 (referred to herein as QTL5), the marker locus can be selected from any of the marker loci provided in Table 3 or Table 7, including the PHM markers, PHM201, PHM5421, PHM3468, PHM12521, and PHM10840, and the production SNP markers PHM201-16-U, PHM201-17-U, PHM4861-20-U, PHM4861-21-U, PHM5421-5-V, PHM4115-35-U, PHM12521-18-U, PHM12521-19-U, PHM12521-29-U, and C00386-397-U, as well as any other marker linked to these QTL markers (linked markers can be determined from the MaizeGDB resource; see framework of markers in Table 7).

For the QTL identified on chromosome 9 (referred to herein as QTL9), the marker locus can be selected from any of the marker loci provided in Example 1C, Table 5, or Table 9, including the PHM markers, PHM4578, PHM11186, PHM12025, PHM14053, PHM405, and PHM16736, and the production SNP markers, PHM13418-18, PHM13418-10, PHM113-7, PHM10337-11-U, PHM16736-8-V, PHM12025-48, and PHM11186-16-V, as well as any other marker linked to these QTL markers.

For one of the QTLs identified on chromosome 1 (referred to herein as QTL1A), the marker locus can be selected from any of the marker loci provided in Example 1D, Table 5, or Table 9, including the PHM markers, PHM7844, PHM8029, PHM2130, and PHM574, and the production SNP markers, PHM18693-9-U, PHM10786-11-U, PHM10786-5-U, PHM10786-6-U, and PHM8057-801-U, as well as any other marker linked to these QTL markers.

For one of the QTLs identified on chromosome 1 (referred to herein as QTL1B), the marker locus can be selected from any of the QTL marker loci provided in Example 1D, Table 5, or Table 9, including the PHM markers, PHM11754, PHM1481, PHM6427, and PHM15089, and the production SNP markers, PHM4044-11-U, PHM14080-16-V, PHM15089-10-U, and PHM9364-6-U, as well as any other marker linked to these QTL markers.

For one of the QTLs identified on chromosome 1 (referred to herein as QTL1C), the marker locus can be selected from any of the QTL marker loci provided in Example 1D, Table 5, or Table 9, including the PHM markers, PHM11125, PHM13958, PHM10468, and PHM12706, as well as any other marker linked to these QTL markers.

Physical Map Locations of QTLs

The genetic elements or genes located on a contiguous linear span of genomic DNA on a single chromosome are physically linked.

For the QTL5 region, the two markers with the largest physical distance between them that still remain associated with the phenotype of interest, mechanical stalk strength, are PHM654 (reference sequence=SEQ ID NO:1) and PHM6727 (reference sequence=SEQ ID NO:39). PHM654 is located on BAC c0216105, and PHM6727 is located on BAC c0117h02. Hence, these two BACs delineate the mechanical stalk strength QTL on the maize physical map. Any BAC that assembles to the contiguous DNA between and including BAC c0216105 and BAC c0117h02 can house marker loci that are associated with the mechanical stalk strength trait. FIGS. 1A-I show the physical map arrangement of the sequenced BACs that make up the contiguous stretch of DNA between and including BAC c0216105 and BAC c0117h02. The gaps (represented by dotted lines) are not gaps in the contiguous stretch of DNA per se but are areas where BACs that have not been sequenced assemble to the physical map.

An area on chromosome 9 defined by and including PHM4578 and PHM11186 delineates the QTL9 region. Any polynucleotide that can hybridize to the contiguous DNA between and including SEQ ID NO:196 (the reference sequence for PHM4578), or a nucleotide sequence that is 95% identical to SEQ ID NO:196 based on the Clustal V method of alignment, and SEQ ID NO:197 (the reference sequence for PHM11186), or a nucleotide sequence that is 95% identical to SEQ ID NO:197 based on the Clustal V method of alignment, and that is associated with mechanical stalk strength can be used as a marker for mechanical stalk strength. On the current B73 physical map, PHM4578 is located on BACs c0478c20, c0414c21, and b0505j22, while PHM11186 is located on BACs c0475m02 and b0197d12.

An area on chromosome 1 defined by and including PHM7844 and PHM8029 delineates the QTL1A region. Any polynucleotide that can hybridize to the contiguous DNA between and including SEQ ID NO:200 (the reference sequence for PHM7844), or a nucleotide sequence that is 95% identical to SEQ ID NO:200 based on the Clustal V method of alignment, and SEQ ID NO:201 (the reference sequence for PHM8029), or a nucleotide sequence that is 95% identical to SEQ ID NO:201 based on the Clustal V method of alignment, and that is associated with mechanical stalk strength can be used as a marker for mechanical stalk strength. On the current B73 physical map, PHM7844 is located on BAC b0109 m14, while PHM8029 is located on BAC c0230j20.

An area on chromosome 1 defined by and including PHM11754 and PHM1481 delineates the QTL1B region. Any polynucleotide that can hybridize to the contiguous DNA between and including SEQ ID NO:203 (the reference sequence for PHM11754), or a nucleotide sequence that is 95% identical to SEQ ID NO:203 based on the Clustal V method of alignment, and SEQ ID NO:204 (the reference sequence for PHM1481), or a nucleotide sequence that is 95% identical to SEQ ID NO:204 based on the Clustal V method of alignment, and that is associated with mechanical stalk strength can be used as a marker for mechanical stalk strength. On the current B73 physical map, PHM11754 is not located on a sequenced BAC, while PHM1481 is located on BAC c0347b01.

An area on chromosome 1 defined by and including PHM11125 and PHM13958 delineates the QTL1C region. Any polynucleotide that can hybridize to the contiguous DNA between and including SEQ ID NO:208 (the reference sequence for PHM11125), or a nucleotide sequence that is 95% identical to SEQ ID NO:208 based on the Clustal V method of alignment, and SEQ ID NO:209 (the reference sequence for PHM13958), or a nucleotide sequence that is 95% identical to SEQ ID NO:209 based on the Clustal V method of alignment, and that is associated with mechanical stalk strength can be used as a marker for mechanical stalk strength. On the current B73 physical map, PHM11125 is located on BAC c0042p07, while PHM13958 is located on BAC c0188c22.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a QTL marker, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the mechanical stalk strength phenotype, it is important to note that the marker locus is not necessarily part of the QTL locus responsible for the expression of the mechanical stalk strength phenotype. For example, it is not a requirement that the marker polynucleotide sequence be part of a gene that imparts mechanical stalk strength (for example, be part of the gene open reading frame). The association between a specific marker allele with either a favorable or unfavorable mechanical stalk strength phenotype is due to the original "coupling" linkage phase between the marker allele and the QTL allele in the ancestral maize line from which the QTL allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

For QTL5, markers identified in Table 3 or Table 7, as well as any marker within 50 cM of the markers identified in Table 3 or Table 7, can be used to predict mechanical stalk strength trait in a maize plant. This includes any marker within 50 cM of the PHM markers, PHM201, PHM5421, PHM3468, PHM12521, and PHM10840, and the production SNP markers PHM201-16-U, PHM201-17-U, PHM4861-20-U, PHM4861-21-U, PHM5421-5-V, PHM4115-35-U, PHM12521-18-U, PHM12521-19-U, PHM12521-29-U, and C00386-397-U.

For QTL9, markers identified in Example 1C, Table 5, or Table 9, as well as any marker within 50 cM of the markers identified in Example 1C, Table 5, or Table 9, can be used to predict mechanical stalk strength in a maize plant. This includes any marker within 50 cM of the PHM markers, PHM4578, PHM11186, PHM12025, PHM14053, PHM405, and PHM16736, and of the production SNP markers, PHM13418-18, PHM13418-10, PHM113-7, PHM10337-11-U, PHM16736-8-V, PHM12025-48, and PHM11186-16-V.

For QTL1A, markers identified in Example 1D, Table 5, or Table 9, as well as any marker within 50 cM of the markers identified in Example 1D, Table 5, or Table 9, can be used to predict mechanical stalk strength in a maize plant. This includes any marker within 50 cM of PHM7844, PHM8029, PHM2130, or PHM574, and of the production SNP markers, PHM18693-9-U, PHM10786-11-U, PHM10786-5-U, PHM10786-6-U, and PHM8057-801-U.

For QTL1B, markers identified in Example 1D, Table 5, or Table 9, as well as any marker within 50 cM of the markers identified in Example 1D, Table 5, or Table 9, can be used to predict mechanical stalk strength in a maize plant. This includes any marker within 50 cM of the PHM markers, PHM11754, PHM1481, PHM6427, and PHM15089, and of the production SNP markers, PHM4044-11-U, PHM14080-16-V, PHM15089-10-U, and PHM9364-6-U.

For QTL1C, markers identified in Example 1D, Table 5, or Table 9, as well as any marker within 50 cM of the markers identified in Example 1D, Table 5, or Table 9, can be used to predict mechanical stalk strength in a maize plant. This includes any marker within 50 cM of the PHM markers, PHM11125, PHM13958, PHM10468, and PHM12706.

Chromosomal Intervals

Chromosomal intervals that correlate with mechanical stalk strength are provided. A variety of methods well known in the art are available for identifying chromosomal intervals. The boundaries of such chromosomal intervals are drawn to encompass markers that will be linked to one or more QTL. In other words, the chromosomal interval is drawn such that any marker that lies within that interval (including the terminal markers that define the boundaries of the interval) can be used as a marker for mechanical stalk strength. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

Each of the intervals described shows a clustering of markers that co-segregate with mechanical stalk strength. This clustering of markers occurs in relatively small domains on the linkage groups, indicating the presence of one or more QTL in those chromosome regions. QTL intervals were drawn to encompass the markers that co-segregate with mechanical stalk strength. The intervals are defined by the markers on their termini, where the interval encompasses markers that map within the interval, whether known or unknown, as well as the markers that define the termini.

For QTL5, any marker located within any of the following intervals finds use as a marker for mechanical stalk strength. These intervals include:
   (i) PHM654 and PHM6727;
   (ii) PHM12632 and PHM3323;
   (iii) PHM201 and PHM3323; and
   (iv) PHM201 and PHM3468.

PHM654 and PHM6727 are separated by ~25 cM on the internally-derived genetic map and define a chromosomal interval encompassing a cluster of markers that co-segregate with mechanical stalk strength in the NSS subpopulation at a p-level of ≤0.01 (FIG. 2C). PHM12632 and PHM3323, separated by ~9 cM on the internally-derived genetic map, define a chromosomal interval encompassing a cluster of markers that co-segregate with mechanical stalk strength in the NSS subpopulation at a p-level of ≤0.001 (FIG. 2D). PHM201 and PHM3323, separated by ~9 cM on the internally-derived genetic map, define a chromosomal interval encompassing a cluster of markers that co-segregate with mechanical stalk strength in the NSS subpopulation at a p-level of ≤0.0001 (FIG. 2E).

For QTL9, any marker located within any of the following intervals finds use as a marker for mechanical stalk strength:
   (i) PHM4578 and PHM11186 and
   (ii) PHM14053 and PHM16736.

PHM4578 and PHM11186, separated by ~3.5 cM on the internally-derived genetic map, define a chromosomal interval encompassing a cluster of markers that co-segregate with mechanical stalk strength in the NSS subpopulation at a p-level of ≤0.01. PHM14053 and PHM16736, separated by ~1.5 cM on the internally-derived genetic map, define a chromosomal interval encompassing a cluster of markers that co-segregate with mechanical stalk strength in the NSS subpopulation at a p-level of ≤0.001.

For QTL1A, any marker located within any of the following intervals finds use as a marker for mechanical stalk strength:
   (i) PHM7844 and PHM8029 and
   (ii) PHM7844 and PHM574.

PHM7844 and PHM8029, separated by ~16 cM on the internally-derived genetic map, define a chromosomal interval encompassing a cluster of markers that co-segregate with mechanical stalk strength in the NSS subpopulation at a p-level of ≤0.01. PHM7844 and PHM574, separated by ~6.5 cM on the internally-derived genetic map, define a chromosomal interval encompassing a cluster of markers that co-segregate with mechanical stalk strength in the NSS subpopulation at a p-level of ≤0.001.

For QTL1B, any marker located within any of the following intervals finds use as a marker for mechanical stalk strength:
   (i) PHM11754 and PHM1481 and
   (ii) PHM6427 and PHM1481.

PHM11754 and PHM1481, separated by ~21 cM on the internally-derived genetic map, define a chromosomal interval encompassing a cluster of markers that co-segregate with mechanical stalk strength in the NSS subpopulation at a p-level of ≤0.01. PHM6427 and PHM1481, separated by ~21 cM on the internally-derived genetic map, define a chromosomal interval encompassing a cluster of markers that co-segregate with mechanical stalk strength in the NSS subpopulation at a p-level of ≤0.001.

For QTL1C, any marker located within any of the following intervals finds use as a marker for mechanical stalk strength:
(i) PHM11125 and PHM13958 and
(ii) PHM10468 and PHM13958.

PHM11125 and PHM13958, separated by ~15 cM on the internally-derived genetic map, define a chromosomal interval encompassing a cluster of markers that co-segregate with mechanical stalk strength in the NSS subpopulation at a p-level of ≤0.01. PHM10468 and PHM13958, separated by ~12 cM on the internally-derived genetic map, define a chromosomal interval encompassing a cluster of markers that co-segregate with mechanical stalk strength in the NSS subpopulation at a p-level of ≤0.001.

Chromosomal intervals can also be defined by markers that are in linkage disequilibrium with a known QTL marker, and $r^2$ is a common measure of linkage disequilibrium (LD) in the context of association studies. For example, if the $r^2$ value of LD between a chromosome 5 marker locus lying within the interval of PHM654 and PHM6727 and any of the chromosome 5 QTL markers identified in Table 3 or Table 7 is greater than ⅓ (Ardlie et al., Nature Reviews Genetics 3:299-309 (2002)), the loci are in linkage disequilibrium.

Marker Alleles and Haplotypic Combinations

A marker of the invention can also be a combination of particular alleles at one or more marker loci, otherwise known as a haplotype. The alleles described below could be used in combination to identify and select for maize plants with mechanical stalk characteristics.

Favorable SNP alleles at QTL5 marker loci have been identified herein and include: a "G" at position 314 in SEQ ID NO:12 (PHM5421), a "G" at position 93 in SEQ ID NO:15 (PHM3468), a "T" at position 101 in SEQ ID NO:15 (PHM3468), a "G" at position 245 in SEQ ID NO:15 (PHM3468), a "T" at position 101 in SEQ ID NO:14 (PHM12521), an "A" at position 186 in SEQ ID NO:14 (PHM12521), a "C" at position 37 in SEQ ID NO:16 (PHM10840), an "A" at position 240 in SEQ ID NO:16 (PHM10840), and a "C" at position 315 in SEQ ID NO:16 (PHM10840), a "C" at PHM201-16-U, a "C" or "G" at PHM201-17-U, a "T" or "G" at PHM4861-20-U, an "A" at PHM4861-21-U, a "G" at PHM5421-5-V, a "G" or "T" at PHM4115-35-U, a "T" at PHM12521-18-U, an "A" at PHM12521-19-U, a "G" at PHM12521-29-U, and a "C" at C00386-397-U.

Favorable SNP alleles at QTL9 marker loci have been identified herein and include: a "C" at position 225 in SEQ ID NO:199 (PHM16736), a "T" at position 326 in SEQ ID NO:199 (PHM16736), an "A" at position 422 in SEQ ID NO:199 (PHM16736), a "C" at position 193 in SEQ ID NO:198 (PHM14053), a "C" at position 341 in SEQ ID NO:198 (PHM14053), a "C" at position 386 in SEQ ID NO:198 (PHM14053), a "T" at position 374 in SEQ ID NO:198 (PHM14053), a "C" at position 216 in SEQ ID NO:213 (PHM12025), a "C" at PHM13418-18, a "C" at PHM13418-10, a "T" at PHM113-7, a "T" at PHM10337-11-U, an "A" at PHM16736-8-V, a "C" at PHM12025-48, and a "T" at PHM11186-16-V.

Favorable SNP alleles at QTL1A marker loci have been identified herein and include: a "T" at position 75 of SEQ ID NO:202 (PHM2130), an "A" at position 170 of SEQ ID NO:202 (PHM2130), a "C" at position 179 of SEQ ID NO:202 (PHM2130), a "G" at position 358 of SEQ ID NO:202 (PHM2130), a "T" at PHM18693-9-U, a "G" at PHM10786-11-U, a "C" at PHM10786-5-U, a "T" at PHM10786-6-U, and a "G" at PHM8057-801-U.

Unfavorable SNP alleles at QTL5 marker loci have been identified herein and include: a "C" at position 132 in SEQ ID NO:10 (PHM201) and an "A" at position 230 in SEQ ID NO:10 (PHM201).

Unfavorable SNP alleles at QTL1B marker loci have been identified herein and include: a "G" at position 284 in SEQ ID NO:205 (PHM15089), a "T" at PHM4044-11-U, an "A" at PHM14080-16-V, a "C" at PHM15089-10-U, and a "G" at PHM9364-6-U.

An unfavorable SNP allele at a QTL1C marker locus has been identified herein, a "C" at position 322 of SEQ ID NO:210.

The skilled artisan would expect that there might be additional polymorphic sites at marker loci in and around the QTL markers identified herein, wherein one or more polymorphic sites is in high linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Methods for marker assisted selection (MAS), in which phenotypes are selected based on marker genotypes, are also provided. To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. The procedures used to detect marker alleles are known to one of ordinary skill in the art. After the presence (or absence) of a particular marker allele in the biological sample is verified, the plant is selected and is crossed to a second plant, e.g. a maize plant from an elite line. The progeny plants produced by the cross can be evaluated for that specific marker allele, and only those progeny plants that have the desired marker allele will be chosen.

Maize plant breeders desire combinations of desired genetic loci, such as those marker alleles associated with increased mechanical stalk strength, with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to mechanical stalk strength loci, provide an effective method for selecting varieties with increased mechanical stalk strength in breeding programs. For example, one advantage of marker-assisted selection over field evaluations for mechanical stalk strength is that MAS can be done at any time of year, regardless of the growing season. Moreover, environmental effects are largely irrelevant to marker-assisted selection.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable mechanical stalk strength marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because plants may be otherwise undesirable, e.g., due to low yield, low fecundity, or the like. In contrast, strains which are the result of intensive breeding programs may have excellent yield, fecundity or the like, merely being deficient in one desired trait such as mechanical stalk strength.

One application of MAS is to use the markers to increase the efficiency of an introgression or backcrossing effort aimed at introducing an increased mechanical stalk strength QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

In general, MAS uses polymorphic markers that have been identified as having a significant likelihood of co-segregation with the mechanical stalk strength trait. Such markers are presumed to map near a gene or genes that give the plant its mechanical stalk strength phenotype, and are considered indicators for the desired trait, and hence, are termed QTL markers. Plants are tested for the presence of a desired allele in the QTL marker, and plants containing a desired genotype at one or more loci are expected to transfer the desired genotype, along with a desired phenotype, to their progeny.

The markers and QTL intervals presented herein find use in MAS to select maize plants or germplasm for mechanical stalk strength characteristics. Methods for selection involve obtaining DNA accessible for analysis, detecting the presence or absence of either an identified marker allele or an unknown marker allele that is linked to and associated with an identified marker allele, and then selecting the maize plant or germplasm based on the allele detected.

Marker alleles that can be detected include: a "G" at PHM3468.1, a "T" at PHM3468.4, a "G" at PHM3468.18, a "T" at PHM12521.12, a "C" at PHM10840.105, an "A" at PHM10840.118, a "C" at PHM10840.130, a "C" at PHM16736.6, an "A" at PHM16736.14, a "C" at PHM14053.7, a "C" at PHM14053.8, a "C" at PHM14053.14, a "T" at PHM405.35, a "C" at PHM12025.26, a "T" at PHM18693-9-U, a "G" at PHM10786-11-U, a "C" at PHM10786-5-U, a "T" at PHM10786-6-U, a "G" at PHM8057-801-U, a "C" at PHM201-16-U, a "C" at PHM201-17-U, a "G" at PHM201-17-U, a "T" at PHM4861-20-U, a "G" at PHM4861-20-U, an "A" at PHM4861-21-U, a "G" at PHM5421-5-V, a "G" at PHM4115-35-U, a "T" at PHM4115-35-U, a "T" at PHM12521-18-U, an "A" at PHM12521-19-U, a "G" at PHM12521-29-U, a "C" at C00386-397-U, a "C" at PHM13418-18, a "C" at PHM13418-10, a "T" at PHM113-7, a "T" at PHM10337-11-U, an "A" at PHM16736-8-V, a "C" at PHM12025-48, a "T" at PHM11186-16-V, and any marker allele associated with and linked to any of the marker alleles listed above by 30, 25, 20, 15, 10, 9, 8, 7, 6, 5, 4, 3, 2, 1, 0.9, 0.8, 0.7, 0.6, 0.5, 0.4, 0.3, 0.2, or 0.1 cM. The maize plant or germplasm that has any of these marker alleles can be selected.

Marker alleles that can be detected can also include: a "T" at PHM2130.24, an "A" at PHM2130.29, a "C" at PHM2130.30, a "G" at PHM2130.33, a "G" at PHM15089.13, a "C" at PHM12706.14, a "C" at PHM201.10, an "A" at PHM201.18, a "T" at PHM4044-11-U, an "A" at PHM14080-16-V, a "C" at PHM15089-10-U, a "G" at PHM9364-6-U, and any marker allele associated with and linked to any of the marker alleles listed above by 30, 25, 20, 15, 10, 9, 8, 7, 6, 5, 4, 3, 2, 1, 0.9, 0.8, 0.7, 0.6, 0.5, 0.4, 0.3, 0.2, or 0.1. The maize plant or germplasm that does not have any of these marker alleles can be selected.

Methods for selecting maize plants with mechanical stalk strength characteristics can also involve detecting alleles at one or more marker loci lying within specific chromosomal intervals or assaying at least one marker locus within a specific interval in which the marker locus is associated with mechanical stalk strength.

For instance, a maize plant having at least one allele of a marker locus lying within any of the following QTL5 intervals:

(i) PHM654 and PHM6727;
(ii) PHM12632 and PHM3323;
(iii) PHM201 and PHM3323; and
(iv) PHM201 and PHM3468, wherein the allele is associated with increased mechanical stalk strength, can be crossed to another maize plant, and a progeny plant arising from the cross can be evaluated for the marker allele that is associated with increased mechanical stalk strength and then selected if it possesses the marker allele.

Methods can also include assaying at least one marker locus in the maize plant. The marker can lie within any of the following chromosomal intervals comprising and flanked by:

(1) PHM7844 and PHM8029;
(2) PHM7844 and PHM574;
(3) PHM11754 and PHM1481;
(4) PHM6427 and PHM1481;
(5) PHM11125 and PHM13958;
(6) PHM10468 and PHM13958;
(7) PHM4578 and PHM11186; or
(8) PHM14053 and PHM16736; and the marker locus is associated with mechanical stalk strength. Either a maize plant that possesses a favorable allele or a maize plant that does not possess an unfavorable allele could then be selected.

Phenotypic Assessment of Mechanical Stalk Strength

Any method known in the art can be used to evaluate mechanical stalk strength. Some methods involve the measurement of stalk diameter or dry weight per plant, while others can utilize an Instron™ machine or other similar crushing device to assess the load needed to break a stalk. The three point bend test is often used in conjunction with an Instron™ machine or other similar crushing device, and mechanical stalk strength values obtained from the three-point bend test have shown to be highly correlated to lodging scores assigned based on field observations. Still another method can involve the use of a stalk-penetrating device.

In addition, any method that uses a device to accurately reproduce wind forces, in order to select plants with increased mechanical stalk strength in the field, can be utilized for the characterization of mechanical stalk strength in maize plants and for the identification of favorable and/or undesirable quantitative trait loci (QTLs) associated with mechanical stalk strength. A device and method used to screen for selected wind-resistance traits in maize, including stalk strength, are described in patent application US2007/0125155 (published Jun. 6, 2007). When this device and method are used, the unit of measure is the number or percentage of plants that have lodged, or broken, stalks (or, alternatively, the number or percentage of plants that do not lodge).

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1A

QTL Detection: Association Mapping Analysis

An association mapping strategy was undertaken to identify markers associated with mechanical stalk strength in maize. In this association analysis, a collection of 599 maize lines was analyzed by DNA sequencing at 4000-10000 genes (genetic loci). The lines encompassed elite germplasm, commercially released cultivars, and other public varieties.

Phenotypic scores were obtained from 189 individuals in the collection. Mechanical stalk strength was measured using an Instron™ machine, Model 4411 (Instron Corporation, 100 Royall Street, Canton, Mass. 02021), and a three point bend test, with the force applied between nodes 3 and 4 below the ear. The score was the load applied to break the internode, or the weight in kg applied to the internode at the yielding, or breaking, point. Data collection was typically done in one scoring after flowering time (at end of season), and an average score for each line was assigned based on data accumulated over multiple locations. Mechanical stalk strength values for the 189 lines varied from 4.208 to 19.569 kg at yield point. Plants with high scores have greater relative mechanical stalk strength.

The phenotypic scores and marker information for each of the 189 lines was input into the association analysis. A structure-based association analysis was conducted using standard association mapping methods, where the population structure is controlled using marker data. The model-based cluster analysis software, Structure, developed by Pritchard et al., (Genetics 155:945-959 (2000)) was used with haplotype data for 880 elite maize inbreds at two hundred markers to estimate admixture coefficients and assign the inbreds to seven subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

Figure 3:
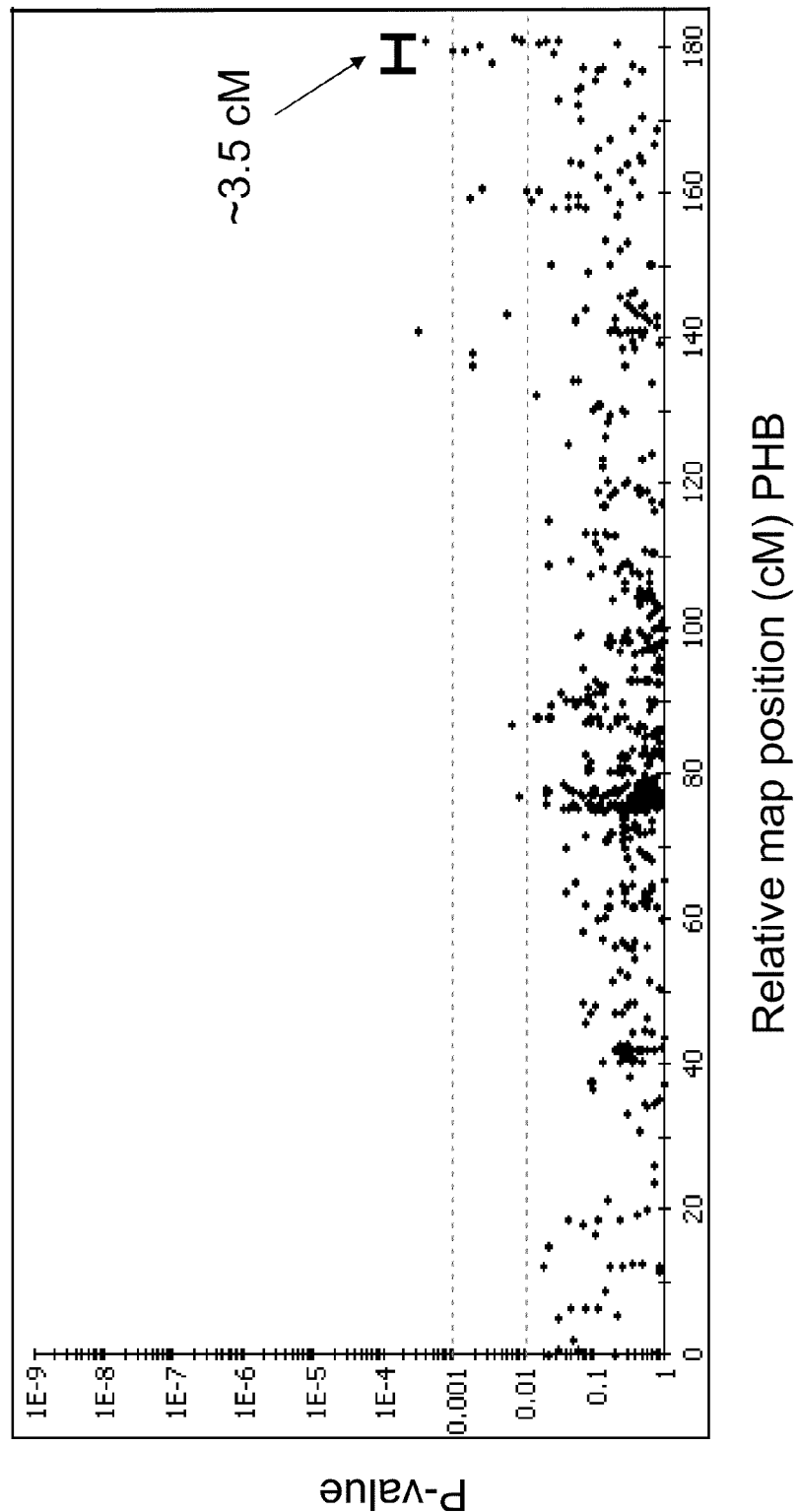
Figure 4:
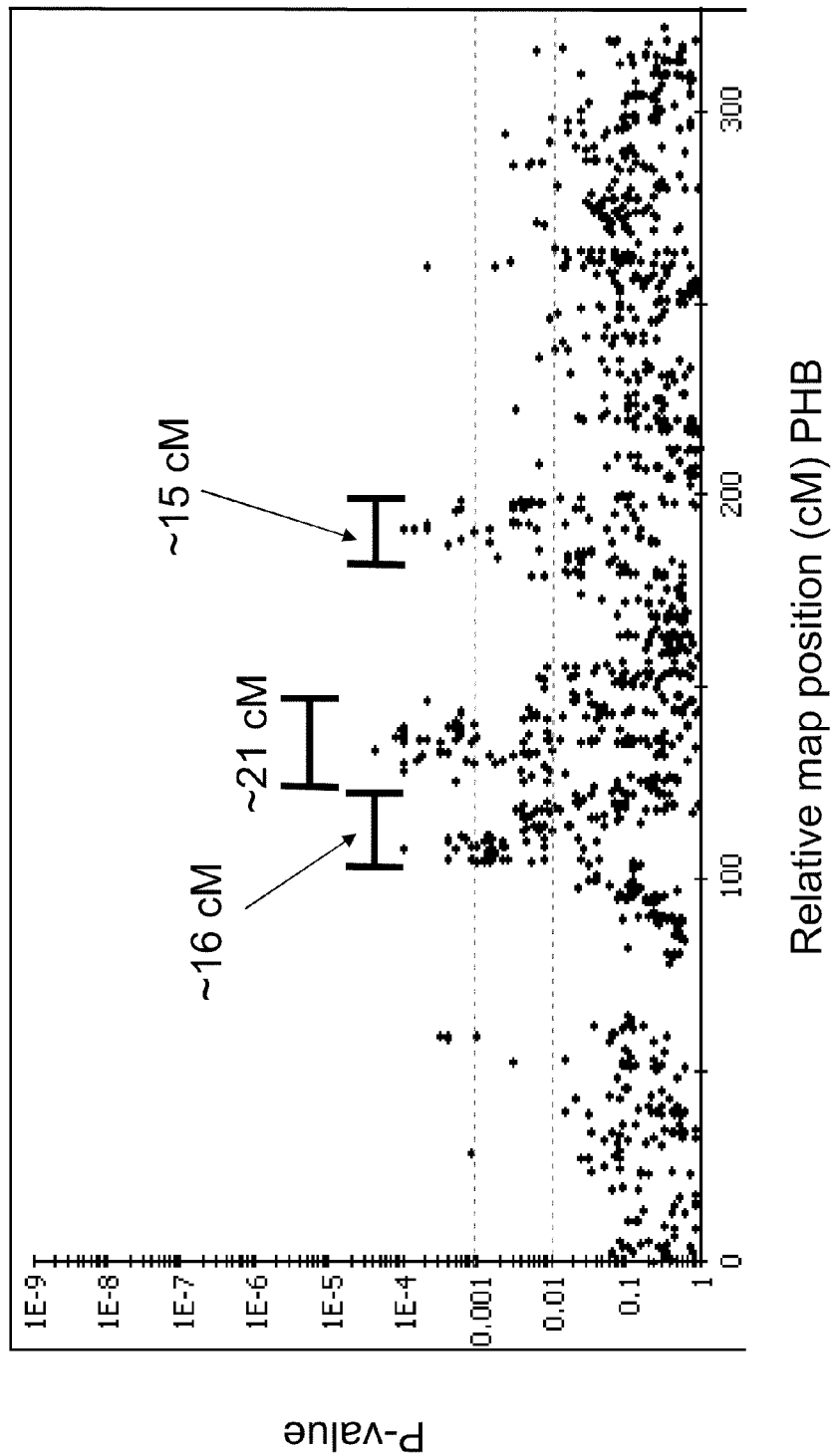

QTLs of interest were identified based on the results of the association analyses. These QTLs are described in examples 1B-D and are shown in FIGS. 2-4. In FIGS. 2-4, positions are given in cM, with position zero being the first (most distal from the centromere) marker known at the beginning of the chromosome. These map positions are not absolute and represent an estimate of map position based on the internally derived genetic map (PHB).

Example 1B

Identification of QTL5

A peak of significant marker-trait associations was identified on chromosome 5 (FIG. 2A). Further analysis at this peak revealed its occurrence in one of the seven subpopulations (FIG. 2B), a non-stiff stalk (NSS) group. Table 3 provides a listing of the chromosome 5 markers significantly associated with the mechanical stalk strength phenotype at the $p \leq 0.01$ level in this NSS subpopulation, representing an interval of ~25 cM on the internally derived genetic map. This chromosomal interval is delineated by and includes markers PHM654 at position 64.21 (p=0.007) and PHM6727 at position 89.62 (p=0.0031) (FIG. 2C). Multiple markers on chromosome 5 are significantly associated with mechanical stalk strength at the $p \leq 0.001$ level, identifying an interval delineated by and including markers PHM12632 at position 71.5 (p=0.0003) and PHM3323 at position 80.89 (p=0.001) (FIG. 2D); these markers are noted with an asterisk in Table 3. In addition, multiple markers on chromosome 5 are significantly associated with mechanical stalk strength at the $p \leq 0.0001$ level, identifying an interval delineated by and including markers PHM201 at position 71.5 (p=0.0003) and PHM3323 at position 80.89 (p=0.001) (FIG. 2E). The most associated markers are PHM201 at position 71.57 (p=0.00001), PHM5421 at position 72.15 (p=0.0000052), and PHM3468 at position 76.53 (p=0.000064).

TABLE 3

Chromosome 5 markers significantly associated with mechanical stalk strength at $p \leq 0.01$ in the NSS subpopulation

| Marker Locus | Relative PHB map position (cM) | P-Value |
| --- | --- | --- |
| PHM654 | 64.21 | 0.007 |
| PHM111 | 65.11 | 0.003 |
| PHM10100 | 66.69 | 0.0023 |
| PHM7357 | 67.42 | 0.0056 |
| PHM5349 | 67.59 | 0.0018 |
| PHM4167 | 69.19 | 0.0023 |
| PHM14947 | 70.29 | 0.0018 |
| *PHM12632 | 71.5 | 3.00E-04 |
| *PHM201 | 71.57 | 1.00E-05 |
| *PHM4861 | 71.57 | 1.00E-04 |
| *PHM5421 | 72.15 | 5.20E-06 |
| *PHM4115 | 73.37 | 5.00E-04 |
| *PHM12521 | 74.86 | 1.00E-04 |
| *PHM3468 | 76.53 | 6.40E-05 |
| *PHM10840 | 76.53 | 1.00E-04 |
| *PHM12755 | 76.82 | 2.00E-04 |
| PHM13879 | 77.01 | 0.0016 |
| PHM4103 | 77.29 | 0.0079 |
| *PHM5363 | 77.66 | 9.00E-04 |
| PHM14751 | 77.84 | 0.0039 |
| PHM16138 | 78.02 | 0.0012 |
| PHM7877 | 78.86 | 0.0029 |
| PHM9518 | 78.89 | 0.005 |
| PHM7802 | 79.48 | 0.0047 |
| *PHM2134 | 79.53 | 3.00E-04 |
| *PHM7808 | 79.6 | 4.00E-04 |
| *PHM9627 | 79.6 | 0.001 |
| PHM13716 | 79.6 | 0.0073 |
| PHM18731 | 79.72 | 0.0019 |
| PHM2189 | 80.36 | 0.0018 |
| *PHM7734 | 80.78 | 1.20E-04 |
| *PHM3323 | 80.89 | 1.00E-04 |
| PHM12224 | 89.17 | 0.0026 |
| PHM11904 | 89.45 | 0.0096 |
| PHM6727 | 89.62 | 0.0031 |

*Markers associated with mechanical stalk strength at $p \leq 0.001$

There were 60 lines assigned by the model-based cluster analysis software, Structure, to the NSS subpopulation in which the QTL for mechanical stalk strength were detected. The lines can be sorted by phenotype and can be assessed at the following marker loci: PHM201, PHM5421, and PHM3468. The phenotype and marker allele data for all 60 lines at the following marker loci: PHM201, PHM5421, and PHM3468, are shown in Table 4. (For the PHM marker alleles, see FIG. 5.)

TABLE 4

Phenotype and marker allele data (PHM201, PHM5421, and PHM3468) for lines in NSS subpopulation

| Line | Phenotype | PHM201 | PHM5421 | PHM3468 |
|---|---|---|---|---|
| PH07H | 19.569 | 2 | 2 | 8 |
| PH14E | 15.29 | 2 | 2 | 8 |
| PH891 | 14.863 | 2 | 2 | 8 |
| PHRF5 | 14.854 | 1 | 3 | 2 |
| PH1AA | 13.738 | 1 | 3 | 2 |
| PH2V7 | 13.667 | 2 | 2 | 8 |
| PHAP9 | 13.536 | 2 | 2 | 8 |
| PH2FT | 13.355 | 2 | 2 | 8 |
| PH1GC | 12.48 | 4 | 2 | 8 |
| PH589 | 12.432 | 1 | 3 | 2 |
| PHDG1 | 12.421 | 4 | 2 | 8 |
| PHG44 | 12.335 | 2 | 2 | NA |
| PH2T6 | 11.993 | 2 | 2 | 8 |
| PH1TB | 11.983 | 2 | 2 | 8 |
| PH806 | 11.783 | 2 | 2 | 8 |
| PHW89 | 11.683 | 2 | 2 | 8 |
| PHM10 | 11.629 | 1 | 3 | 2 |
| PHK42 | 11.492 | 1 | 3 | 2 |
| PH7JD | 11.311 | 2 | 2 | 8 |
| PH8CW | 11.22 | 1 | 3 | 2 |
| PH81B | 11.164 | 1 | NA | 2 |
| PH8KF | 10.871 | 2 | 2 | NA |
| PHJ90 | 10.869 | 5 | 2 | 8 |
| PH1CP | 10.799 | 2 | NA | 8 |
| PH8KG | 10.531 | 2 | 2 | 8 |
| PHR31 | 10.447 | 1 | 3 | 2 |
| PH3KP | 10.206 | 5 | 2 | 8 |
| PH1B5 | 10.148 | 2 | 2 | 8 |
| PH0HR | 10.142 | 2 | NA | 8 |
| PHNG2 | 10.069 | 2 | 2 | 8 |
| PHRF1 | 9.956 | 2 | 2 | 6 |
| PHH93 | 9.919 | 1 | 3 | 2 |
| PH7C8 | 9.88 | 1 | 3 | 2 |
| PH24E | 9.675 | 1 | 3 | 2 |
| PH7DD | 9.632 | 1 | 3 | 2 |
| PH5HP | 9.474 | 1 | 3 | 2 |
| PH7CP | 9.345 | 1 | 3 | 2 |
| PHTE7 | 9.297 | 1 | 3 | 2 |
| PH1N8 | 9.286 | 1 | 3 | 8 |
| PHDP0 | 9.204 | 1 | 3 | 2 |
| PH1W0 | 8.985 | 1 | 3 | 2 |
| PHPP8 | 8.895 | 1 | 3 | 2 |
| PH16M | 8.855 | 1 | 3 | 2 |
| PHK74 | 8.597 | 1 | 3 | 2 |
| PH1G5S | 8.468 | 1 | 3 | 2 |
| PHG29 | 8.432 | 1 | 3 | 2 |
| PHP55 | 8.317 | 1 | 3 | 2 |
| PHN82 | 8.224 | 1 | NA | 2 |
| PH0N7 | 8.182 | 1 | 3 | 2 |
| PH3MW | 8.167 | 1 | 3 | 6 |
| PH05N | 8.156 | 1 | 3 | 2 |
| PH1G5R | 8.014 | 2 | 2 | 8 |
| PH23D | 7.913 | 1 | 3 | 2 |
| PH51K | 7.629 | 1 | 3 | 2 |
| PH7CM | 7.596 | 1 | 3 | 6 |
| PH1B8 | 7.503 | 1 | 3 | 6 |
| PHG50 | 7.435 | 4 | NA | 8 |
| PHKW3 | 7.143 | 1 | 3 | 6 |
| PHACJ | 6.764 | 1 | 3 | 6 |
| PH3N0 | 6.629 | 1 | 3 | 6 |

Further analyses can be performed using marker data from PHM201 and PHM5421. Five lines have missing marker data, and four lines had a haplotype that did not occur with a frequency of at least 10%. Thus, thirty three lines had the haplotype consisting of allele 1 at PHM201 and allele 3 at PHM5421 (designated as "1-3"). The average phenotypic score for the thirty three lines with haplotype 1-3 was 9.326 kg at yield point with a standard error of 0.107. The remaining eighteen lines had the haplotype consisting of allele 2 at PHM201 and allele 2 at PHM5421 (designated as "2-2"). The average phenotypic score for the eighteen lines with haplotype 2-2 was 12.275 kg at yield point with a standard error of 0.370. A depiction of these results can be seen in FIG. 6A.

The allelic variation at PHM3468 can also be an indicator of phenotype. Of the 60 lines, two had missing marker data. Seven lines had marker allele 6 at PHM3468 and an average phenotypic score of 7.680 kg at yield point with a standard error of 0.183. Twenty eight lines had marker allele 2 at PHM3468 and an average phenotypic score of 9.788 kg at yield point with a standard error of 0.113. The remaining twenty three lines had marker allele 8 at PHM3468 and an average phenotypic score of 11.801 kg at yield point with a standard error of 0.289. A depiction of these results can be seen in FIG. 6B.

Thus, allele 1 at PHM201, allele 3 at PHM5421, allele 6 at PHM3468, and the haplotype consisting of allele 1 at PHM201, allele 3 at PHM5421, and allele 6 at PHM3468 are associated with decreased mechanical stalk strength, while allele 2 at PHM201, allele 2 at PHM5421, allele 8 at PHM3468, and the haplotype consisting of allele 2 at PHM201, allele 2 at PHM5421, and allele 8 at PHM3468 are associated with increased mechanical stalk strength.

Example 1C

Identification of QTL9

A peak of significant marker-trait associations was identified on chromosome 9 (FIG. 3) in the same non-stiff stalk (NSS) group in which the chromosome 5 QTL was identified. Chromosome 9 markers associated with mechanical stalk strength at p≤0.01 lie within a ~3.5 cM chromosomal interval delineated by and including markers PHM4578 at position 178.04 (p=0.0034) and PHM11186 at position 181.5 (p=0.0074), while markers associated with mechanical stalk strength at p≤0.001 lie within a ~1.5 cM chromosomal interval delineated by and including markers PHM14053 at position 179.85 (p=0.001) and PHM16736 at position 181.19 (p=4.00E-04). The top associated markers also include: PHM12025 at position 179.78 (p=0.0015) and PHM405 at position 180.29 (p=0.0024).

Example 1D

Identification of QTL1A, QTL1B, and QTL1C

Three peaks of significant marker-trait associations were identified on chromosome 1 (FIG. 4) in the same non-stiff stalk (NSS) group in which the chromosome 5 and 9 QTLs were identified.

In the first chromosome 1 interval, denoted as QTL1A, markers associated with mechanical stalk strength at p≤0.01 lie within a ~16 cM chromosomal interval delineated by and including markers PHM7844 at position 104.55 (p=0.001) and PHM8029 at position 120.44 (p=0.0087), while markers associated with mechanical stalk strength at p≤0.001 lie within a ~6.5 cM chromosomal interval delineated by and including markers PHM7844 at position 104.55 (p=0.001) and PHM574 at position 111.02 (p=6.00E-04). The marker most significantly associated with mechanical stalk strength is PHM2130 at position 107.69 (p=1.00E-04).

In the second chromosome 1 interval, denoted as QTL1B, markers associated with mechanical stalk strength at p≤0.01 lie within a ~21 cM chromosomal interval delineated by and including markers PHM11754 at position 125.26 (p=0.0089) and PHM1481 at position 146.41 (p=2.00E-04), while markers associated with mechanical stalk strength at p≤0.001 lie within a ~21 cM chromosomal interval delineated by and including markers PHM6427 at position 125.63 (p=5.00E-04) and PHM1481 at position 146.41 (p=2.00E-04). The marker most significantly associated with mechanical stalk strength is PHM15089 at position 133.73 (p=4.00E-05).

In the third chromosome 1 interval, denoted as QTL1C, markers associated with mechanical stalk strength at p≤0.01 lie within a ~15 cM chromosomal interval delineated by and including markers PHM11125 at position 184.03 (p=0.0019) and PHM13958 at position 198.8 (p=6.00E-04), while markers associated with mechanical stalk strength at p≤0.001 lie within a ~12 cM chromosomal interval delineated by and including markers PHM10468 at position 187.27 (p=4.00E-04) and PHM13958 at position 198.8 (p=6.00E-04). One marker significantly associated with mechanical stalk strength is PHM12706 at position 191.11 (p=1.40E-04).

Example 1E

Identification of Favorable and Unfavorable Marker Alleles

There were 60 lines assigned by the model-based cluster analysis software, Structure, to the NSS subpopulation in which the QTL for mechanical stalk strength were detected. The lines were sorted by phenotype and assessed at the following marker loci: PHM2130, PHM15089, PHM12706, PHM5421, PHM201, PHM12521, PHM10840, PHM3468, PHM16736, PHM14053, PHM405, and PHM12025. Table 5 shows the individual polymorphisms associated with increased mechanical stalk strength ("favorable"; select for) or decreased mechanical stalk strength ("unfavorable"; select against).

TABLE 5

| Identifier | SNP | Position | In reference sequence |
|---|---|---|---|
| Chromosome 1 - QTL1A | | | |
| PHM2130.24 | T | 75 | SEQ ID NO: 202 |
| PHM2130.29 | A | 170 | SEQ ID NO: 202 |
| PHM2130.30 | C | 179 | SEQ ID NO: 202 |
| PHM2130.33 | G | 358 | SEQ ID NO: 202 |
| Chromosome 1 - QTL1B | | | |
| PHM15089.13 | G | 284 | SEQ ID NO: 205 |
| Chromosome 1 - QTL1C | | | |
| PHM12706.14 | C | 322 | SEQ ID NO: 210 |
| Chromosome 5 | | | |
| PHM5421.5 | G | 314 | SEQ ID NO: 12 |
| PHM3468.1 | G | 93 | SEQ ID NO: 15 |
| PHM3468.4 | T | 101 | SEQ ID NO: 15 |
| PHM3468.18 | G | 245 | SEQ ID NO: 15 |
| PHM12521.12 | T | 101 | SEQ ID NO: 14 |
| PHM12521.19 | A | 186 | SEQ ID NO: 14 |
| PHM10840.105 | C | 37 | SEQ ID NO: 16 |
| PHM10840.118 | A | 240 | SEQ ID NO: 16 |
| PHM10840.130 | C | 315 | SEQ ID NO: 16 |
| PHM201.10 | C | 132 | SEQ ID NO: 10 |
| PHM201.18 | A | 230 | SEQ ID NO: 10 |
| Chromosome 9 | | | |
| PHM16736.6 | C | 225 | SEQ ID NO: 199 |
| PHM16736.8 | T | 326 | SEQ ID NO: 199 |

TABLE 5-continued

| Identifier | SNP | Position | In reference sequence |
|---|---|---|---|
| PHM16736.14 | A | 422 | SEQ ID NO: 199 |
| PHM14053.7 | C | 193 | SEQ ID NO: 198 |
| PHM14053.8 | C | 341 | SEQ ID NO: 198 |
| PHM14053.14 | C | 386 | SEQ ID NO: 198 |
| PHM405.35 | T | 374 | SEQ ID NO: 212 |
| PHM12025.26 | C | 216 | SEQ ID NO: 213 |

Example 2

QTL5 Detection: Composite Interval Mapping

A composite interval mapping approach that combines interval mapping with linear regression was undertaken to identify maize chromosomal intervals and markers associated with mechanical stalk strength. In an interval mapping approach (Lander and Botstein, *Genetics* 121:185-199 (1989)), each of many positions along the genetic map (say at 1 cM intervals) is tested for the likelihood that a QTL is located at that position. The genotype/phenotype data are used to calculate for each test position a LOD score (log of likelihood ratio). When the LOD score exceeds a threshold value (herein the threshold value is 2.5), there is significant evidence for the location of a QTL at that position on the genetic map (which will fall between two particular marker loci).

A high resolution genetic mapping population, the intermated B73×Mo17 (IBM) population, was created by Lee, M et al., Plant Mol Biol 48:453-461 (2002), and is a widely used resource for maize mapping. The B73 inbred represents the Iowa Stiff Stalk Synthetic (BSSS) heterotic group, whereas Mo17 represents a non-BSSS heterotic group. The population was developed by intermating the $F_2$ for four generations and then deriving recombinant inbred lines.

Recombinant inbred lines from the IBM syn4 population were obtained for this study, and two sets of data were collected for each of the 272 individuals obtained. The first set of data was collected using a portable Instron™ machine, near flowering. One growing season with two field replications was used. Measurements were taken at nodes 3 and 4 below the ear and then averaged over replications. The second set of data was obtained using the device and method described in patent application US2007/0125155 (published Jun. 6, 2007). Data were collected near flowering, and the unit of measure was the number of plants that exhibited snapping at a node. Both sets of data were representative of mechanical stalk strength at the vegetative stage, or resistance to brittle snap.

The 272 individuals of the IBM Syn4 generation were genotyped using 324 markers, and the mean scores (averaged across replications; 2 replicates for the Instron™ data, 3 replicates for phenotypic analysis using artificial wind stimulus) were input into Windows QTL Cartographer. Windows QTL Cartographer (the most up-to-date version of this software was used at the date of QTL mapping) was used to perform the composite interval mapping. LOD scores (logarithm of the odds ratio) were estimated across the genome according to standard QTL mapping procedures.

For both sets of data, the composite interval mapping analysis showed one major significant QTL on chromosome 5 (FIG. 7 and FIG. 8), as defined by a significance LOD score threshold of 2.5. The linkage map used for composite interval mapping was a modified IBM2 map for which the genetic distances correspond to a single meiosis recombination fraction (this map was generated internally). The modified IBM2 map comprised the following PHM marker loci located within the chromosome 5 region of interest (with genetic map positions in parentheses): PHM5266 (70.56 cM), PHM4115 (73.37 cM), PHM12521 (74.86 cM), PHM10840 (76.53 cM), PHM4103 (77.29 cM), PHM9518 (78.89 cM), PHM4736 (81.94 cM), PHM6441 (82.51 cM), and PHM430 (86.77 cM). For data set 1 (portable Instron™ data; near flowering; referred to herein as CIM1 for "composite interval mapping data set 1"), the location of the QTL encompassed markers PHM12521, PHM10840, PHM4103, and PHM9518. For data set 2 (wind machine; near flowering; referred to herein as CIM2 for "composite interval mapping data set 2"), the location of the QTL encompassed markers PHM5266, PHM4115, PHM12521, PHM10840, PHM4103, PHM9518, PHM4736, PHM6441, and PHM430.

Example 3

Summary of QTL5 Studies

The results of the chromosome 5 analyses are summarized in Table 6 (the map position of each of the PHM markers on the internally derived genetic map is provided as a reference). All three studies identify the location of a QTL for mechanical stalk strength in the same region of chromosome 5.

TABLE 6

Summary of QTL5 Studies

| Marker Locus | Relative PHB map position (cM) | Association | CIM1 | CIM2 |
|---|---|---|---|---|
| PHM5266 | 70.56 | | | X |
| PHM4115 | 73.37 | ** | | X |
| PHM12521 | 74.86 | ** | X | X |
| PHM10840 | 76.53 | ** | X | X |
| PHM4103 | 77.29 | * | X | X |
| PHM9518 | 78.89 | * | X | X |
| PHM4736 | 81.94 | | | X |
| PHM6441 | 82.51 | | | X |
| PHM430 | 86.77 | | | X |

** = p < 0.001;
* = p < 0.01

A set of common markers can be used to establish a framework for identifying markers in the QTL interval (Table 7). In this table, the markers shaded in gray are public markers, while the unshaded markers are provided herein. All of the markers listed in this table are in a consistent position relative to one another on the PHB internally derived map, the IBM2 neighbors genetic map, and the current physical map (FIGS. 1A-I). In FIGS. 1A-I, PHM12521 and PHM3468 are not shown because the markers are currently on an "unknown" contig that is not assembled to the larger chromosome 5 contig.

TABLE 7

Molecular marker positions on the PHB map and the IBM2 Neighbors map

| Marker Locus | PHB map position (cM) | IBM2 neighbors |
|---|---|---|
| PHM654 | 64.2 | na |
| umc2115 | 64.4 | na |
| PHM111 | 65.1 | na |
| bnlg1879 | 67.3 | 189.80 |
| PHM4167 | 69.2 | na |
| PHM14947 | 70.3 | na |
| PHM5266 | 70.6 | 196.9 |
| PHM201 | 71.6 | na |
| PHM5421 | 72.2 | na |
| mbd109 | na | 203.2 |
| PHM4115 | 73.4 | na |
| PHM12521 | 74.9 | 210.3 |
| PHM3468 | 76.5 | na |
| PHM10840 | 76.5 | 210.3 |
| PHM13879 | 77.0 | na |
| bnlg1046 | 77.1 | 216.3 |
| PHM4103 | 77.3 | 216.3 |
| PHM14751 | 77.8 | na |
| PHM16138 | 78.0 | na |
| umc1597 | 78.3 | na |
| PHM7877 | 78.9 | na |
| PHM9518 | 78.9 | 219.2 |
| PHM7802 | 79.5 | 222.5 |
| PHM9627 | 79.6 | na |
| PHM13716 | 79.6 | na |
| PHM7808 | 79.6 | na |
| umc2035 | 80.7 | 231 |
| PHM7734 | 80.8 | na |
| PHM3323 | 80.9 | na |
| PHM4736 | 81.94 | 240.8 |
| PHM6441 | 82.51 | 240.8 |
| umc2294 | 85.3 | 245.5 |
| PHM430 | 86.77 | 257.8 |
| PHM12224 | 89.17 | na |
| PHM11904 | 89.45 | na |
| PHM6727 | 89.62 | na |

Markers shaded in gray are public markers.

Example 4

QTL Validation

Biparental crosses are typically created to validate QTLs. For example, near isogenic lines containing the individual QTL or combinations of QTL can be generated from a biparental cross of two lines (each with a distinct genotype at a QTL of interest), and the resulting plants can be evaluated for mechanical stalk strength. Phenotypes can be measured using an Instron™ machine to perform the three-point bend test during late season, a portable Instron™ to perform the three-point bend test at or near flowering, the device and method described in patent application US2007/0125155 (published Jun. 6, 2007), or any other method in the art that can be used to evaluate mechanical stalk strength. The lines are then sorted based on their phenotypic values.

Production markers can be developed in the QTL region. These markers will distinguish the parents from one another, preferably using a high throughput assay, and are used to genotype the segregating progeny plants. Production markers could be developed, for example, from individual SNPs that distinguished lines with increased mechanical stalk strength from lines with decreased mechanical stalk strength in the association study described in Examples 1A-E. For instance, PHM5421-5-V, PHM12521-19-U, and PHM16736-8-V were developed from SNPs PHM5421.5, PHM12521.19, and PHM16736.8, respectively.

The PHM markers could also be used to genotype the progeny via the sequencing of PCR products. The primers for each of the PHM marker loci and the corresponding reference sequence ID numbers are shown in Table 1. For PHM marker analysis, nested PCR reactions are performed, using the external and internal primers for each PHM marker. In the first PCR reaction, 0.90 µl of 10×PCR buffer, 0.18 µl of 10 mM dNTP mix, 0.27 µl of 50 mM MgCl$_2$, 1.50 µl of 2.5 µM external forward primer, 1.50 µl of 2.5 µM external reverse primer, 0.04 µl of Platinum Taq, 1.61 µl of ddH2O, and 3 µl of 1.5 ng/µl DNA are used. The thermocycling conditions constitute: 95° C. at 5 minutes; 94° C. for 20 seconds, 55° C. for 30 seconds, and 72° C. for 2 minutes, repeated for 24 cycles; 72° C. for 10 minutes; and a hold at 4° C. The DNA produced from the first round of PCR is then diluted 1:9 with TE for use in the second round of PCR. The reaction mix for the second round of PCR is the same except the internal sets of primers are used, and the DNA is the diluted DNA from the first round of PCR. The thermocycling conditions for the second round of PCR constitute: 95° C. at 5 minutes; 94° C. for 20 seconds, 55° C. for 30 seconds, and 72° C. for 2 minutes, repeated for 28 cycles; 72° C. for 10 minutes; and a hold at 4° C. The PCR products are then sequenced directly.

Each marker locus is examined, and standard statistical analysis, such as the student t-test or Kolmogorov-Smirnov test, can be used to determine if the trait distributions for each allele are significantly different from one another. If significant, the effect of this QTL on mechanical stalk strength would be validated.

Example 5

Validation of QTL5, QTL9, and QTL1A

A biparental population, PH07H×PH7CM, was developed for the purpose of validating QTL5, QTL9, and QTL1A. PH07H had a score of 19.569 in the association study and carries the favorable alleles at the QTL5 marker loci, PHM5421, PHM201, PHM12521, PHM10840, and PHM3468; at the QTL9 marker loci, PHM16736, PHM14053, PHM405, and PHM12025; and at the QTL1A marker locus PHM2130. PH7CM had a score of 7.596 and did not carry the favorable alleles at QTL5, QTL9, and QTL1A. $F_2$ individuals were genotyped, and siblings carrying only the favorable alleles at either QTL5, QTL9, or QTL1A were selected. The selected siblings were selfed twice before phenotyping $F_4$ individuals with an Instron™ machine after flowering. Plants carrying favorable alleles at QTL1A showed a greater positive effect on load at yield, dry weight, and diameter; however, favorable alleles at QTL5 increase stalk strength without a significant change in dry weight or diameter. No difference in stalk strength, dry weight, and diameter were seen amongst the siblings for the chromosome 9 segment. Data for stalk strength as measured by the Instron™ is shown in Table 8.

TABLE 8

|  | p-value | median (favorable allele) | median (unfavorable allele) |
|---|---|---|---|
| OTL1A | 3.81E-11 | 19.48 | 16.96 |
| QTL5 | 6.49E-04 | 19.58 | 17.83 |
| QTL9 | 1.66E-01 | 19.68 | 20.39 |

The apparent lack of association between QTL9 and mechanical stalk strength was resolved in another biparental population that was developed from a cross between PH891 and PH7CM. PH891 had a score of 14.863 in the association study and also carries the favorable alleles at QTL5, QTL9, and QTL1A. NILs (near isogenic lines) carrying only a sub-segment of the chromosome 9 region were created. A subsegment of the chromosome 9 QTL from PH7CM, in the region between 174.3 and 179 cM, had an overall positive effect on mechanical stalk strength, while a sub-segment of the chromosome 9 QTL from PH7CM in the region between 179 and 181 had an overall negative effect on mechanical stalk strength. This explains why there was no net gain in observed stalk strength amongst the $F_4$ siblings (described in the previous paragraph) that carried both segments together.

Example 6

Markers for Use in MAS of Plants with Increased Mechanical Stalk Strength

A set of production SNP markers specific for each chromosomal region has been developed (Table 9), and when used together, the markers can be used to identify the proper haplotype for the regions associated with mechanical stalk strength. The markers were developed by comparing the genotypes and phenotypes at a number of PHM marker loci in the intervals described herein (QTL1A, QTL1B, QTL5, and QTL9) for a parental panel of inbreds from NSS germplasm plus a few diverse lines. Markers were created using Invader Plus™ chemistry.

TABLE 9

Production Markers for Use In MAS

| Marker | QTL | PHB map position (cM) | Select For: | Select Against: |
|---|---|---|---|---|
| PHM18693-9-U | 1A | 106.7 | T |  |
| PHM10786-11-U | 1A | 107.8 | G |  |
| PHM10786-5-U | 1A | 107.8 | C |  |
| PHM10786-6-U | 1A | 107.8 | T |  |
| PHM8057-801-U | 1A | 110.2 | G |  |
| PHM4044-11-U | 1B | 132.4 |  | T |
| PHM14080-16-V | 1B | 133.2 |  | A |
| PHM15089-10-U | 1B | 133.7 |  | C |
| PHM9364-6-U | 1B | 135.5 |  | G |
| PHM201-16-U | 5 | 71.6 | C |  |
| PHM201-17-U | 5 | 71.6 | C or G |  |
| PHM4861-20-U | 5 | 71.6 | T or G |  |
| PHM4861-21-U | 5 | 71.6 | A |  |
| PHM5421-5-V | 5 | 72.2 | G |  |
| PHM4115-35-U | 5 | 73.4 | G or T |  |
| PHM12521-18-U | 5 | 74.9 | T |  |
| PHM12521-19-U | 5 | 74.9 | A |  |
| PHM12521-29-U | 5 | 74.9 | G |  |
| C00386-397-U | 5 |  | C |  |
| PHM13418-18 | 9 | 174.37 | C |  |
| PHM13418-10 | 9 | 174.37 | C |  |
| PHM113-7 | 9 | 180.76 | T |  |
| PHM10337-11-U | 9 | 181.2 | T$^i$ |  |
| PHM16736-8-V | 9 | 181.2 | A |  |
| PHM12025-48 | 9 | 179.78 | C |  |
| PHM11186-16-V | 9 | 181.5 | T |  |

What is claimed:

1. A method of obtaining maize plants with increased mechanical stalk strength, the method comprising:
   A. obtaining genetic material from a maize plant;
   B. analyzing the genetic material for the presence of a QTL allele associated with increased mechanical stalk strength, wherein the presence of said QTL allele is determined by detecting a haplotype within a chromosomal interval comprising and flanked by PHM201 and PHM3323 wherein said haplotype comprises a "C" at nucleotide position 178 of SEQ ID NO:10 and a "C" or "G" at nucleotide position 195 of SEQ ID NO:10;
   C. selecting a maize plant having said haplotype;
   D. crossing said maize plant to a second maize plant;
   E. evaluating the progeny for the haplotype; and
   F. selecting the progeny plants that possess the haplotype.

* * * * *